United States Patent
Hill et al.

(10) Patent No.: US 12,168,801 B1
(45) Date of Patent: Dec. 17, 2024

(54) HYBRID/CAPTURE PROBE DESIGNS FOR FULL-LENGTH cDNA

(71) Applicant: 10X Genomics, Inc., Pleasanton, CA (US)

(72) Inventors: Andrew John Hill, Oakland, CA (US); Katherine Pfeiffer, San Francisco, CA (US); Andrew Scott Kohlway, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 633 days.

(21) Appl. No.: 17/367,127

(22) Filed: Jul. 2, 2021

Related U.S. Application Data

(60) Provisional application No. 63/047,678, filed on Jul. 2, 2020.

(51) Int. Cl.
*C12Q 1/68* (2018.01)
*C12N 15/10* (2006.01)
(Continued)

(52) U.S. Cl.
CPC ....... *C12Q 1/6874* (2013.01); *C12N 15/1068* (2013.01); *C12Q 1/686* (2013.01); *C12Q 1/6876* (2013.01); *C12Q 2600/156* (2013.01)

(58) Field of Classification Search
None
See application file for complete search history.

(56) References Cited

U.S. PATENT DOCUMENTS 4,683,195 A 5/1987 Mullis et al.
4,683,202 A 5/1987 Mullis et al.
(Continued)

FOREIGN PATENT DOCUMENTS

EP 1336662 A2 8/2003
WO WO 2000/063437 A2 10/2000
(Continued)

OTHER PUBLICATIONS

Ray et al, Comprehensive identification of mRNA isoforms reveals the diversity of neural cell-surface molecules with roles in retinal development and disease, Nat Commun. Jul. 3, 2020;11(1):3328. doi: 10.1038/s41467-020-17009-7.*
(Continued)

*Primary Examiner* — Aaron A Priest

(57) ABSTRACT

Systems and methods for identifying and using hybrid/capture probes are provided. cDNA sequences from polyadenylated mRNA are obtained. Each cDNA sequence in a first subset maps to a gene in a plurality of genes. Each cDNA sequence in a second subset maps to a reference genome portion not represented by the plurality of genes. Each gene has a corresponding plurality of transcripts. The cDNA sequences are exposed to at least $2\times10^3$ nucleic acid baits between $K_1$ and $K_2$ residues long, forming nucleic acid bait—sequence read complexes. Each nucleic acid bait that hybridizes to a cDNA sequence mapping to a gene selectively hybridizes to a first subset or another subset of transcripts corresponding to the gene. Each transcript of each gene is hybridizable to a nucleic acid bait in the at least $2\times10^3$ nucleic acid baits. The nucleic acid bait—sequence read complexes are captured and analyzed.

34 Claims, 19 Drawing Sheets

(51) Int. Cl.
*C12Q 1/686* (2018.01)
*C12Q 1/6874* (2018.01)
*C12Q 1/6876* (2018.01)

(56) References Cited

U.S. PATENT DOCUMENTS

| | | | |
|---|---|---|---|
| 4,800,159 | A | 1/1989 | Mullis et al. |
| 4,965,188 | A | 8/1990 | Mullis et al. |
| 5,472,881 | A | 12/1995 | Beebe et al. |
| 5,512,462 | A | 4/1996 | Cheng |
| 5,599,675 | A | 2/1997 | Brenner |
| 5,610,287 | A | 3/1997 | Nikiforov et al. |
| 5,807,522 | A | 9/1998 | Brown et al. |
| 5,837,860 | A | 11/1998 | Anderson et al. |
| 5,919,626 | A | 7/1999 | Shi et al. |
| 6,172,218 | B1 | 1/2001 | Brenner |
| 6,210,891 | B1 | 4/2001 | Nyren et al. |
| 6,258,568 | B1 | 7/2001 | Nyren |
| 6,265,552 | B1 | 7/2001 | Schatz |
| 6,266,459 | B1 | 7/2001 | Walt et al. |
| 6,274,320 | B1 | 8/2001 | Rothbert et al. |
| 6,306,597 | B1 | 10/2001 | Macevicz |
| 6,355,431 | B1 | 3/2002 | Chee et al. |
| 6,391,937 | B1 | 5/2002 | Beuhler et al. |
| 6,737,236 | B1 | 5/2004 | Pieken et al. |
| 6,770,441 | B2 | 8/2004 | Dickinson et al. |
| 6,859,570 | B2 | 2/2005 | Walt et al. |
| 6,867,028 | B2 | 3/2005 | Janulaitis et al. |
| 6,969,488 | B2 | 11/2005 | Bridgham et al. |
| 7,001,792 | B2 | 2/2006 | Sauer et al. |
| 7,057,026 | B2 | 6/2006 | Barnes et al. |
| 7,259,258 | B2 | 8/2007 | Kozlov et al. |
| 7,375,234 | B2 | 5/2008 | Sharpless et al. |
| 7,427,678 | B2 | 9/2008 | Pieken et al. |
| 7,709,198 | B2 | 5/2010 | Luo et al. |
| 8,460,865 | B2 | 6/2013 | Chee et al. |
| 8,604,182 | B2 | 12/2013 | Luo et al. |
| 8,951,726 | B2 | 2/2015 | Luo et al. |
| 9,012,390 | B2 | 4/2015 | Holtze et al. |
| 9,512,422 | B2 | 12/2016 | Barnard et al. |
| 9,694,361 | B2 | 7/2017 | Bharadwaj et al. |
| 9,727,810 | B2 | 8/2017 | Fodor et al. |
| 9,783,841 | B2 | 10/2017 | Nolan et al. |
| 9,889,422 | B2 | 2/2018 | Smith et al. |
| 10,002,316 | B2 | 6/2018 | Fodor et al. |
| 10,041,949 | B2 | 8/2018 | Bendall et al. |
| 10,053,723 | B2 | 8/2018 | Hindson et al. |
| 10,059,990 | B2 | 8/2018 | Boyden et al. |
| 10,071,377 | B2 | 9/2018 | Bharadwaj et al. |
| 10,137,449 | B2 | 11/2018 | Bharadwaj et al. |
| 10,138,509 | B2 | 11/2018 | Church et al. |
| 10,150,117 | B2 | 12/2018 | Bharadwaj et al. |
| 10,150,964 | B2 | 12/2018 | Hindson et al. |
| 10,179,932 | B2 | 1/2019 | Church et al. |
| 10,221,442 | B2 | 3/2019 | Hindson et al. |
| 10,343,166 | B2 | 7/2019 | Bharadwaj et al. |
| 10,347,365 | B2 | 7/2019 | Wong et al. |
| 10,400,235 | B2 | 9/2019 | Belhocine et al. |
| 10,428,326 | B2 | 10/2019 | Belhocine et al. |
| 10,550,429 | B2 | 2/2020 | Harada et al. |
| 10,610,865 | B2 | 4/2020 | Bharadwaj et al. |
| 10,815,525 | B2 | 10/2020 | Lucero et al. |
| 11,041,202 | B2 | 6/2021 | Robins et al. |
| 2005/0100900 | A1 | 5/2005 | Kawashima et al. |
| 2006/0188901 | A1 | 8/2006 | Barnes et al. |
| 2006/0240439 | A1 | 10/2006 | Smith et al. |
| 2006/0281109 | A1 | 12/2006 | Ost et al. |
| 2007/0166705 | A1 | 7/2007 | Milton et al. |
| 2008/0280773 | A1 | 11/2008 | Fedurco et al. |
| 2009/0026082 | A1 | 1/2009 | Rothberg et al. |
| 2009/0127589 | A1 | 5/2009 | Rothberg et al. |
| 2010/0055733 | A1 | 3/2010 | Lutolf et al. |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2011/0172105 | A1* | 7/2011 | Gage ............... C12N 15/1096 536/23.1 |
| 2012/0270305 | A1 | 10/2012 | Williamson et al. |
| 2013/0079232 | A1 | 3/2013 | Kain et al. |
| 2013/0260372 | A1 | 10/2013 | Buermann et al. |
| 2014/0079923 | A1 | 3/2014 | George et al. |
| 2014/0155295 | A1 | 6/2014 | Hindson et al. |
| 2014/0378345 | A1 | 12/2014 | Hindson et al. |
| 2015/0376609 | A1 | 12/2015 | Hindson et al. |
| 2015/0376700 | A1 | 12/2015 | Schnall-Levin et al. |
| 2017/0016053 | A1 | 1/2017 | Beechem et al. |
| 2017/0253918 | A1 | 9/2017 | Kohman et al. |
| 2018/0052081 | A1 | 2/2018 | Kohman et al. |
| 2018/0105808 | A1 | 4/2018 | Mikkelsen et al. |
| 2018/0156784 | A1 | 6/2018 | Usmani et al. |
| 2018/0245142 | A1 | 8/2018 | So et al. |
| 2018/0312873 | A1 | 11/2018 | Zheng |
| 2019/0032121 | A1 | 1/2019 | Daugharthy et al. |
| 2019/0177800 | A1 | 6/2019 | Boutet et al. |
| 2019/0323088 | A1 | 10/2019 | Boutet et al. |
| 2019/0367969 | A1 | 12/2019 | Bell et al. |
| 2020/0392479 | A1* | 12/2020 | Blainey ............... C12N 1/205 |
| 2021/0174898 | A1* | 6/2021 | Bell ..................... G16B 20/40 |
| 2021/0241853 | A1 | 8/2021 | Hepler et al. |
| 2022/0220470 | A1* | 7/2022 | Pan ....................... C12Q 1/6869 |

FOREIGN PATENT DOCUMENTS

| | | | |
|---|---|---|---|
| WO | WO 2005/065814 A1 | 7/2005 | |
| WO | WO 2006/064199 A1 | 6/2006 | |
| WO | WO 2007/010251 A2 | 1/2007 | |
| WO | WO-2009099602 A1 * | 8/2009 | ........... C12Q 1/6811 |
| WO | WO 2011/094669 A1 | 8/2011 | |
| WO | WO 2011/127099 A1 | 10/2011 | |
| WO | WO 2012/140224 A1 | 10/2012 | |
| WO | WO 2014/060483 A1 | 4/2014 | |
| WO | WO 2014/163886 A1 | 10/2014 | |
| WO | WO 2014/189957 | 11/2014 | |
| WO | WO 2014/210225 A1 | 12/2014 | |
| WO | WO 2014/210233 A1 | 12/2014 | |
| WO | WO 2014/210353 | 12/2014 | |
| WO | WO 2015/161173 A1 | 10/2015 | |
| WO | WO 2015/200871 | 12/2015 | |
| WO | WO 2016/007839 | 1/2016 | |
| WO | WO 2016/057552 | 4/2016 | |
| WO | WO 2016/162309 | 10/2016 | |
| WO | WO 2016/166128 | 10/2016 | |
| WO | WO 2017/027367 | 2/2017 | |
| WO | WO 2017/027368 | 2/2017 | |
| WO | WO 2017/144338 | 8/2017 | |
| WO | WO 2017/147483 | 8/2017 | |
| WO | WO 2017/222453 | 12/2017 | |
| WO | WO 2018/022809 | 2/2018 | |
| WO | WO 2018/045181 | 3/2018 | |
| WO | WO 2018/045186 | 3/2018 | |
| WO | WO 2018/057999 | 3/2018 | |
| WO | WO 2018/075693 | 4/2018 | |
| WO | WO 2018/091676 | 5/2018 | |
| WO | WO 2018/107054 | 6/2018 | |
| WO | WO 2018/119447 | 6/2018 | |
| WO | WO 2018/136856 | 7/2018 | |
| WO | WO 2018/218226 | 11/2018 | |
| WO | WO 2019/068880 | 4/2019 | |
| WO | WO 2019/075091 | 4/2019 | |
| WO | WO 2019/157529 | 8/2019 | |
| WO | WO-2020092646 A1 * | 5/2020 | ......... C12N 15/1003 |
| WO | WO-2021242793 A2 * | 12/2021 | ......... C12N 15/1037 |

OTHER PUBLICATIONS

Gnirke et al, Solution hybrid selection with ultra-long oligonucleotides for massively parallel targeted sequencing, Nat Biotechnol. Feb. 2009;27(2):182-9. doi: 10.1038/nbt. 1523. Epub Feb. 1, 2009.*
Yap et al, Polarizing the Neuron through Sustained Co-expression of Alternatively Spliced Isoforms, Cell Rep. May 10, 2016;15(6): 1316-28. doi: 10.1016/j.celrep.2016.04.012. Epub Apr. 28, 2016.*
U.S. Appl. No. 17/239,555, filed Apr. 24, 2021.
U.S. Appl. No. 17/168,050, filed Feb. 4, 2021.

(56) References Cited

OTHER PUBLICATIONS

U.S. Appl. No. 17/464,561, filed Sep. 1, 2021.
U.S. Appl. No. 63/011,779, entitled "Systems and Methods for Visualizing Adaptive Immune Cell Clonotyping Data," filed Apr. 17, 2020.
U.S. Appl. No. 63/011,783, entitled "Systems and Methods for Identifying Adaptive Immune Cell Clonotypes," filed Apr. 17, 2020.
U.S. Appl. No. 63/073,830, entitled "Systems and Methods for Identifying Cells That are Antigen-Specific for an Immunogenic Feature," filed Sep. 2, 2020.
U.S. Appl. No. 62/017,589, entitled "Processes and Systems for Nucleic Acid Sequence Assembly" filed Jun. 26, 2014.
U.S. Appl. No. 62/969,897 entitled "Systems and Methods for Index Hopping Filtering," filed Feb. 4, 2020.
U.S. Appl. No. 63/022,988 entitled "Systems and Methods for Index Hopping Filtering," filed May 11, 2020.
U.S. Appl. No. 62/041,825, entitled "Pipeline for Spatial Analysis of Analytes," filed Jun. 20, 2020.
U.S. Appl. No. 62/047,678, entitled "Systems and Methods for Identifying Morphological Patterns in Tissue Samples," filed Jun. 20, 2020.
U.S. Appl. No. 62/047,678 entitled "Biomarkers for Distinguishing Between Aggressive Prostate Cancer and Non-Aggressive Prostate Cancer," filed Jul. 2, 2020.
U.S. Appl. No. 62/839,346 entitled "Spatial Transcriptomics of Biological Analytes in Tissue Samples," filed Apr. 26, 2019.
U.S. Appl. No. 62/886,233, entitled "Systems and Methods for Using the Spatial Distribution of Haplotypes to Determine a Biological Condition" filed Aug. 13, 2019.
U.S. Appl. No. 62/929,686 entitled "Capturing Targeted Genetic Targets Using A Hybridization/Capture Approach", filed.
U.S. Appl. No. 62/938,336, entitled "Pipeline for Spatial Analysis of Analytes," and filed Nov. 21, 2019.
U.S. Appl. No. 62/970,066, entitled "Capturing Targeted Genetic Targets Using A Hybridization/Capture Approach", filed Feb. 4, 2020.
U.S. Appl. No. 62/979,889, entitled "Capturing Targeted Genetic Targets Using A Hybridization/Capture Approach", filed Feb. 21, 2020.
U.S. Appl. No. 17/078,288, entitled "Capturing Targeted Genetic Targets Using a Hybridization/Capture Approach" filed Oct. 23, 2020.
10X Genomics, "What is a template switch oligo (TSO)?," https://kb.10xgenomics.com/hc/en-us/articles/360001493051-What-is-a-template-switch-oligo-TSO.
10X Genomics, "What is the difference between Single Cell 3' and 5' Gene Expression libraries?" available on the Internet at kb.10xgenomics.com/hc/en-us/articles/360000939852-What-is-the-difference-between-Single-Cell-3-and-5-Gene-Expression-libraries.
10X Genomics, Enclone, Internet at Github at 10XGenomics/enclone, last accessed Aug. 31, 2020.
10X Genomics, A "MegaCell Demonstration" by (10X Genomics Datasets, 2017, on the Internet at 10xgenomics.com/solutions/single-cell/).
10X Genomics, 2020, "Technical Note—Interpreting Intronic and Antisense Reads in Single Cell Gene Expression Data", Document No. CG000376, Rev A.
10X Genomics, 2019, "Chromium Next GEM Single Cell 3' Reagent Kits v3.1 User Guide", Document No. CG000204, Rev D.
10X Genomics, 2017, "Chromium Single Cell 3' Reagent Kits v2 User Guide," Document No. CG00052 Rev B.
10X Genomics, 2020, "Chromium Single Cell V(D)J Reagents Kits User Guide," Document No. CG000086, Rev M.
10X Genomics, 2021, "Targeted Gene Expression—Single Cell User Guide", Document No. CG000293, Rev E.
Bailey et al., 2018, "Comprehensive Characterization of Cancer Driver Genes and Mutations," Cell 173(2), pp. 371-385.
Behan et al., 2019, Prioritization of cancer therapeutic targets using CRISPR-Cas9 screens, Nature 568, pp. 511-516.
Blasi et al. 2016, "Label-free cell cycle analysis for high-throughput imaging flow cytometry," Nat. Commun. 7:10256 doi: 10.1038/ncomms10256.
Blondel et al., Jul. 25, 2008, "Fast unfolding of communities in large networks," arXiv:0803.0476v2.
Bourcy et al., 2014, "A Quantitative Comparison of Single-Cell Whole Genome Amplification Methods," PLOS ONE 9(8), e105585.
Caicedo et al., 2017, "Data-analysis strategies for image-based cell profiling," Nature Methods 14(9), pp. 849-863.
Chen et al., 2010, "Clustering-based identification of clonally-related immunoglobulin gene sequence sets," Immunome Res. 6 Suppl 1:S4.
Chen et al., Science 348(6233):aaa6090, 2015.
Compeau et al., 2017, "Why are de Bruijn graphs useful for genome assembly?" Nat Biotechnol. 29(11):987-991: doi:10.1038/nbt.2023.
Costello et al., 2018, "Characterization and remediation of sample index swaps by non-redundant dual indexing on massively parallel sequencing platforms," BMC Genomics.
Cunningham, 2007, "Dimension Reduction," University College Dublin, Technical Report UCD-CSI-2007-7.
Cunningham et al., Ensembl 2019, PubMed PMID: 30407521, doi:10.1093/nar/gky1113.
Dave Tang's Blog, "10x single cell BAM files", https://davetang.org/muse/2018/06/06/10x-single-cell-bam-files/.
Denisenko et al., 2019, "Systematic assessment of tissue dissociation and storage biases in single-cell and single-nucleus RNA-seq workflows," bioRxiv preprint doi: https://doi.org/10.1101/832444.
De Vos, 2010, "High content image cytometry in the context of subnuclear organization," Cytometry Part A 77A, pp. 64-75.
Diggins, K.E., P. Brent Ferrell Jr, and Jonathan M. Irish. "Methods for discovery and characterization of cell subsets in high dimensional mass cytometry data." Methods 82 (2015): 55-63.
Fang et al., 2003, "Fluoride-Cleavable Biotinylation Phosphoramidite for 5'-end-Labelling and Affinity Purification of Synthetic Oligonucleotides," Nucleic Acids Res. 31(2), pp. 708-715.
Fang et al., 2019, "A genetics-led approach defines the drug target landscape of 30 immune-related traits," Nature Genetics 51(7); pp. 1082-1091.
Farouni et al., 2019, "Statistical modeling, estimation, and remediation of sample index hopping in multiplexed droplet-based single-cell RNA-seq data," bioRxiv preprint posted online Apr. 24, 2019; doi: 10.1101/617225.
Fodor, 2002, "A survey of dimension reduction techniques," Center for Applied Scientific Computing, Lawrence Livermore National, Technical Report UCRL-ID-148494.
Ganusov et al., 2007, "Do most lymphocytes in humans really reside in the gut?," Trends Immunol, 208(12), pp. 514-518.
Gao et al., BMC Biol. 15:50, 2017.
Giansanti, 2020, "Fast analysis of scATAC-seq data using a predefined set of genomic regions," F1000Research 9, 199.
Gnirke et al., 2009, "Solution Hybrid Selection with Ultra-long Oligonucleotides for Massively Parallel Targeted Sequencing," Nature Biotechnology. Feb. 27(2): 182-189, doi:10.1038/nbt.1523.
Griffiths et al., 2018, "Detection and removal of barcode swapping in single-cell RNA-seq data," Nature Communications 9, Article No. 2667.
Gupta et al., Nature Biotechnol. 36:1197-1202, 2018.
Hershberg et al., 2015, "The analysis of clonal expansion in normal and autoimmune B cell repertoires," Philos Trans R Soc Lond B Biol Sci. 370(1676).
Hoadley et al., 2018, Cell-of-Origin Patterns Dominate the Molecular Classification of 10,000 Tumors from 33 Types of Cancer, Cell 173(2), pp. 291-304.
Hong, 2018, "QSurface: fast identification of surface expression markers in cancer," BMC Syst Biol. 12(Suppl 2):17, doi:10.1186/s12918-018-0541-6.
Illumina, "Effects of index misassignment on multiplexing and downstream analysis," on the Internet at illumina.com, 2017.
Illumina, "An introduction to Next-Generation Sequencing Technology" illumina.com/content/dam/illumina-marketing/documents/products/illumina_sequencing_introduction.pdf, last accessed Feb. 1, 2020.

(56) References Cited

OTHER PUBLICATIONS

Kandoth et al., 2013, "Mutational landscape and significance across 12 major cancer types," Nature 502(7471), p. 333-339.
Kurtz et al., 2004, "Versatile and open software for comparing large genomes," Genome Biol doi: 10.1186/gb-2004-5-2-r12.
Kuznetsova et al., 2017, "Generation of populations of antigen-specific cytotoxic T cells using DSs transfected with DNA construct encoding HER2/neu tumor antigen epitopes," BMI Immunology 18:31.
Larsson, A.J.M. et al., "Computational correction of index switching in multiplexed sequencing libraries" Nature Methods vol. 14 No. 5 May 2018.
Lee et al., "Fluorescent in situ Sequencing (FISSEQ) of RNA for Gene Expression Profiling in Intact Cells and Tissues", Nat. Protoc. 10(3):442-458, 2015.
Lee et al., 2019, "Multi-ATOM: Ultrahigh-throughput single-cell quantitative phase imaging with subcellular resolution," Journal of Biophotonics doi.org/10.1002/jbio.201800479.
Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi:10.1182/blood-2003-11-3857.
Li, Q., "Reliable multiplex sequencing with rare index misassignment on DNB-based NGS platform" BMC Genomics (2019) 20:215.
Liu, D. 2019. Algorithms for efficiently collapsing reads with Unique Molecular Identifiers. Peer J 7:e8275 http://doi.org/10.7717/peerj.8275 (Year: 2019).
Liu, P., et al. "Recent advances in computer-assisted algorithms for cell subtype identification of cytometry data." Frontiers in cell and developmental biology 8 (2020): 234.
MacConaill, L.E. et al., (2018). "Unique, dual-indexed sequencing adapters with UMIs effectively eliminate index cross-talk and significantly improve sensitivity of massively parallel sequencing." BMC genomics, 19, 1-10.
Malkov and Yashunin, 2016, "Efficient and robust approximate nearest neighbor search using Hierarchical Navigable Small World graphs," arXiv: 1603.09320 at arxiv.org/abs/1603.09320.
Marks et al., 2020, "How repertoire data is changing antibody science," The Journal of Biological Chemistry 295, 9823-9837.
Matsuda et al., 1998, "The complete nucleotide sequence of the human immunoglobulin heavy chain variable region locus," The Journal of Experimental Medicine. 188 (11): 2151-62, doi: 10.1084/jem.188.11.2151.
Miles et al., 2011, "Bias in the αβ T-cell repertoire: implications for disease pathogenesis and vaccination," Immunol Cell Biol. 89, pp. 375-387.
Mostovoy et al., 2016, "A hybrid approach for de novo human genome sequence assembly and phasing," Nat. Methods 13, 587-590.
Narasimhan et al., 2016, "Health and population effects of rare gene knockouts in adult humans with related parents," Science 352, pp. 474-477 (2016).
Navin et al., 2011, "Tumour evolution inferred by single-cell sequencing," Nature 472, pp. 90-94.
Ning, Z., et al., "A Fast Search Method for Large DNA Databases. Genome Research," 2001, 11, 1725-1729.
Padmaja, et al. (Aug. 18, 2016). 2016 IEEE 6th International Conference on Advanced Computing (IACC). pp. 31-34. doi:10.1109/IACC.2016.16, ISBN 978-1-4673-8286-1.
Peng et al., 2015, "Reducing amplification artifacts in high multiplex amplicon sequencing by using molecular barcodes," BMC Genomics. 16(1):589, doi:10.1186/s12864-015-1806-8.
Petegrosso, R. et al. "Machine learning and statistical methods for clustering single-cell RNA-sequencing data." Briefings in bioinformatics 21.4 (2020): 1209-1223.
Quadratic-Time, https://inst.eecs.berkeley.edu/~cs10/labs/cur/programming/algorithms/timing/quadratic-time.html?topic=berkeley_bjc%2Fareas%2Falgorithm-complexity.topic&course=berkeley_bjc.html&noassignment.
Ramani, V., et al. (2017). Massively multiplex single-cell Hi-C. Nature methods, 14(3), 263-266.
Rodriques et al., Science 363(6434):1463-1467, 2019.
Rosati, 2017, "Overview of methodologies for T-cell receptor repertoire analysis," BMC Biotechnology 17:61.
Sanchez-Vega et al., 2018, "Oncogenic Signaling Pathways in The Cancer Genome Atlas," Cell 173(2), pp. 321-337.
Sinha et al., 2017, "Index switching causes 'spreading-of-signal' among multiplexed samples in Illumina HISEQ 4000 DNA sequencing," bioRxiv.
Smith, A.N.S. et al., (2019). Dual indexed design of in-Drop single-cell RNA-seq libraries improves sequencing quality and throughput. bioRxiv, 835488.
Snyder et al., 2012, "Clonal Evolution of Preleukemic Hematopoietic Stem Cells Precedes Human Acute Myeloid Leukemia," Science Translational Medicine 4, 149ra118.
Spitzer et al., 2016, "Mass Cytometry: Single Cells, Many Features," Cell 165(4), pp. 780-791.
Stassen et al., "PARC: ultrafast and accurate clustering of phenotypic data of millions of single cells," BioRxiv preprint doi.org/10.1101/765628.
Stoeckius, M. et al. "Cell Hashing with barcoded antibodies enables multiplexing and doublet detection for single cell genomics" Genome Biology (2018) 19:224 (Year: 2018).
Tandonnet et al., 2017, "Traditional versus 3' RNA-seq in a non-model species," Genom Data. 11:9-16, doi:10.1016/j.gdata.2016.11.002.
Tario et al., 2015, "Dextramer Reagents are Effective Tools for Quantifying CMV Antigen-Specific T Cells from Peripheral Blood Samples," Cytometry Part B (Clinical Cytometry) 888:6-20.
Thermofisher Scientific Invitrogen, technical note "How to prevent index hopping" 2019.
Thorsson et al., 2018, "The Immune Landscape of Cancer," Immunity 48(4), pp. 812-830.
Traag et al., 2019, "From Louvain to Leiden: guaranteeing well-connected communities," Scientific Reports 9: 5233 at doi.org/10.1038/s41598-019-41695-z.
Trejo et al., PLoS ONE 14(2):e0212031, 2019.
Turner et al., 2006, Structural determinants of T cell receptor bias in immunity, Nat Rev Immunol 6, pp. 883-894.
Unix & Linux Stack Exchange, "Sorting Lexicographically by 'all fields'", https://unix.stackexchange.com/questions/307293/sorting-lexicographically-by-all-fields.
Vigneron, 2015, "Human Tumor Antigens and Cancer Immunotherapy," BioMed Research International 2015, Article ID 948501.
Voet et al., 2013, "Single-cell paired-end genome sequencing reveals structural variation per cell cycle," Nucleic Acids Res 41: 6119-6138.
Wentian et al., 2014, "Diminishing return for increased Mappability with longer sequencing reads: implications of the k-mer distributions in the human genome," BMC Bioinformatics 15(2).
Wolfgang et al., 2007, "Graphs in molecular biology," BMC Bioinformatics. 8(Suppl 6): S8: doi:10.1186/1471-2105-8-S6-S8.
Wu et al., 2015, "Maturation and Diversity of the VRC01-Antibody Lineage over 15 Years of Chronic HIV-1 Infection," Cell 161(3), pp. 470-485.
Xu et al., 2015, "A Comprehensive Survey of Clustering Algorithms," Ann. Data. Sci. 2(2) 165-193.
Yaari et al., 2015, "Practical guidelines for B cell repertoire sequencing analysis," Genome Medicine 7:121.
Yassai et al., 2009, "A clonotype nomenclature for T cell receptors," Immunogenetics 61, pp. 493-502.
Zahorian et al., 2011, "Nonlinear Dimensionality Reduction Methods for Use with Automatic Speech Recognition," Speech Technologies. doi:10.5772/16863. ISBN 978-953-307-996-7.
Zheng et al., 2016 "Haplotyping germline and cancer genomes with high-throughput linked-read sequencing," Nat. Biotechnol. 34, pp. 303-311.

(56) References Cited

OTHER PUBLICATIONS

Zheng et al., 2017, "Massively parallel digital transcriptional profiling of single cells," Nat. Commun. 8, 14049 doi: 10.1038/ncomms14049.

Zong et al., 2012, "Genome-wide detection of single nucleotide and copy-number variations of a single human cell," Science 338, pp. 1622-1626.

\* cited by examiner

200

— 202

Obtain a plurality of cDNA sequences from a pool of poly-adenylated mRNA obtained from a biological sample of a subject. The plurality of cDNA sequences comprise a first subset of cDNA sequences and a second subset of cDNA sequences.

Each respective cDNA sequence in the first subset of cDNA sequences maps to a respective gene in a plurality of genes. Each respective cDNA sequence in the second subset of cDNA sequences maps to a portion of a reference genome not represented by the plurality of genes.

Each respective gene in the plurality of genes is characterized by a corresponding plurality of transcripts.

— 204

The pool of poly-adenylated mRNA is obtained from the biological sample by single cell 3' sequencing, single cell 5' sequencing, or single cell 5' paired-end sequencing.

— 206

The plurality of cDNA sequences is at least $1 \times 10^6$ cDNA sequences.

— 208

The plurality of genes is between five genes and twenty thousand genes.

— 210

The plurality of transcripts corresponding to the respective gene comprises three or more transcripts for the respective gene.

— 212

The corresponding plurality of transcripts of a respective gene in the plurality of genes comprises a plurality of isoforms of the respective gene.

— 214

The plurality of isoforms of the respective gene comprises a first transcriptional isoform and a second transcriptional isoform of the respective gene.

— 216

Each transcript in the plurality of transcripts corresponding to the respective gene is protein coding.

— 218

The plurality of transcripts corresponding to the respective gene is each transcript of the respective gene annotated in GENCODE Release 33 (GRCh38.p13).

220 — Expose the plurality of cDNA sequences to a plurality of at least $2 \times 10^3$ nucleic acid baits each of length that is between K1 and K2 residues, forming a plurality of nucleic acid bait - sequence read complexes.
Each respective nucleic acid bait in the plurality of nucleic acid baits that hybridizes to a cDNA sequence mapping to a respective gene in the plurality of genes:
- selectively hybridizes to a first subset of transcripts in a plurality of subsets of transcripts in the plurality of transcripts corresponding to the respective gene, or
- selectively hybridizes to another subset of transcripts, other than the first subset of transcripts, in the plurality of subsets of transcripts in the plurality of transcripts corresponding to the respective gene.

Each respective transcript in the corresponding plurality of transcripts of each respective gene in the plurality of genes is hybridizable to a nucleic acid bait in the plurality of nucleic acid baits.

222 — The first subset of transcripts consists of two or more transcripts.

224 — The another subset of transcripts consists of two or more transcripts.

226 — The plurality of nucleic acid baits includes a minimum number of baits necessary to selectively hybridize to each respective transcript in the corresponding plurality of transcripts for a respective gene in the plurality of genes.

228 — K1 is 25 and K2 is 1000.

230 — Each respective substring of fixed length P nucleotides in each respective nucleic acid bait in the plurality of nucleic acid baits is represented in the reference genome less than a threshold number of times L.

232 — P is at least 15 nucleotides.

234 — L is between 2 and 50.

┌─ 236

Modify a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L.
The modifying comprises:
- removing the respective nucleic acid bait from the plurality of nucleic acid baits.
- truncating the respective nucleic acid bait such that the respective nucleic acid bait is represented in the reference genome at a position that is at least M base pairs away from any portion of the reference genome that comprises the substring of fixed length P, or
- shifting the respective sequence of the nucleic acid bait along the reference genome such that the respective sequence of the nucleic acid bait is represented in the reference genome at a position that is at least M base pairs away from any portion of the reference genome that comprises the substring of fixed length P.

┌─ 238

P is between 10 and 75.

┌─ 240

L is between 2 and 1000.

┌─ 242

Design a nucleic acid bait in the plurality of nucleic acid baits for a respective gene in the plurality of genes using:
- when the length of the coding sequence of the respective gene satisfies a predetermined length threshold, the coding sequence of the respective gene, and
- when the length of the coding sequence of the respective gene does not satisfy a predetermined length threshold, an mRNA sequence of the respective gene.

┌─ 244

Filter the plurality of nucleic acid baits for mappability, absence of repetitive subsequences, and/or overall GC content.

Figure 2C

314

For each respective sub-sequence of length K residues of the respective candidate hybridization sequence, determine a count of a number of transcripts in the corresponding plurality of transcripts, other than those transcripts in the corresponding first subset of transcripts, the respective sub-sequence matches, thus determining a corresponding second sub-sequence that matches a second maximal number of transcripts in the corresponding plurality of transcripts other than those transcripts in the corresponding first subset of transcripts.

The transcripts in the corresponding plurality of transcripts that match the second sub-sequence define a corresponding second subset of transcripts, in the corresponding plurality of subset of transcripts within the corresponding plurality of transcripts.

316

Include a nucleic acid bait corresponding to the corresponding first sub-sequence in the plurality of nucleic acid baits.

Include a nucleic acid bait corresponding to the corresponding second sub-sequence in the plurality of nucleic acid baits.

318

When the corresponding first subset of transcripts and the corresponding second subset of transcripts fail to account for all the transcripts in the corresponding plurality of transcripts:
- For each respective sub-sequence of length K residues of the respective candidate hybridization sequence, determine a count of a number of transcripts in the corresponding plurality of transcripts, other than those transcripts in the corresponding first or second subset of transcripts, the respective sub-sequence matches, thus determining a corresponding third sub-sequence that matches a third maximal number of transcripts in the corresponding plurality of transcripts, other than those transcripts in the corresponding first and second subset of transcripts. The transcripts in the corresponding plurality of transcripts that match the third sub-sequence define a corresponding third subset of transcripts, in the corresponding plurality of subsets of transcripts within the corresponding plurality of transcripts.
- Include a nucleic acid bait corresponding to the corresponding third sub-sequence in the plurality of nucleic acid baits.

Figure 3B

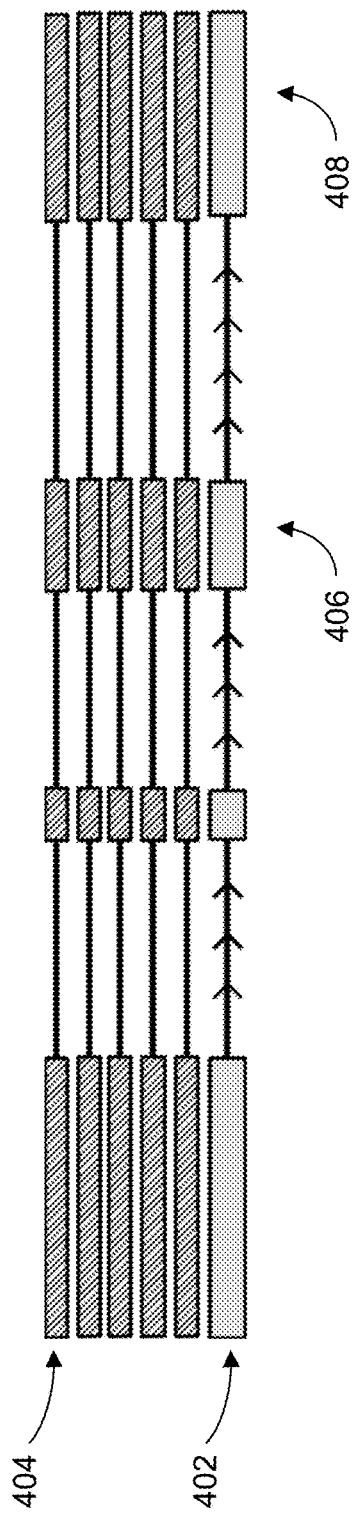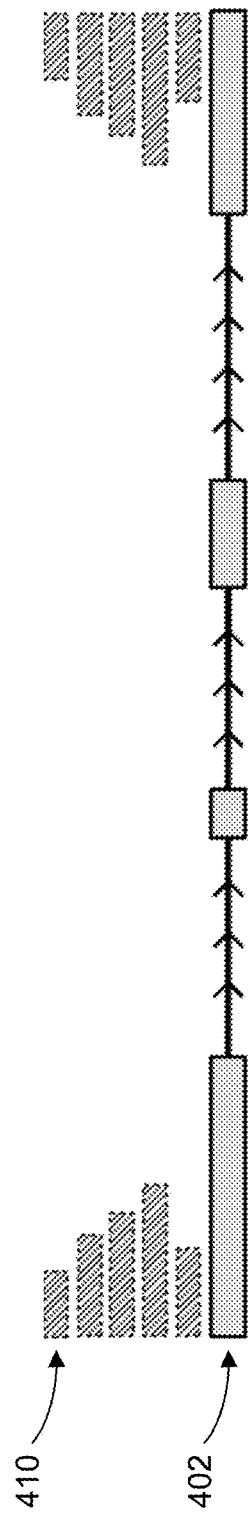

Final library from SC3Pv3 GEX
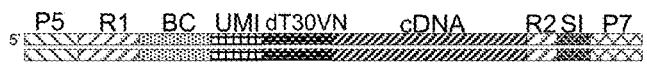
↓ + Biotinylated hybridization bait pool
Hybridize baits & blockers to single stranded library members
↓
Pull down baits and hybridized library to streptavidin beads
Wash beads to remove unbound probes
PCR on streptavidin beads to reamplify targeted library
↓ Final Library QC (Bioanalyzer, P5 - P7 qPCR)
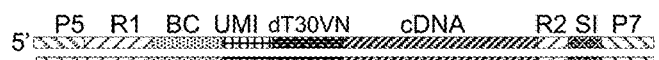
Sequence targeted library
Figure 6

HYBRID/CAPTURE PROBE DESIGNS FOR FULL-LENGTH cDNA

CROSS REFERENCE TO RELATED APPLICATIONS

This application claims priority to U.S. Provisional Patent Application No. 63/047,678, filed Jul. 2, 2020, the content of which is hereby incorporated by reference, in its entirety, for all purposes.

TECHNICAL FIELD

This specification describes technologies relating to capturing genetic targets using a hybridization/capture approach.

BACKGROUND

One of the most requested features of single-cell RNA sequencing (RNAseq) is to be able to obtain information from a set of specific transcripts rather than from the entire transcriptome. This would mean, for instance, fishing rare transcripts from a very complex pool of library molecules. For example, RNAseq is commonly applied towards differential gene expression analysis, in which the transcript levels for a specific panel of target genes are qualitatively or quantitatively assessed. In some applications, specific target sequences for rare or low copy number reads are obscured by the presence of high copy number or highly expressed sequences. In some instances, a user may want to profile the phenotype of a sample while avoiding confounding biological factors (e.g., strongly expressed genes that are not relevant to the study or cell cycle phenotypes that could mask other biological variance). In such cases, designing a set of probes that select for and isolate only target sequences of interest can improve the resolution of the sequencing analysis.

Capture-based target enrichment of the sequences of interest (e.g. a specific gene or panel of genes) from a plurality of sequences (e.g. a cDNA library or mRNA library) occurs via hybridization of synthetic oligonucleotide probes to their respective target sequences. The synthetic probes are biotinylated, which allows them to be subsequently captured on beads coated with streptavidin. Downstream assays including but not limited to PCR amplification, reverse transcription, or next-generation sequencing is then performed on the target sequences following hybridization and capture. See, Gnirke et al., 2009, "Solution Hybrid Selection with Ultra-long Oligonucleotides for Massively Parallel Targeted Sequencing," Nature Biotechnology. February; 27(2): 182-189, doi: 10.1038/nbt.1523, the entire contents of which are incorporated herein by reference.

Traditional approaches to RNAseq transcript analysis utilize exome pull-down for capture-based target enrichment or PCR amplification for non-capture-based target enrichment (see, Roche, "Hybridization-Based Target Enrichment," available on the internet at sequencing.roche.com/en/products-solutions/by-category/target-enrichment/hybridization.html, the entire contents of which are incorporated herein by reference). Exome pull-down, however, suffers from disadvantages arising from the differences between processing genomic DNA and RNA. For example, while genome fragmentation is relatively linear, RNA fragmentation typically takes into account any number of potential variations made possible by alternative splicing. Furthermore, due to the relatively small size of exons in comparison to full-length RNA transcripts, probes that are specifically designed for exon hybridization may hybridize poorly to cDNA or RNA fragments, resulting in inefficient pull-down and loss of data. See, Tandonnet et al., 2017, "Traditional versus 3' RNA-seq in a non-model species," Genom Data. 11:9-16, doi:10.1016/j.gdata.2016.11.002; and 10X Genomics, "What is the difference between Single Cell 3' and 5' Gene Expression libraries?" available on the internet at kb.10xgenomics.com/hc/en-us/articles/360000939852-What-is-the-difference-between-Single-Cell-3-and-5-Gene-Expression-libraries-, the entire contents of which are incorporated herein by reference.

PCR amplicon sequencing, another widely used approach for nucleic acid sequence analysis, allows for targeted expression analysis by performing PCR amplification on transcripts of interest, followed by next-generation sequencing of amplified target regions. PCR amplicon sequencing also suffers from limitations including high levels of duplicate reads, polymerase artifacts and PCR amplification bias, which can result in ambiguity during transcript quantification and require additional normalization steps to account for any statistical or experimental errors. See, Peng et al., 2015, "Reducing amplification artifacts in high multiplex amplicon sequencing by using molecular barcodes," BMC Genomics. 16(1):589, doi:10.1186/s12864-015-1806-8, the entire contents of which are incorporated herein by reference.

Thus, there is a need in the art for improved methods of enriching nucleic acid molecules for RNA sequencing. In particular, there is a need in the art for transcriptome-specific, high-fidelity enrichment of nucleic acid molecules for targeted sequencing.

SUMMARY

Technical solutions for addressing the above identified problems are provided in the present disclosure. Specifically, the present disclosure provides systems and methods for identifying and using hybridization and capture probes for full-length cDNA.

The disclosed systems and methods comprise obtaining cDNA sequences from poly-adenylated mRNA from a biological sample of a subject. Each cDNA sequence in a first subset maps to a gene in a plurality of genes, and each cDNA sequence in a second subset maps to a reference genome portion not represented by the plurality of genes. Each gene has a corresponding plurality of transcripts. The discloses systems and methods further comprise exposing the cDNA sequences to at least $2 \times 10^3$ nucleic acid baits between $K_1$ and $K_2$ residues long, forming nucleic acid bait—sequence read complexes, where each nucleic acid bait that hybridizes to a cDNA sequence mapping to a gene selectively hybridizes to a first subset of transcripts in a corresponding plurality of subsets of transcripts, or selectively hybridizes to another subset of transcripts, other than the first subset of transcripts, in the corresponding plurality of subsets of transcripts, corresponding to the gene. Each transcript of each gene is hybridizable to a nucleic acid bait in the at least $2 \times 10^3$ nucleic acid baits. The disclosed systems and methods further comprise selectively capturing and analyzing the nucleic acid bait—sequence read complexes.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

One aspect of the present disclosure provides a method comprising obtaining a plurality of cDNA sequences from a pool of poly-adenylated mRNA obtained from a biological sample of a subject, where the plurality of cDNA sequences comprise a first subset of cDNA sequences and a second subset of cDNA sequences, each respective cDNA sequence in the first subset of cDNA sequences maps to a respective gene in a plurality of genes, and each respective cDNA sequence in the second subset of cDNA sequences maps to a portion of a reference genome not represented by the plurality of genes. Each respective gene in the plurality of genes is characterized by a corresponding plurality of transcripts.

The method further comprises exposing the plurality of cDNA sequences to a plurality of nucleic acid baits each of length that is between $K_1$ and $K_2$ residues, thus forming a plurality of nucleic acid bait—sequence read complexes. The plurality of nucleic acid baits comprises at least $2 \times 10^3$ nucleic acid baits. Each respective nucleic acid bait in the plurality of nucleic acid baits that hybridizes to a cDNA sequence mapping to a respective gene in the plurality of genes selectively hybridizes to a first subset of transcripts, in a corresponding plurality of subsets of transcripts in the plurality of transcripts corresponding to the respective gene, or selectively hybridizes to another subset of transcripts, other than the first subset of transcripts, in the corresponding plurality of subsets of transcripts in the plurality of transcripts corresponding to the respective gene. Each respective transcript in the corresponding plurality of transcripts of each respective gene in the plurality of genes is hybridizable to a nucleic acid bait in the plurality of nucleic acid baits.

The method further comprises selectively capturing the plurality of nucleic acid bait—sequence read complexes and analyzing the plurality of nucleic acid bait—sequence read complexes captured by the selectively capturing.

In some embodiments, the analyzing the plurality of nucleic acid bait—sequence read complexes captured by the selectively capturing identifies one or more analytes in the biological sample.

In some embodiments, the selectively capturing the plurality of nucleic acid bait-sequence read complexes captures the plurality of nucleic acid bait—sequence read complexes to a solid support. In some embodiments, the solid support comprises a bead.

In some embodiments, each nucleic acid bait in the plurality of nucleic acid baits comprises a non-nucleotide binding moiety, the solid support comprises a plurality of capture moieties, and a respective nucleic acid bait—sequence read complex is captured on the solid support through a reaction between a capture moiety in the plurality of capture moieties and the corresponding binding moiety of the respective nucleic acid bait—sequence read complex. In some such embodiments, a capture moiety in the plurality of capture moieties comprises streptavidin and the corresponding non-nucleotide binding moiety comprises biotin, 2-(4-Hydroxyphenylazo)benzoic acid (HABA), or a compound listed in Table 1.

In some embodiments, each respective nucleic acid bait in the plurality of nucleic acid baits shares less than a threshold percentage of sequence identity to any other nucleic acid bait in the plurality of nucleic acid baits. In some such embodiments, the threshold percentage of sequence identity is ten percent, twenty percent, thirty percent, or between five and fifty percent.

In some embodiments, the pool of poly-adenylated mRNA is obtained from the biological sample by single cell 3' sequencing, single cell 5' sequencing, or single cell 5' paired-end sequencing.

In some embodiments, the plurality of cDNA sequences consists of the first subset of cDNA sequences and the second subset of cDNA sequences.

In some embodiments, the method further comprises filtering the plurality of nucleic acid baits for mappability, absence of repetitive subsequences, and/or overall GC content.

In some embodiments, the plurality of genes is between five genes and twenty thousand genes. In some embodiments, the plurality of transcripts corresponding to the respective gene comprises three or more transcripts for the respective gene. In some embodiments, the plurality of transcripts corresponding to the respective gene comprises five or more transcripts for the respective gene. In some embodiments, the first subset of transcripts consists of two or more transcripts. In some embodiments, the first subset of transcripts consists of three or more transcripts. In some embodiments, the first subset of transcripts consists of four or more transcripts. In some embodiments, the second subset of transcripts consists of two or more transcripts.

In some embodiments, the plurality of nucleic acid baits includes a minimum number of baits necessary to selectively hybridize to each respective transcript in the corresponding plurality of transcripts for a respective gene in the plurality of genes.

In some embodiments, the plurality of nucleic acid baits consists of a minimum number of baits necessary to selectively hybridize to each respective transcript in the corresponding plurality of transcripts for each respective gene in the plurality of genes.

In some embodiments, an analyte in the one or more analytes is associated with a disease or a condition. In some such embodiments, the method further comprises treating the subject for the disease or condition when it is determined from the one or more analytes that the subject has the disease or condition. In some embodiments, an analyte in the one or more analytes comprises a mutation. In some embodiments, an analyte in the one or more analytes comprises an alternative allele of a single nucleotide polymorphism (SNP). In some embodiments, the one or more analytes is a plurality of analytes. In some embodiments, the plurality of analytes is ten or more analytes.

In some embodiments, the plurality of cDNA sequences is at least $1 \times 10^6$ cDNA sequences. In some embodiments, the plurality of cDNA sequences is at least $1 \times 10^7$ cDNA sequences.

In some embodiments, the plurality of transcripts corresponding to the respective gene is each transcript of the respective gene annotated in GENCODE Release 33 (GRCh38.p 13).

In some embodiments, $K_1$ is 25 and $K_2$ is 1000. In some embodiments, $K_1$ is 50 and $K_2$ is 500. In some embodiments, $K_1$ is 90 and $K_2$ is 150. In some embodiments, $K_1$ is 95 and $K_2$ is 130. In some embodiments, $K_1$ is the same value of $K_2$. In some embodiments, $K_1$ is 100 or 120. In some embodiments, $K_1$ and $K_2$ are different positive integers.

In some embodiments, each respective substring of fixed length P nucleotides in each respective nucleic acid bait in the plurality of nucleic acid baits is represented in the reference genome less than a threshold number of times L. In some embodiments, P is at least 15 nucleotides. In some embodiments, P is at least 25 nucleotides. In some embodiments, L is between 2 and 50.

In some embodiments, each respective nucleic acid bait in the plurality of nucleic acid baits comprises a nucleic acid sequence that has a minimal identity to the reference genome of at least 90%.

In some embodiments, the corresponding plurality of transcripts of a respective gene in the plurality of genes comprises a plurality of isoforms of the respective gene. In some such embodiments, the plurality of isoforms of the respective gene comprises a first transcriptional isoform and a second transcriptional isoform of the respective gene.

In some embodiments, the method further comprises designing a nucleic acid bait in the plurality of nucleic acid baits for a respective gene in the plurality of genes using, when the length of the coding sequence of the respective gene satisfies a predetermined length threshold, the coding sequence of the respective gene, and when the length of the coding sequence of the respective gene does not satisfy a predetermined length threshold, an mRNA sequence of the respective gene.

In some embodiments, the method further comprises modifying a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L, where the modifying comprises (i) removing the respective nucleic acid bait from the plurality of nucleic acid baits, (ii) truncating the respective nucleic acid bait such that the respective nucleic acid bait is represented in the reference genome at a position that is at least M base pairs away from any portion of the reference genome that comprises the substring of fixed length P, or (iii) shifting the respective sequence of the nucleic acid bait along the reference genome such that the respective sequence of the nucleic acid bait is represented in the reference genome at a position that is at least M base pairs away from any portion of the reference genome that comprises the substring of fixed length P.

In some such embodiments, P is between 10 and 75. In some embodiments, P is between 20 and 50. In some embodiments, P is between 37 and 43. In some embodiments, L is between 2 and 1000. In some embodiments, L is between 5 and 500. In some embodiments, L is between 10 and 100. In some embodiments, L is between 20 and 50. In some embodiments, L is between 23 and 27.

In some embodiments, the analyzing the plurality of nucleic acid bait—sequence read complexes captured by the selectively capturing comprises sequencing of nucleic acid bait—sequence read complexes captured.

In some embodiments, each transcript in the plurality of transcripts corresponding to the respective gene is protein coding. In some embodiments, a transcript in the plurality of transcripts corresponding to the respective gene is coding sequence (CDS) 3' incomplete, CDS 5' incomplete, or both CDS 3' and 5' incomplete. In some embodiments, each transcript in the plurality of transcripts corresponding to the respective gene has GENCODE transcript support level 1. In some embodiments, each transcript in the plurality of transcripts corresponding to the respective gene has GENCODE transcript support level 1, GENCODE transcript support level 2, or GENCODE transcript support level 3.

In another aspect, the present disclosure provides a method of identifying a plurality of at least $2\times10^3$ nucleic acid baits. The method comprises, for each respective gene in a plurality of genes, obtaining a respective candidate hybridization sequence of the respective gene, where, when a length of the coding sequence of the respective gene satisfies a predetermined length threshold, the candidate hybridization sequence is the coding sequence of the respective gene, and when the length of the coding sequence of the respective gene does not satisfy a predetermined length threshold, the candidate hybridization sequence is an mRNA sequence of the respective gene. The method comprises obtaining a corresponding plurality of transcripts for the respective gene.

In this aspect, the method further comprises, for each respective sub-sequence of length K residues of the respective candidate hybridization sequence, determining a count of a number of transcripts in the corresponding plurality of transcripts the respective sub-sequence matches, thus determining a corresponding first sub-sequence that matches a first maximal number of transcripts in the corresponding plurality of transcripts, where the transcripts in the corresponding plurality of transcripts that match the first sub-sequence define a corresponding first subset of transcripts, in a corresponding plurality of subsets of transcripts within the corresponding plurality of transcripts.

The method further comprises, for each respective sub-sequence of length K residues of the respective candidate hybridization sequence, determining a count of a number of transcripts in the corresponding plurality of transcripts, other than those transcripts in the corresponding first subset of transcripts, the respective sub-sequence matches, thus determining a corresponding second sub-sequence that matches a second maximal number of transcripts in the corresponding plurality of transcripts other than those transcripts in the corresponding first subset of transcripts, where the transcripts in the corresponding plurality of transcripts that match the second sub-sequence define a corresponding second subset of transcripts, in the corresponding plurality of subsets of transcripts within the corresponding plurality of transcripts.

The method further comprises including a nucleic acid bait corresponding to the corresponding first sub-sequence in the plurality of nucleic acid baits, and including a nucleic acid bait corresponding to the corresponding second sub-sequence in the plurality of nucleic acid baits.

In some embodiments, when the corresponding first subset of transcripts and the corresponding second subset of transcripts fail to account for all the transcripts in the corresponding plurality of transcripts, the method further comprises, for each respective sub-sequence of length K residues of the respective candidate hybridization sequence, determining a count of a number of transcripts in the corresponding plurality of transcripts, other than those transcripts in the corresponding first or second subset of transcripts, the respective sub-sequence matches, thus determining a corresponding third sub-sequence that matches a third maximal number of transcripts in the corresponding plurality of transcripts, other than those transcripts in the corresponding first and second subset of transcripts, where the transcripts in the corresponding plurality of transcripts that match the third sub-sequence define a corresponding third subset of transcripts, in the corresponding plurality of subsets of transcripts within the corresponding plurality of transcripts, and including a nucleic acid bait corresponding to the corresponding third sub-sequence in the plurality of nucleic acid baits.

In some embodiments, the method further comprises obtaining a plurality of cDNA sequences from a pool of poly-adenylated mRNA obtained from a biological sample of a subject, where the plurality of cDNA sequences comprises a first subset of cDNA sequences and a second subset of cDNA sequences. Each respective cDNA sequence in the first subset of cDNA sequences maps to a respective gene in a plurality of genes, and each respective cDNA sequence in the second subset of cDNA sequences maps to a portion of a reference genome not represented by the plurality of genes. In such embodiments, the method further comprises exposing the plurality of cDNA sequences to the plurality of nucleic acid baits, thus forming a plurality of nucleic acid bait—sequence read complexes, selectively capturing the plurality of nucleic acid bait—sequence read complexes, and analyzing the plurality of nucleic acid bait—sequence read complexes captured by the selectively capturing.

In some embodiments, K is between 25 and 1000. In some embodiments, K is between 50 and 500. In some embodiments, K is between 90 and 150. In some embodiments, K is between 95 and 130. In some embodiments, K is 100 or 120.

In some embodiments, the method further comprises modifying a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L, by (i) removing the respective nucleic acid bait from the plurality of nucleic acid baits, (ii) truncating the respective nucleic acid bait such that the respective nucleic acid bait is represented in the reference genome at a position that is at least M base pairs away from any portion of the reference genome that comprises the substring of fixed length P, or (iii) shifting the respective sequence of the nucleic acid bait along the reference genome such that the respective sequence of the nucleic acid bait is represented in the reference genome at a position that is at least M base pairs away from any portion of the reference genome that comprises the substring of fixed length P.

In some embodiments, the analyzing the plurality of nucleic acid bait—sequence read complexes captured by the selectively capturing comprises sequencing of nucleic acid bait—sequence read complexes captured.

In some embodiments, the determining a count of a number of transcripts in the corresponding plurality of transcripts the respective sub-sequence matches is performed using a native string-search algorithm using a computer system comprising a processor coupled to a non-transitory memory.

In some embodiments, the determining a count of a number of transcripts in the corresponding plurality of transcripts the respective sub-sequence matches is performed using a naïve string search, a finite-state-automaton-based search, a Rabin-Karp algorithm, a Knuth-Morris-Pratt algorithm, a Boyer-Moore string-search algorithm, a two-way string-matching algorithm, or a backward non-deterministic directed acyclic word graph matching algorithm using a computer system comprising a processor coupled to a non-transitory memory.

In some embodiments, the determining a count of a number of transcripts in the corresponding plurality of transcripts the respective sub-sequence matches has a matching time of $Q*O(KM)$, wherein M is an average length of the corresponding plurality of transcripts, and Q is a number of transcripts in the corresponding plurality of transcripts, using a computer system comprising a processor coupled to a non-transitory memory.

In another aspect, the present disclosure provides a computer system comprising one or more processors, memory, and one or more programs, where the one or more programs are stored in the memory and configured to be executed by the one or more processors, the one or more programs for identifying a plurality of at least $2 \times 10^3$ nucleic acid baits. In this aspect, the one or more programs include instructions for obtaining, in electronic form, a respective candidate hybridization sequence of the respective gene. When a length of the coding sequence of the respective gene satisfies a predetermined length threshold, the candidate hybridization sequence is the coding sequence of the respective gene, and when the length of the coding sequence of the respective gene does not satisfy a predetermined length threshold, the candidate hybridization sequence is an mRNA sequence of the respective gene. The one or more programs further include instructions for obtaining, in electronic form, a corresponding plurality of transcripts for the respective gene.

The one or more programs further include instructions for, for each respective sub-sequence of length K residues of the respective candidate hybridization sequence, determining a count of a number of transcripts in the corresponding plurality of transcripts the respective sub-sequence matches, thus determining a corresponding first sub-sequence that matches a first maximal number of transcripts in the corresponding plurality of transcripts, where the transcripts in the corresponding plurality of transcripts that match the first sub-sequence define a corresponding first subset of transcripts, in a corresponding plurality of subsets of transcripts within the corresponding plurality of transcripts.

The one or more programs further include instructions for, for each respective sub-sequence of length K residues of the respective candidate hybridization sequence, determining a count of a number of transcripts in the corresponding plurality of transcripts, other than those transcripts in the corresponding first subset of transcripts, the respective sub-sequence matches, thus determining a corresponding second sub-sequence that matches a second maximal number of transcripts in the corresponding plurality of transcripts other than those transcripts in the corresponding first subset of transcripts, where the transcripts in the corresponding plurality of transcripts that match the second sub-sequence define a corresponding second subset of transcripts, in the corresponding plurality of subsets of transcripts within the corresponding plurality of transcripts.

The one or more programs further include instructions for including a nucleic acid bait corresponding to the corresponding first sub-sequence in the plurality of nucleic acid baits, and including a nucleic acid bait corresponding to the corresponding second sub-sequence in the plurality of nucleic acid baits.

In some embodiments, the one or more programs executed by the one or more processors include instructions for performing any of the methods, embodiments, and any substitutions, modifications, and/or combinations thereof, as will be apparent to one skilled in the art.

In another aspect, the present disclosure provides a computer readable storage medium storing one or more programs, the one or more programs comprising instructions, which when executed by an electronic device with one or more processors and a memory cause the electronic device to identify a plurality of at least $2 \times 10^3$ nucleic acid baits by a method. In this aspect, the method comprises obtaining, in electronic form, a respective candidate hybridization sequence of the respective gene, where, when a length of the coding sequence of the respective gene satisfies a predetermined length threshold, the candidate hybridization sequence is the coding sequence of the respective gene, and when the length of the coding sequence of the respective gene does not satisfy a predetermined length threshold, the candidate hybridization sequence is an mRNA sequence of the respective gene. The method comprises obtaining, in electronic form, a corresponding plurality of transcripts for the respective gene.

The method further comprises, for each respective sub-sequence of length K residues of the respective candidate hybridization sequence, determining a count of a number of transcripts in the corresponding plurality of transcripts the respective sub-sequence matches, thus determining a corresponding first sub-sequence that matches a first maximal number of transcripts in the corresponding plurality of transcripts, where the transcripts in the corresponding plurality of transcripts that match the first sub-sequence define a corresponding first subset of transcripts, in a corresponding plurality of subsets of transcripts within the corresponding plurality of transcripts.

The method further comprises, for each respective sub-sequence of length K residues of the respective candidate hybridization sequence, determining a count of a number of transcripts in the corresponding plurality of transcripts, other than those transcripts in the corresponding first subset of transcripts, the respective sub-sequence matches, thus determining a corresponding second sub-sequence that matches a second maximal number of transcripts in the corresponding plurality of transcripts other than those transcripts in the corresponding first subset of transcripts, where the transcripts in the corresponding plurality of transcripts that match the second sub-sequence define a corresponding second subset of transcripts, in the corresponding plurality of subsets of transcripts within the corresponding plurality of transcripts.

The method further comprises including a nucleic acid bait corresponding to the corresponding first sub-sequence in the plurality of nucleic acid baits, and including a nucleic acid bait corresponding to the corresponding second sub-sequence in the plurality of nucleic acid baits.

In some embodiments, the one or more programs stored in the computer readable storage medium include instructions for performing any of the methods, embodiments, and any substitutions, modifications, and/or combinations thereof, as will be apparent to one skilled in the art.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 2A, 2B, 2C, and 2D collectively provide an overview of a method for capturing targeted transcriptomes using a hybridization/capture approach, in which optional steps are indicated by dashed boxes, in accordance with some embodiments of the present disclosure.

FIGS. 3A, 3B, and 3C collectively provide an overview of a method for identifying a plurality of nucleic acid baits, in which optional steps are indicated by dashed boxes, in accordance with some embodiments of the present disclosure.

FIGS. 4A and 4B illustrate a plurality of unfragmented full-length cDNA molecules and a plurality of nucleic acid library fragments, respectively, for a genetic target, in accordance with some embodiments of the present disclosure.

FIG. 6 illustrates an example workflow for hybridization and capture-based enrichment of targeted nucleic acid sequences using a 3' gene expression library, in accordance with some embodiments of the present disclosure.

DETAILED DESCRIPTION

Figure 1:
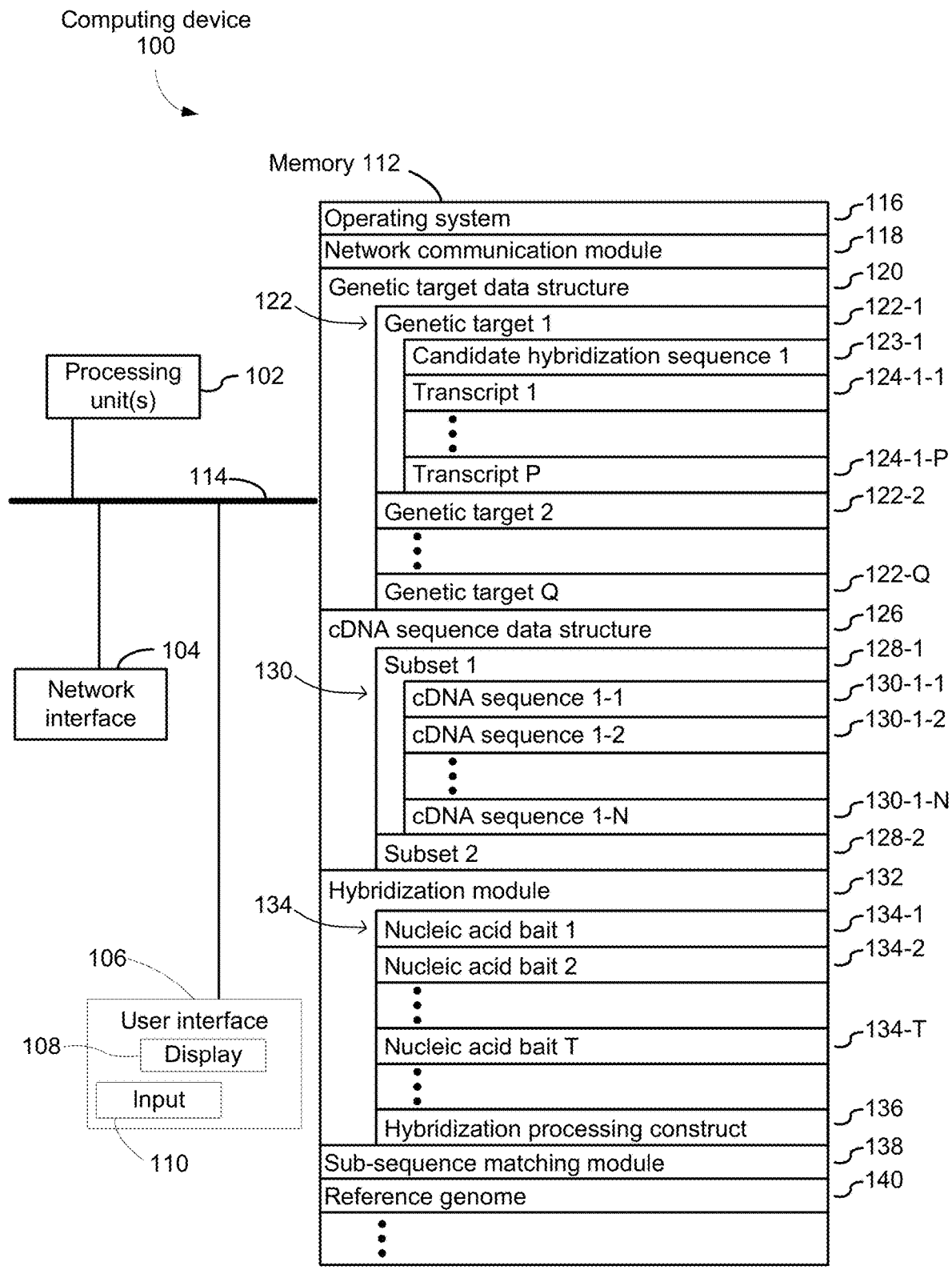
FIG. 1 is an example block diagram illustrating a computing device 100 for designing and using hybridization/capture probes, in accordance with some embodiments of the present disclosure.
Figure 2D:
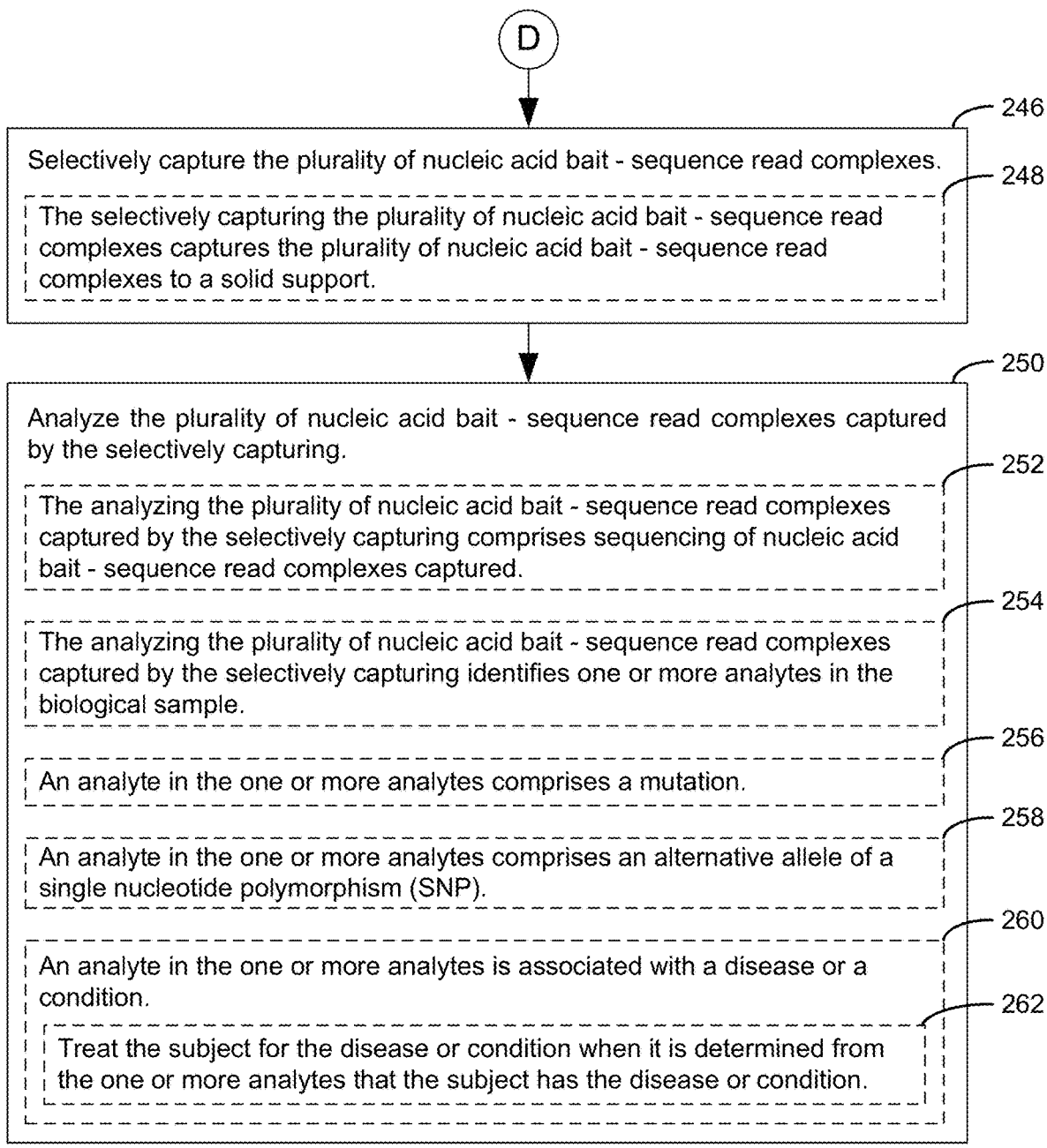
Figure 3A:
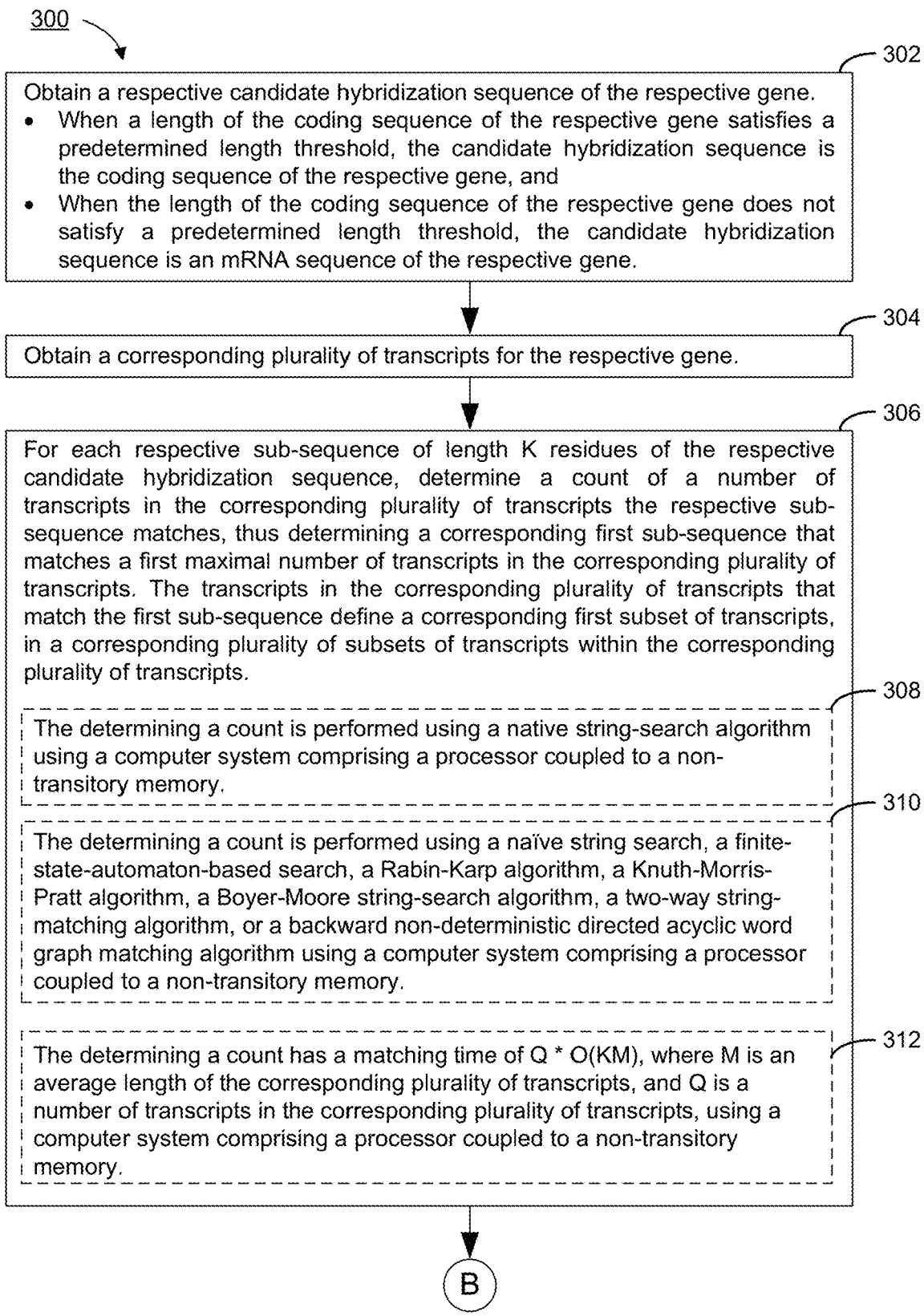
Figure 3C:
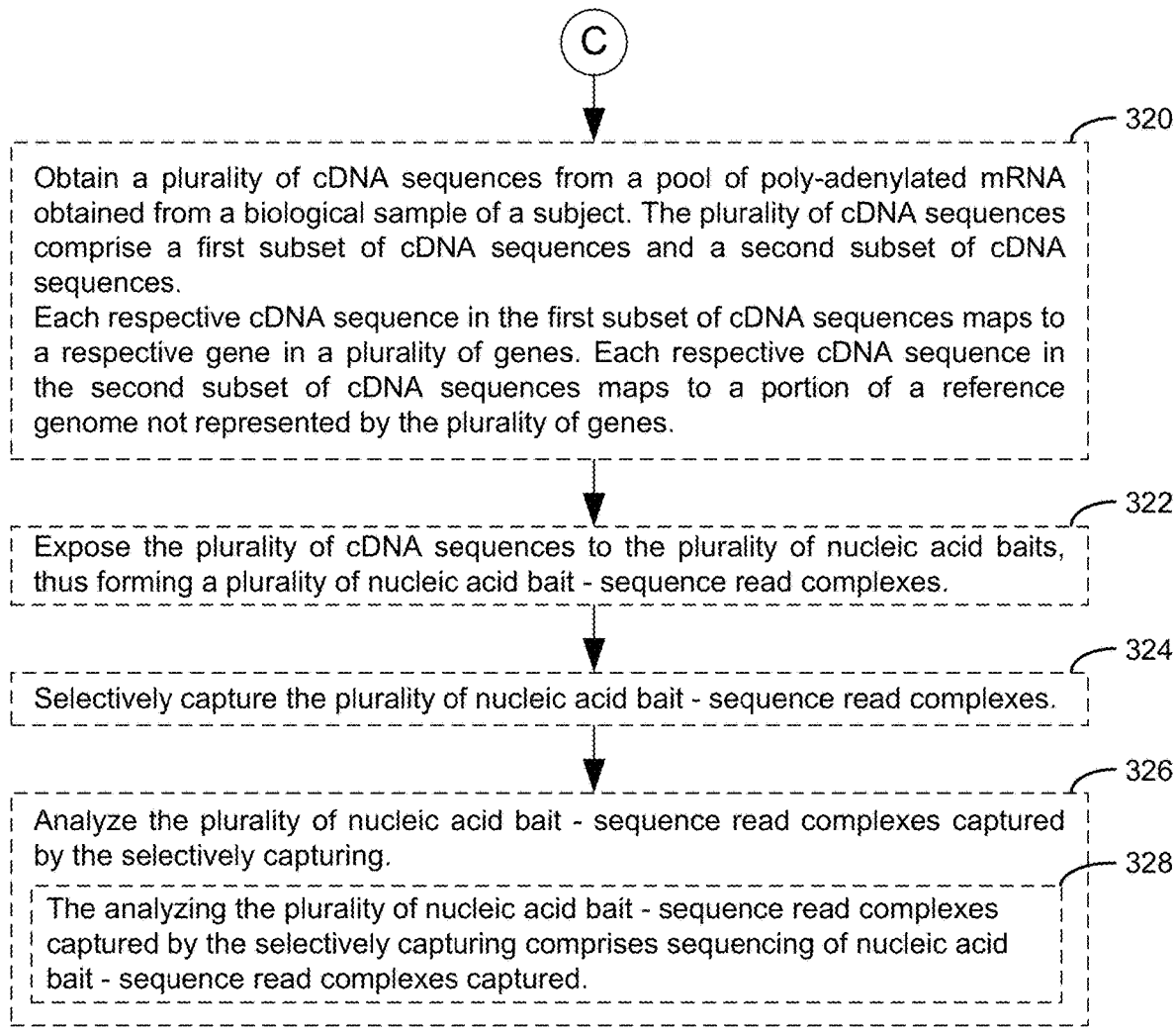

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

INTRODUCTION

Targeted applications of sequence reads including, among others, single cell RNA sequencing, bulk RNA sequencing, and/or next-generation sequencing, comprise inherent limitations due to the lack of accurate and comprehensive annotations at the terminal ends of nucleic acid molecules. For example, some traditional methods of preparing gene expression libraries for sequencing analysis involve fragmenting cDNA molecules obtained from reverse-transcribed, poly-adenylated mRNA and selecting for fragments containing the 3' or 5' ends of the cDNA molecules using a PCR amplification step (e.g., using PCR primers that are complementary to one or more terminal regions ligated or added onto the 3' or 5' ends of the cDNA molecules). See, 10X Genomics, "What is the difference between Single Cell 3' and 5' Gene Expression libraries?" available on the internet at kb.10xgenomics.com/hc/en-us/articles/360000939852-What-is-the-difference-between-Single-Cell-3-and-5-Gene-Expression-libraries-. An exemplary sequencing library is illustrated in FIG. 4B, in which a plurality of sequencing library fragments 410 correspond exactly to the 3' and 5' ends of a full-length cDNA molecule 402. In some such applications, sequencing libraries comprising either 3' or 5' end fragments are sequenced to obtain a complete profile of gene expression in a biological sample of interest.

In some instances, however, targeted enrichment of a sequencing library is desired. Targeted enrichment allows for the isolation and sequencing of specific subsets of genes and/or regions of the genome, thus limiting downstream analysis (and any associated costs, time, and/or labor) only to those genes that are relevant to the particular research query under investigation. In some such implementations, enrichment of the gene or genes of interest (e.g., a gene panel) is performed using a hybridization and capture approach. First, gene expression libraries are exposed to a plurality of nucleic acid baits that are designed to hybridize to target genes, thus forming a plurality of nucleic acid bait—target sequence complexes. Second, the nucleic acid bait—target sequence complexes are captured onto one or more solid supports (e.g., capture beads) via an interaction between a first binding moiety (e.g., biotin) attached to the nucleic acid bait and a second binding moiety (e.g., streptavidin) attached to the solid support. Captured target sequences are then isolated (e.g., by washing the solid support to remove unbound baits and/or unbound gene expression library fragments), amplified (e.g., by PCR), and sequenced to obtain a gene expression profile of the target genes.

An example workflow of the above hybridization and capture approach using a conventional 3' gene expression library is illustrated in FIG. 6. In such embodiments, the plurality of nucleic acid baits must be designed such that they hybridize to the 3' ends (or 5' ends, where applicable) of the genes of interest in order to provide good coverage of the target genes and thus accurately represent the gene expression profile in the biological sample.

One limitation with this approach is that the 3' untranslated regions (UTRs) of many genes, of which conventional 3' gene expression libraries are composed, are often poorly annotated. For example, due to poor annotations, an annotated UTR may be longer or shorter than the true length of the UTR. In other words, whereas FIG. 4B illustrates an exemplary sequencing library comprising a plurality of fragments 410 corresponding to the ends of a respective cDNA molecule 402, in many instances the true 3' and 5' ends of the respective cDNA molecule may be located at a different genomic location than is indicated by available annotations.

As a result, the design of nucleic acid baits for hybridization to the 3' ends of target genes based on 3' UTR annotations will, in many cases, be hindered by the lack of accurate and comprehensive annotations as to the true location of the 3' UTRs. Subsequent implementation of the hybridization and capture approach using nucleic acid baits designed in this manner can result in poor quality coverage of target genes.

For example, an inaccurate, partial, or missing annotation of the 3' UTR of a target gene can result in the design of a nucleic acid bait that is hybridizable to a region of the target gene or reference genome outside (e.g., upstream or downstream) of the actual sequencing library fragment, such that any fragments corresponding to the respective gene will not be captured. Alternatively, a missing annotation for one or more transcripts (e.g., isoforms) at the 3' UTR of a target gene can result in the design of a nucleic acid bait that is hybridizable to a first transcript but not a second transcript of the respective gene, such that only a subset of fragments corresponding to the respective gene will be captured.

One solution to this limitation is to "tile" nucleic acid baits across the entire length of the target gene to obtain at least a 1× coverage of every position in the gene (e.g., an average of one bait per base pair). This solution ensures that the plurality of library fragments corresponding to each target gene will be captured, regardless of where they are located relative to their 3' UTR annotations. Using this solution, it would also be possible to generate nucleic acid baits that hybridize to each transcript (e.g., isoform) in a plurality of transcripts for a respective target gene, by making use of the more reliable annotations located farther away from the 3' UTR. However, a method of "tiling" nucleic acid baits across the length of a target gene becomes increasingly inefficient and often prohibitively expensive for users desiring large targeted gene panels (e.g., off-panel genes or custom panels), due to the large number of probes required to ensure a 1× coverage of every gene (e.g., 38,000-65,000 nucleic acid baits for a 1000 gene panel).

Thus, there is a need in the art for a method that provides for the design of hybridization and capture probes that can be used for the accurate enrichment of target genes while reducing cost, maximizing efficiency, and minimizing redundancy. Such a method would improve and focus experimental design and increase user capacity for a greater number of assays.

Another difficulty encountered when designing and generating nucleic acid baits for full-length cDNA is the likelihood of obtaining truncated, intronic, and/or anti-sense nucleic acid fragments during the generation (e.g., reverse transcription and amplification) of cDNA from mRNA fragments. For instance, while single-cell gene expression data primarily includes reads mapped to exonic regions derived from mature spliced transcripts, reads that map entirely or partially to intronic regions and strand-specific antisense reads have also been observed. Thus, in some implementations, not all transcripts for a respective gene are represented in a gene expression library as a full-length cDNA molecule. Without being limited to any one theory of operation, the presence of truncated, intronic, and anti-sense nucleic acid fragments in gene expression libraries may be attributed to internal priming and/or to premature template switching by template switching oligonucleotides (TSOs), for instance via internal poly-A priming in single-cell 3' assays, TSO priming in single-cell 3' and 5' assays, poly(dT) primer strand invasion in single-cell 3' assays, first-strand cDNA priming in single-cell 3' and 5' assays, and/or sense-antisense fusion in single-cell 3' and 5' assays. See, for example, 10X Genomics, 2020, "Technical Note—Interpreting Intronic and Antisense Reads in Single Cell Gene Expression Data", Document Number CG000376, Rev A, which is hereby incorporated herein by reference in its entirety.

For example, in typical single-cell 3' assays, a poly(dT) primer (e.g., including a barcode and unique molecular identifier (UMI)) enables the production of barcoded, full-length cDNA by priming off the poly-adenylated (poly-A) mRNA tail. In contrast, internal poly-A priming in single-cell 3' assays can occur when the poly(dT) primer primes an internal poly-A stretch in the mRNA instead of the poly-A tail, resulting in a sense read pair located internally rather than at the end of the transcript. In some embodiments, this mechanism results in reads occurring on exons or introns, although there are ~21.2 times as many poly-A stretches in introns compared to exons in the human genome and they occur at a rate ~1.7 times as large in introns compared to exons (counted as stranded, non-overlapping poly-A 7-mers).

Antisense reads can also be potentially generated by aberrant template switching oligonucleotide (TSO) priming at homologous sites on the RNA in single-cell 3' and 5' assays. Such priming can occur by an isolated TSO or an oligo (e.g., a gel bead oligo) that includes the TSO, a barcode, and a UMI, resulting, in either case, in amplifiable cDNA capable of producing both sense and antisense reads. In single-cell 3' assays, an intermolecular template switch event from a poly-T stretch on the RNA to a poly-T stretch in the primer with barcode and UMI can result in an amplifiable antisense molecule. There are ~25.1 times as many poly-T stretches in introns compared to exons in the human genome and they occur at a rate ~2.0 times as large in introns compared to exons (counted as stranded, non-overlapping poly-T 7-mers).

Poly(dT) primer strand invasion in single-cell 3' assays can occur when first-strand cDNA synthesis is initiated normally or at an internal poly-A site but is interrupted by an intermolecular template switch from a poly-T stretch on the mRNA to the poly-T stretch on an oligo (e.g., a gel bead oligo including a barcode and a UMI). As a result, an amplifiable cDNA with distinct UMIs on each end may be formed that is capable of generating both sense and antisense reads. If this occurs simultaneously with internal priming, multiple sense and antisense UMIs could be generated from distinct poly-A and poly-T sites on the same molecule. Additionally, first-strand cDNA priming in single-cell 3' and 5' assays can occur when, after reverse transcription, RNA is degraded or compromised, leaving the first-strand-cDNA exposed. The poly(dT) primer priming off a poly-A stretch on the cDNA can result in a cDNA with a sense barcode and UMI on one end and an antisense barcode and UMI on the other end. Since the barcode and UMIs on both ends include PCR primers, the construct can be amplified, fragmented, and sequenced and the antisense side of the construct can result in antisense read pairs.

Mechanisms that produce sense-antisense fusion cDNAs in 3' and 5' assays have been proposed as a source of antisense artifacts. After first strand cDNA synthesis, if the RNA is degraded or the RNA-cDNA duplex is compromised, the cDNA can potentially form a hair-pin loop with itself at a short reverse-complementary motif and self-prime to create a hairpin cDNA molecule that is a fusion between sense and antisense sequences. At the initiation of PCR, the fusion molecule can denature, and the second strand cDNA can be completed. This molecule can be amplified and fragmented generating an antisense read pair. Truncated, intronic, and anti-sense reads in single-cell expression data are further described in 10X Genomics, 2020, "Technical Note—Interpreting Intronic and Antisense Reads in Single Cell Gene Expression Data", Document Number CG000376, Rev A, which is hereby incorporated herein by reference in its entirety.

Regardless of the underlying mechanism, the presence of truncated, intronic, and anti-sense nucleic acid fragments in gene expression libraries gives rise to additional obstacles when generating nucleic acid baits targeting genes of interest, particularly when generating reduced (e.g., minimal) nucleic acid bait sets. Given the possibility that a respective gene will be represented in the gene expression library in a truncated, intronic, or anti-sense form, it is often the case that bait sets designed to adequately maximize the capture and recovery of all transcripts for the respective gene include multiple nucleic acid baits to cover all possible sequences arising from a given mRNA molecule for the gene. Thus, there is a need in the art for methods of generating reduced (e.g., minimal) nucleic acid bait sets that maximize the capture and recovery of all transcripts for a respective gene.

Benefit

Figure 8A:
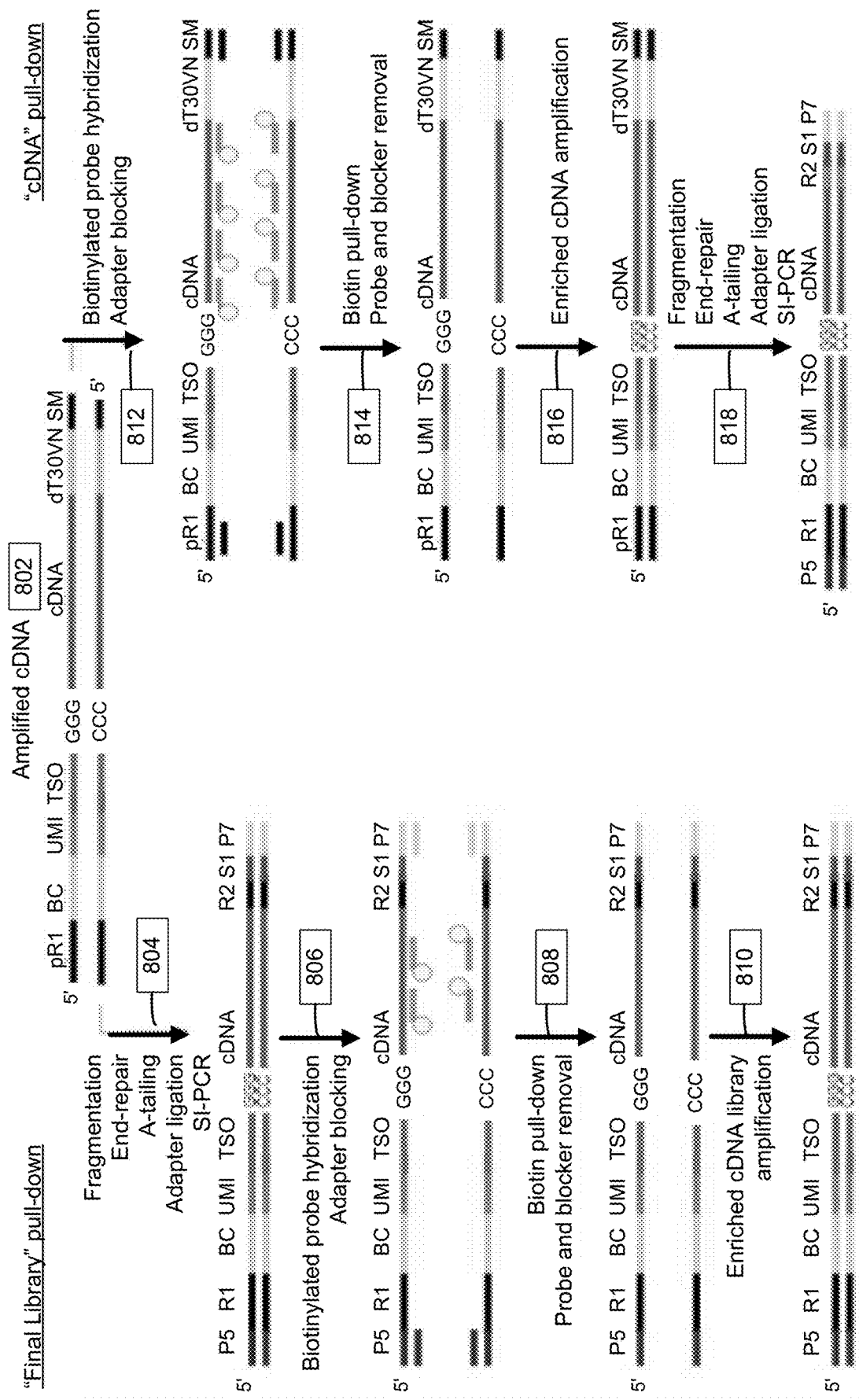
FIGS. 8A and 8B illustrate two example workflows for obtaining gene expression libraries with nucleic acid baits using a hybridization/capture approach, in accordance with some embodiments of the present disclosure.
Figure 8B:
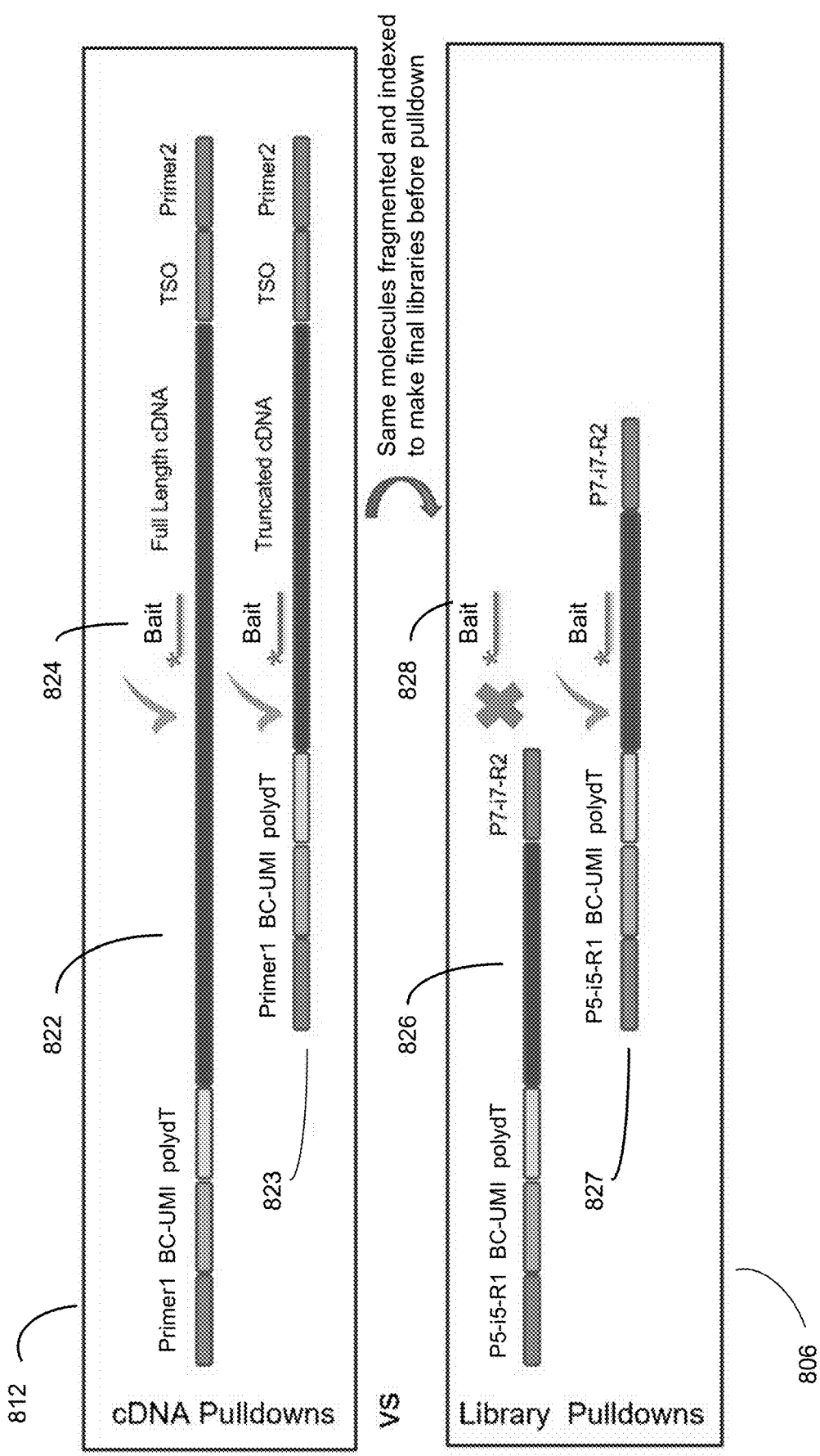

Advantageously, provided herein is a method that comprises designing and using probes (e.g., nucleic acid baits) to capture full-length (e.g., unfragmented) cDNA for sequencing analysis, rather than probes for capturing final library fragments encompassing 3' UTRs. By targeting full-length cDNA, it is possible to utilize the more reliably annotated regions of the target gene, such as coding sequences, for each transcript (e.g., isoform) of the respective gene. For example, FIG. 4A illustrates a plurality of unfragmented, full-length cDNA molecules 404 generated by PCR amplification of a cDNA target sequence 402. In contrast to the poorly annotated 3' UTR 408, the coding sequence 406 likely comprises more accurate annotations and can be used for probe design in accordance with some embodiments of the present disclosure, thus ensuring improved coverage and a reduction in extraneous bait design compared to baits 410 designed based on 3' and 5' UTR annotations, as illustrated in FIG. 4B. Captured cDNA sequences can be isolated, amplified, and/or otherwise processed for subsequent analysis, such as fragmentation and sequencing library preparation. Furthermore, as illustrated in FIGS. 8A and 8B, the present disclosure provides, in some aspects, a plurality of nucleic acid baits used for cDNA hybridization and capture prior to cDNA fragmentation and library preparation. The use of unfragmented cDNA for hybridization and capture improves the capacity to design and generate nucleic acid baits that hybridize to a plurality of transcripts corresponding to a respective gene, due to the higher likelihood of overlapping sequences in unfragmented cDNA sequences (FIG. 8A). In contrast, fragmented cDNA sequences in "final libraries" such as those obtained by conventional single-cell 3' gene expression library preparation methods (as illustrated in FIGS. 6 and 8B) include relatively short fragments of cDNA, which are less likely to have overlapping sequences and thus may use much higher numbers of nucleic acid baits for comprehensive pull-down.

The present disclosure provides a method to design nucleic acid baits for full-length cDNA comprising obtaining a coding sequence for each transcript (e.g., isoform) of each target gene in a targeted gene panel. Where the coding sequence is less than a threshold length (e.g., 120 base pairs), a full mRNA sequence can be used instead. The method further comprises, for each 120 base pair subsequence in each coding sequence, obtaining a count of the number of transcripts in which the 120 base pair subsequence occurs. Each sub-sequence is ranked by the obtained count and a first sub-sequence is selected from the sub-sequence that occurs in the maximal number of transcripts for the respective gene. The first sub-sequence is further subjected to filtering criteria (e.g., uniqueness, mappability, absence of repetitive subsequences, and/or overall GC content). In some embodiments, if the first sub-sequence fails to satisfy one or more filtering criteria, the first sub-sequence is rejected and a new first sub-sequence is selected from the sub-sequence that occurs in the maximal number of transcripts for the respective gene that further satisfies the filtering criteria. In some embodiments, if the first sub-sequence fails to satisfy one or more filtering criteria, the first sub-sequence is modified (e.g., by truncating the first sub-sequence such that it satisfies the one or more filtering criteria and/or by shifting the first sub-sequence along the reference genome such that it satisfies the one or more filtering criteria).

The method further comprises selecting a second sub-sequence from the sub-sequence that occurs in the maximal number of remaining transcripts for the respective gene (e.g., other than the transcripts in which the first sub-sequence occurred). The method is iterated for all remaining transcripts until no transcripts remain (e.g., at least one sub-sequence in the plurality of selected sub-sequence occurs in each transcript in the plurality of transcripts for the target gene).

The method provided in the present disclosure improves upon the current technology by utilizing full-length cDNA sequences rather than 3' fragmented sequencing libraries, allowing access to larger regions of reliably annotated sequences for nucleic acid bait design. For example, full-length cDNA sequences comprise coding sequences, which are generally well-annotated, ensuring better pull-down results and on-target rates. Furthermore, full-length cDNA sequences include common sequences shared across transcripts (e.g., isoforms), allowing the design of nucleic acid baits that can target multiple transcripts and reducing the number of nucleic acid baits required by 10-fold. The resulting plurality of nucleic acid baits can thus be downsized and streamlined, leading to higher efficiency and reduced costs for users desiring nucleic acid baits for large and/or custom targeted gene panels. As an example, whereas a plurality of nucleic acid baits conventionally "tiled" for 1× coverage of a 1000-gene panel would comprise between 38,000 and 68,000 nucleic acid baits, a plurality of nucleic acid baits designed using the presently disclosed method for the same 1000-gene panel would comprise between 2,500 and 4,000 nucleic acid baits. Furthermore, the presently disclosed method can be performed for any application in which targeted analysis is desired (e.g., single cell RNA sequencing and/or spatial gene expression profiling).

Definitions

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(A) General Definitions

Nucleic Acid and Nucleotide.

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

Probe and Target.

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

Oligonucleotide and Polynucleotide.

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). An oligonucleotide can be 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

Genome.

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

Hybridizing and Hybridize.

The terms "hybridizing" and "hybridize" are used interchangeably in this disclosure and refer to the pairing of substantially complementary or complementary nucleic acids within two different molecules. Pairing can be achieved by any process in which a nucleic acid sequence joins with a substantially or fully complementary sequence through base pairing to form a hybridization complex. In some embodiments, pairing can occur by physical or computational means. For purposes of hybridization, two nucleic acid sequences are "substantially complementary" if at least 80% of their individual bases are complementary to one another.

Nucleic Acid Analytes and Sequence Reads.

The apparatus, systems, methods, and compositions described in this disclosure can be used to detect and analyze a wide variety of different analytes. For the purpose of this disclosure, an "analyte" includes any biological substance, structure, moiety, or component to be analyzed. The term "target" can similarly refer to an analyte of interest. The terms "nucleic acid analyte," "nucleic acid analytes,"

"sequence read," and "sequence reads" are used interchangeably in this disclosure.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Nucleic acid analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The generated cDNA can then be barcoded using a capture probe, featuring a barcode sequence (and optionally, a unique molecular identifier (UMI) sequence) that hybridizes with at least a portion of the generated cDNA. In some embodiments, a template switching oligonucleotide hybridizes to a poly(C) tail added to a 3' end of the cDNA by a reverse transcriptase enzyme. The original mRNA template and template switching oligonucleotide can then be denatured from the cDNA and the barcoded capture probe can then hybridize with the cDNA and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, filed Oct. 18, 2017, and U.S. patent application Ser. No. 15/825,740, filed Nov. 29, 2017, both of which are incorporated herein by reference in their entireties. V(D)J analysis can also be completed with the use of one or more labelling agents that bind to particular surface features of immune cells and associated with barcode sequences. The one or more labelling agents can include an MHC or MHC multimer.

As described above, the nucleic acid analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the nucleic acid analyte (e.g., a sequence that can hybridize to the CRISPR RNA (crRNA), single guide RNA (sgRNA), or an adapter sequence engineered into a crRNA or sgRNA).

Additional examples of analytes include mRNA and cell surface features, mRNA and intracellular proteins (e.g., transcription factors), mRNA and cell methylation status, mRNA and accessible chromatin (e.g., ATAC-seq, DNase-seq, and/or MNase-seq), mRNA and metabolites, a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein).

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample or can be obtained at intervals from a sample that continues to remain in viable condition.

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100 or more different analytes present in a region of the sample or within an individual feature of the substrate. Methods for performing multiplexed assays to analyze two or more different analytes are described in further detail in U.S. Provisional Patent Application No. 62/839,346 entitled "SPATIAL TRANSCRIPTOMICS OF BIOLOGICAL ANALYTES IN TISSUE SAMPLES," filed Apr. 26, 2019, which is hereby incorporated herein by reference.

Biological Samples.

A "biological sample" is obtained from the subject for analysis using any of a variety of techniques including, but not limited to, biopsy, surgery, and laser capture microscopy (LCM), and generally includes cells and/or other biological material from the subject. In addition to the subjects described above, a biological sample can also be obtained from a prokaryote such as a bacterium, e.g., *Escherichia coli*, Staphylococci orMycoplasma *pneumoniae*; an archae; a virus such as Hepatitis C virus or human immunodeficiency virus; or a viroid. A biological sample can also be obtained from a eukaryote, such as a patient derived organoid (PDO) or patient derived xenograft (PDX). Subjects from which biological samples can be obtained can be healthy or asymptomatic individuals, individuals that have or are suspected of having a disease (e.g., a patient with a disease such as cancer) or a pre-disposition to a disease, and/or individuals that are in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

Reference Genome.

As disclosed herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

Additional details on general definitions are provided in U.S. Provisional Patent Application No. 62/839,346 entitled "SPATIAL TRANSCRIPTOMICS OF BIOLOGICAL ANALYTES IN TISSUE SAMPLES," filed Apr. 26, 2019, which is hereby incorporated herein by reference in its entirety.

(B) Methods Definitions

Selective Enrichment of RNA Species.

In some embodiments, where RNA is the nucleic acid analyte or sequence that is read, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity (e.g. a probe) to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads). Other non-nucleic acid affinity moieties are known in the art, for example, 2-(4-Hydroxyphenylazo)benzoic acid (HABA) or a compound listed in Table 1.

TABLE 1

Affinity Moieties

| Compound | —COO— Position | R1 | R2 |
|---|---|---|---|
| HABA | ortho | H | H |
| 1b | meta | H | H |
| 1c | para | H | H |
| 2b | meta | H | NO$_2$ |
| 2c | para | H | NO$_2$ |
| 4a | ortho | CH$_3$ | CH$_3$ |
| 4b | meta | CH$_3$ | CH$_3$ |
| 4c | para | CH$_3$ | CH$_3$ |
| 5a | ortho | H | OH |
| 5b | meta | H | OH |
| 5c | para | H | OH |
| 6b | meta | OH | CH$_3$ |
| 6c | para | OH | CH$_3$ |

| Compound | —COO— Position |
|---|---|
| 3a | ortho |
| 3b | meta |
| 3c | para |

TABLE 1-continued

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved capture of other types of RNA due to the reduction in non-specific RNA present in the sample.
Processing Nucleic Acid Analytes in Biological Samples.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample.

In some embodiments, the sample can be treated with one or more enzymes. For example, one or more endonucleases to fragment DNA, DNA polymerase enzymes, and dNTPs used to amplify nucleic acids can be added. Other enzymes that can also be added to the sample include, but are not limited to, polymerase, transposase, ligase, and DNAse, and RNAse.

In some embodiments, reverse transcriptase enzymes can be added to the sample, including enzymes with terminal transferase activity, primers, and switch oligonucleotides. Template switching can be used to increase the length of a cDNA, e.g., by appending a predefined nucleic acid sequence to the cDNA.
Pre-processing for Capture Probe Interaction.

In some embodiments, nucleic acid analytes or sequence reads in a biological sample can be pre-processed prior to interaction with a capture probe. For example, prior to interaction with capture probes, polymerization reactions catalyzed by a polymerase (e.g., DNA polymerase or reverse transcriptase) are performed in the biological sample. In some embodiments, a primer for the polymerization reaction includes a functional group that enhances hybridization with the capture probe. The capture probes can include appropriate capture domains to capture biological analytes of interest (e.g., poly-dT sequence or oligo-dT probes to capture poly(A) mRNA).

In some embodiments, biological analytes are pre-processed for library generation via next generation sequencing. For example, nucleic acid analytes or sequence reads can be pre-processed by addition of a modification (e.g., ligation of sequences that allow interaction with capture probes). In some embodiments, nucleic acid analytes or sequence reads (e.g., DNA or RNA) are fragmented using fragmentation techniques (e.g., using transposases and/or fragmentation buffers).

Fragmentation can be followed by a modification of the nucleic acid analyte. For example, a modification can be the addition through ligation of an adapter sequence that allows hybridization with the capture probe. In some embodiments, where the nucleic acid analyte of interest is RNA, poly(A) tailing is performed. Addition of a poly(A) tail to RNA that does not contain a poly(A) tail can facilitate hybridization with a capture probe that includes a capture domain with a functional amount of poly(dT) sequence.

In some embodiments, prior to interaction with capture probes, ligation reactions catalyzed by a ligase are performed in the biological sample. In some embodiments, the capture domain includes a DNA sequence that has complementarity to a RNA molecule, where the RNA molecule has complementarity to a second DNA sequence, and where the RNA-DNA sequence complementarity is used to ligate the second DNA sequence to the DNA sequence in the capture domain. In these embodiments, direct detection of RNA molecules is possible.

In some embodiments, prior to interaction with capture probes, target-specific reactions are performed in the biological sample. Examples of target specific reactions include, but are not limited to, ligation of target specific adaptors, probes and/or other oligonucleotides, target specific amplification using primers specific to one or more nucleic acid analytes, and target-specific detection using in situ hybridization, DNA microscopy, and/or antibody detection. In some embodiments, a capture probe includes capture domains targeted to target-specific products (e.g., amplification or ligation).
Capture Probes.

A "capture probe" refers to any molecule capable of capturing (directly or indirectly) and/or labelling an analyte of interest in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

In some embodiments, the capture probe is optionally coupled to a support by a cleavage domain, such as a disulfide linker. The capture probe can include functional sequences that are useful for subsequent processing, such as a sequencer specific flow cell attachment sequence (e.g., a P5 sequence or P7 sequence) and/or sequencing primer sequences (e.g., a R1 or R2 primer binding site). A spatial barcode can be included within the capture probe for use in barcoding the target analyte. The functional sequences can be selected for compatibility with a variety of different sequencing systems, e.g., 454 Sequencing, Ion Torrent Proton or PGM, Illumina X10, etc., and the requirements thereof. In some embodiments, the spatial barcode and functional sequences can be common to all of the probes attached to a given support. The spatial barcode can also include a capture domain to facilitate capture of a target analyte.

As discussed above, each capture probe includes at least one capture domain. The "capture domain" is an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence (e.g., a nucleic acid bait) configured to interact with one or more nucleic acid analytes (e.g., RNA molecules and DNA molecules). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence, which poly(T) sequences are configured to interact with messenger RNA (mRNA) molecules via the poly(A) tail of an mRNA transcript. In some embodiments, the functional nucleic acid sequence is the binding target of a protein (e.g., a transcription factor, a DNA binding protein, or an RNA binding protein), where the analyte of interest is a protein.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules.

In some embodiments, the capture domain is located at the 3' end of the capture probe and includes a free 3' end that can be extended, e.g. by template dependent polymerization, to form an extended capture probe as described herein. In some embodiments, the capture domain includes a nucleotide sequence that is capable of hybridizing to nucleic acid, e.g. RNA or other analyte, present in the cells of the tissue sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, i.e., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly-U oligonucleotide or an oligonucleotide included of deoxythymidine analogues.

In some embodiments, the capture probe is immobilized on a feature (e.g., of a substrate or a solid support) via its 3' end. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain. Other non-limiting aspects and embodiments of capture probes, including capture domains and nucleic acid baits, are provided in U.S. Provisional Patent Application No. 62/839,346 entitled "SPATIAL TRANSCRIPTOMICS OF BIOLOGICAL ANALYTES IN TISSUE SAMPLES," filed Apr. 26, 2019, which is hereby incorporated herein by reference in its entirety.

Substrates.

The substrate functions as a support (e.g., a solid support) for direct or indirect attachment of capture probes to features of an array. In addition, in some embodiments, a substrate (e.g., the same substrate or a different substrate) can be used to provide support to a biological sample, particularly, for example, a thin tissue section. Accordingly, a "substrate" is a support that is insoluble in aqueous liquid and which allows for positioning of biological samples, analytes, features, and/or capture probes on the substrate.

A "feature" is an entity that acts as a support or repository for various molecular entities used in sample analysis. Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or feature using a variety of techniques. In some embodiments, the capture probe is directly attached to a feature that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g. a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, functionalized biomolecules (e.g., capture probes) are immobilized on a functionalized substrate using covalent methods. In some embodiments, functionalized biomolecules (e.g., capture probes) are immobilized on a functionalized substrate using photochemical covalent methods. In some embodiments, functionalized biomolecules (e.g., capture probes are immobilized on a functionalized substrate using non-covalent methods.

A "bead" is a particle. A bead can be porous, non-porous, solid, semi-solid, and/or a combination thereof. In some embodiments, a bead can be dissolvable, disruptable, and/or degradable, whereas in certain embodiments, a bead is not degradable.

A bead can generally be of any suitable shape. Examples of bead shapes include, but are not limited to, spherical, non-spherical, oval, oblong, amorphous, circular, cylindrical, and variations thereof. A cross section (e.g., a first cross-section) can correspond to a diameter or maximum cross-sectional dimension of the bead. In some embodiments, the bead can be approximately spherical. In such embodiments, the first cross-section can correspond to the diameter of the bead. In some embodiments, the bead can be approximately cylindrical. In such embodiments, the first cross-section can correspond to a diameter, length, or width along the approximately cylindrical bead.

The above descriptions are included as explanatory examples only and are non-limiting. Other non-limiting aspects and embodiments of substrates, arrays, beads, and bead arrays are provided in U.S. Provisional Patent Application No. 62/839,346 entitled "SPATIAL TRANSCRIPTOMICS OF BIOLOGICAL ANALYTES IN TISSUE SAMPLES," filed Apr. 26, 2019, which is hereby incorporated herein by reference in its entirety.

Analyte Capture.

In this section, general aspects of methods and systems for capturing analytes are described. Individual method steps and system features can be present in combination in many different embodiments; the specific combinations described herein do not in any way limit other combinations of steps and features.

Generally, analytes can be captured when contacting a biological sample with, e.g., a substrate comprising capture probes (e.g., substrate with capture probes embedded, spotted, printed on the substrate or a substrate with features (e.g., beads, wells) comprising capture probes).

As used herein, "contact," "contacted," and/or "contacting," a biological sample with a substrate comprising features refers to any contact (e.g., direct or indirect) such that capture probes can interact (e.g., capture) with analytes from the biological sample.

Capture probes on the substrate (or on a feature on the substrate) interact with released analytes through a capture domain, described elsewhere, to capture analytes. In some embodiments, a capture domain captures analytes via hybridization to a nucleic acid sequence in a target nucleic acid molecule.

Other non-limiting aspects and embodiments of analyte capture are provided in U.S. Provisional Patent Application No. 62/839,346 entitled "SPATIAL TRANSCRIPTOMICS OF BIOLOGICAL ANALYTES IN TISSUE SAMPLES," filed Apr. 26, 2019, which is hereby incorporated herein by reference in its entirety.

Sequencing Analysis.

After analytes from the sample have hybridized or otherwise been associated with capture probes, analyte capture agents, or other barcoded oligonucleotide sequences according to any of the methods described above in connection with the general spatial cell-based analytical methodology, the constructs that result from hybridization/association (e.g., nucleic acid bait—sequence read complexes) are analyzed via sequencing to identify the analytes.

A wide variety of different sequencing methods can be used to analyze analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule, or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the barcoded nucleic acid molecule can be subjected to a step of second strand synthesis or amplification before sequence analysis (e.g. sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g. barcoded nucleic acid molecules) can be analyzed (e.g. sequenced). To perform single molecule sequencing, the nucleic acid strand can be modified at the 3' end.

Other non-limiting aspects and embodiments of analyte capture and sequencing analysis are provided in U.S. Provisional Patent Application No. 62/839,346 entitled "SPATIAL TRANSCRIPTOMICS OF BIOLOGICAL ANALYTES IN TISSUE SAMPLES," filed Apr. 26, 2019, and in U.S. Provisional Patent Application No. 62/979,889 entitled "CAPTURING TARGETED GENETIC TARGETS USING A HYBRIDIZATION/CAPTURE APPROACH," filed Feb. 21, 2020, each of which is hereby incorporated herein by reference in its entirety.

The above definitions provide a summary of exemplary methods, materials, compositions, and systems that are referred to in the context of various implementations in the present disclosure. The examples are intended to provide a basic understanding of some of embodiments of the disclosure but are not an extensive or exhaustive representation of all embodiments of the disclosure. They are not intended to identify key/critical elements of the disclosure or to delineate the scope of the disclosure. The sole purpose of these definitions is to present some of the concepts of the embodiments of the present disclosure in a simplified form for general understanding. Other embodiments of the methods described herein will be apparent to one skilled in the art. Further implementations are incorporated by reference in the respective sections.

Exemplary System Embodiments

Now that a general summary of the methods and terminology has been presented, detailed descriptions of various implementations of the present disclosure will now be described in conjunction with the figures.

FIG. 1 is a block diagram illustrating a computing device 100 in accordance with some implementations.

The device 100 in some implementations includes one or more processing unit(s) 102 (also referred to as processors or CPUs), one or more network interfaces 104, a user interface 106, a display 108, an input module 110, a memory 112, and one or more communication buses 114 for interconnecting these components. The one or more communication buses 114 optionally include circuitry (sometimes called a chipset) that interconnects and controls communications between system components. The memory 112 typically includes high-speed random access memory, such as DRAM, SRAM, DDR RAM, ROM, EEPROM, and/or flash memory, CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The memory 112 optionally includes one or more storage devices remotely located from the CPU(s) 102. The memory 112 comprises non-transitory computer readable storage medium. In some implementations, the memory 112 or alternatively the non-transitory computer readable storage medium stores the following programs, modules and data structures, or a subset thereof:

- an optional operating system 116, which includes procedures for handling various basic system services and for performing hardware dependent tasks;
- an optional network communication module (or instructions) 118 for connecting the visualization system 100 with other devices, or a communication network;
- an optional genetic target data structure 120 for storage of a genetic target dataset 122 within the memory, where the genetic target dataset 122 includes one or more genetic targets 122-1, 122-2, and 122-Q for Q genetic targets (e.g., genes of interest), and where each respective genetic target includes a candidate hybridization sequence 123 (e.g., 123-1) and/or one or more transcripts 124 in a plurality of transcripts (e.g., for genetic target 1 122-1, P isoforms denoted by 124-1-1, ..., 124-1-P);
- an optional cDNA sequence data structure 126 for storage of a plurality of cDNA sequences 130 (e.g., 130-1-1, 130-1-2, 130-1-N), where the plurality of cDNA sequences comprises a first subset of cDNA sequences 128-1 and a second subset of cDNA sequences 128-2, each respective cDNA sequence in the first subset of cDNA sequences maps to a respective genetic target (e.g., gene of interest) in a plurality of genetic targets, and each respective cDNA sequence in the second subset of cDNA sequences maps to a portion of a reference genome not represented by the plurality of genetic targets;
- an optional hybridization module 132 comprising a plurality of nucleic acid baits 134 (e.g., 134-1, 134-2, ..., 134-T) and a hybridization processing construct 136 for hybridizing a respective nucleic acid bait 134 to a transcript 124 in the one or more transcripts of a genetic target 122 in the one or more genetic targets, where the hybridization module further optionally stores parameterized attribute values that define the hybridization for each nucleic acid bait generated by the hybridization processing construct (e.g., subsequence matching counts, bait length, bait position, number of residues, nucleic acid sequence, sequence identity parameters, strand designation, melting temperature, filtration parameters, mappability, GC content, repeats and/or input values for M, P, L, and/or K, and/or any subset thereof);
- an optional sub-sequence matching module 138 for, for each genetic target 122, determining a count of a number of transcripts in a corresponding plurality of transcripts 124 that matches a sub-sequence of length K of the corresponding candidate hybridization sequence 123, thus determining a first sub-sequence that matches a first maximal number of transcripts in a first subset of transcripts, in a corresponding plurality of subsets of transcripts, and a second sub-sequence that matches a second maximal number of transcripts in a second subset of transcripts, in the corresponding plurality of subsets of transcripts, other than the first subset of transcripts; and
- optionally, a reference genome 140 for identifying nucleic acid baits that hybridize to off-target sequences not included in the genetic target data structure 120.

In some implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the memory 112 optionally stores a subset of the modules and data structures identified above. Furthermore, in some embodiments, the memory stores additional modules and data structures not described above. In some embodiments, one or more of the above identified elements is stored in a computer system, other than that of computing device 100, that is addressable by computing device 100 so that computing device 100 may retrieve all or a portion of such data when needed.

Although FIG. 1 depicts a "computing device 100," the figures are intended more as functional description of the various features which may be present in computer systems than as a structural schematic of the implementations described herein. In practice, and as recognized by those of ordinary skill in the art, items shown separately could be combined and some items could be separated. While a system in accordance with the present disclosure has been disclosed with reference to FIG. 1, methods in accordance with the present disclosure are now detailed with reference to FIGS. 2A, 2B, 2C, 2D, 3A, 3B, and 3C.

Specific Embodiments

I. Methods for Capturing Targeted Sequences using a Hybridization Capture Approach Referring to Block 202, one aspect of the present disclosure provides a method 200 of capturing targeted sequences using a hybridization and capture approach.

The method comprises obtaining a plurality of cDNA sequences from a pool of poly-adenylated mRNA obtained from a biological sample of a subject, where the plurality of cDNA sequences comprise a first subset of cDNA sequences and a second subset of cDNA sequences, each respective cDNA sequence in the first subset of cDNA sequences maps to a respective gene in a plurality of genes, each respective cDNA sequence in the second subset of cDNA sequences maps to a portion of a reference genome not represented by the plurality of genes, and each respective gene in the plurality of genes is characterized by a corresponding plurality of transcripts.

Obtaining Biological Samples

In some embodiments, the subject is a human. In some embodiments, the biological sample is a liquid biological sample or a tissue sample. Biological samples contemplated for use in the present disclosure include, but are not limited to, any of the aspects and/or embodiments described above (see: Definitions).

In some embodiments, the biological sample comprises, but is not limited to, any RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. In some embodiments, the RNA is a transcript (e.g., present in a tissue section). In some embodiments, the RNA is small (e.g., less than 200 nucleic acid bases in length) or large (e.g., RNA greater than 200 nucleic acid bases in length). Small RNAs generally include, but are not limited to, 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). In some embodiments, the RNA is double-stranded RNA or single-stranded RNA. In some embodiments, the RNA is circular RNA and/or bacterial rRNA (e.g., 16s rRNA or 23s rRNA).

In some embodiments, obtaining the pool of poly-adenylated mRNA from the biological sample comprises any method of nucleic acid extraction and/or isolation known in the art.

In some embodiments, the pool of poly-adenylated mRNA is obtained from the biological sample in preparation for a sequencing method (e.g., by any method encompassed in a sequencing library preparation workflow). Referring to Block 204, in some embodiments, the pool of poly-adenylated mRNA is obtained from the biological sample by single cell 3' sequencing, single cell 5' sequencing, or single cell 5' paired-end sequencing.

In some embodiments, the biological sample comprises a plurality of cells.

In some embodiments, the plurality of cells includes at least 100, at least 200, at least 500, at least 1000, at least 2000, at least 3000, at least 4000, at least 5000, at least 6000, at least 7000, at least 8000, at least 9000, at least 10,000, at least 15,000, at least 20,000, at least 30,000, at least 40,000, at least 50,000, at least 60,000, at least 70,000, at least 80,000 cells, or at least 100,000 cells. In some embodiments, the plurality of cells includes no more than 1 million, no more than 500,000, no more than 100,000, no more than 50,000, no more than 10,000, no more than 5000, no more than 1000, or no more than 500 cells. In some embodiments, the plurality of cells includes from 100 to 10,000, from 500 to 20,000, from 1000 to 15,000, from 5000 to 30,000, from 10,000 to 100,000, or from 10,000 to 1 million cells. In some embodiments, the plurality of cells falls within another range starting no lower than 100 cells and ending no higher than 1 million cells.

Obtaining cDNA Sequences

In some embodiments, the obtaining the plurality of cDNA sequences comprises performing first-strand cDNA synthesis via reverse transcription of the corresponding pool of poly-adenylated mRNA. In some such embodiments, the cDNA is generated using a poly(T) containing primer. In some embodiments, the generated cDNA is barcoded using a capture probe, featuring a barcode sequence (and optionally, a UMI sequence) that hybridizes with at least a portion of the generated cDNA. In some embodiments, the generated cDNA is appended with a unique molecular identifier (UMI) using a capture probe featuring a UMI that hybridizes with at least a portion of the generated cDNA. In some embodiments, a template switching oligonucleotide hybridizes to a poly(C) tail added to a 3' end of the cDNA by a reverse transcriptase enzyme. In some such embodiments, the original mRNA template and template switching oligonucleotide is denatured from the cDNA, and the barcoded capture probe with optional UMI hybridizes with the cDNA to generate a complement of the cDNA.

In some embodiments, the obtaining the plurality of cDNA sequences further comprises amplification (e.g., PCR amplification) and/or adaptor extension of each cDNA sequence in the plurality of cDNA sequences. In some embodiments, the adaptor extension occurs prior to cDNA amplification. In some such embodiments, the adaptor extension occurs during the first-strand cDNA synthesis. In some such embodiments, the adaptor extension occurs by hybridization of the RNA molecule to a capture probe. In some other embodiments, the adaptor extension occurs by hybridization of a cDNA molecule to a capture probe.

In some embodiments, the plurality of cDNA sequences is used to prepare a cDNA library including one or more cDNA sequences of interest, whose detection can be enhanced using hybridization methods.

In some embodiments, the plurality of cDNA sequences is not fragmented, such that each cDNA sequence in the plurality of cDNA sequences is a full-length cDNA sequence. In some such embodiments, the plurality of cDNA sequences comprises intermediate products of a gene expression library preparation workflow (e.g., unfragmented cDNA sequences generated using a method for 3' and/or 5' gene expression library preparation).

Any method for obtaining cDNA sequences known in the art is contemplated in the present disclosure. For example, methods for obtaining cDNA sequences for gene expression analysis and/or spatial analysis of analytes contemplated for use in the present disclosure are further described in 10X Genomics, 2019, "Chromium Next GEM Single Cell 3' Reagent Kits v3.1 User Guide", Document Number CG000204, Rev D; 10X Genomics, 2017, "Chromium Single Cell 3' Reagent Kits v2 User Guide," Document Number CG00052 Rev B; 10X Genomics, 2020, "Chromium Single Cell V(D)J Reagents Kits User Guide," Document Number CG000086, Rev M; 10X Genomics, "What is the difference between Single Cell 3' and 5' Gene Expression libraries?", available on the internet at kb.10xgenomics.com/hc/en-us/articles/360000939852-What-is-the-difference-between-Single-Cell-3-and-5-Gene-Expression-libraries-; U.S. Provisional Patent Application No. 63/041,825, entitled "Pipeline for Spatial Analysis of Analytes," filed Jun. 20, 2020; U.S. Provisional Patent Application No. 63/041,823, entitled "Systems and Methods for Identifying Morphological Patterns in Tissue Samples," filed Jun. 20, 2020; and U.S. patent application Ser. No. 17/168,050, entitled "Systems and Methods for Index Hopping Filtering," filed Feb. 4, 2021, each of which is hereby incorporated herein by reference in its entirety. Example workflows for obtaining cDNA sequences for enrichment (with optional fragmentation prior to hybridization) are described in Example 2, below, with reference to FIGS. 8A and 8B.

In some embodiments, the plurality of cDNA sequences is obtained from a single cDNA library. In some embodiments, the plurality of cDNA sequences is obtained from a plurality of cDNA libraries. In some such embodiments, the plurality of cDNA libraries is pooled (e.g., for multiplexing).

Referring to Block 206, in some embodiments, the plurality of cDNA sequences is at least $1 \times 10^6$ cDNA sequences. In some embodiments, the plurality of cDNA sequences is at least $1 \times 10^7$ cDNA sequences.

In some embodiments, the plurality of cDNA sequences is at least $1 \times 10^3$, at least $2 \times 10^3$, at least $3 \times 10^3$, at least $5 \times 10^3$, at least $1 \times 10^4$, at least $2 \times 10^4$, at least $3 \times 10^4$, at least $5 \times 10^4$, at least $1 \times 10^5$, at least $2 \times 10^5$, at least $3 \times 10^5$, at least $5 \times 10^5$, at least $1 \times 10^6$, at least $2 \times 10^6$, at least $3 \times 10^6$, at least $4 \times 10^6$, at least $5 \times 10^6$, at least $6 \times 10^6$, at least $7 \times 10^6$, at least $8 \times 10^6$, at least $9 \times 10^6$, at least $1 \times 10^7$, at least $1 \times 10^8$, or at least $1 \times 10^9$ cDNA sequences. In some embodiments, the plurality of cDNA sequences is no more than $1 \times 10^{10}$, no more than $1 \times 10^9$, no more than $1 \times 10^8$, no more than $1 \times 10^7$, no more than $1 \times 10^6$, no more than $1 \times 10^5$, or no more than $1 \times 10^4$ cDNA sequences. In some embodiments, the plurality of cDNA sequences is from $1 \times 10^3$ to $1 \times 10^6$, from $1 \times 10^4$ to $1 \times 10^7$, from $1 \times 10^5$ to $1 \times 10^8$, from $5 \times 10^3$ to $1 \times 10^8$, from $1 \times 10^6$ to $5 \times 10^7$, from $1 \times 10^3$ to $5 \times 10^5$, or from $1 \times 10^5$ to $5 \times 10^6$ cDNA sequences. In some embodiments, the plurality of cDNA sequences falls within another range starting no lower than $1 \times 10^3$ cDNA sequences and ending no higher than $1 \times 10^{10}$ cDNA sequences.

In some embodiments, the plurality of cDNA sequences comprises a first subset of cDNA sequences, where each respective cDNA sequence in the first subset of cDNA sequences maps to a respective gene in a plurality of genes. In some embodiments, the plurality of genes is a targeted gene panel (e.g., a panel of genes of interest). Referring to Block 208, in some embodiments, the plurality of genes is between five genes and twenty thousand genes. In some embodiments, the plurality of genes is between one hundred genes and ten thousand genes. In some embodiments, the plurality of genes is between five hundred genes and two thousand genes. In some embodiments, the plurality of genes is more than 10, more than 50, more than 100, more than 500, more than 1000, more than 2000, more than 5000, more than 10000, more than 15000, or more than 20000 genes.

In some embodiments, the plurality of genes comprises at least 3, at least 5, at least 10, at least 20, at least 30, at least 40, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 15,000, at least 20,000, or at least 30,000 genes. In some embodiments, the plurality of genes comprises no more than 100,000, no more than 50,000, no more than 10,000, no more than 5000, no more than 2000, no more than 1000, no more than 500, or no more than 100 genes. In some embodiments, the plurality of genes is from 5 to 30,000, from 50 to 10,000, from 200 to 5000, or from 500 to 2000 genes. In some embodiments, the plurality of genes falls within another range starting no lower than 3 genes and ending no higher than 100,000 genes.

In some embodiments, the plurality of genes comprises a subset of genes associated with a condition of interest (e.g., a gene panel). In some embodiments, the condition of interest is a disease, a molecular or biological function, and/or a biological pathway (e.g., a gene signature panel, immunology panel, pan-cancer panel, and/or neuroscience panel). In some embodiments, the condition of interest is for a mammal. In some embodiments, the condition of interest is for a human (e.g., human gene signature, human immunology, human pan-cancer, and/or human neuroscience).

In some embodiments, the plurality of cDNA sequences comprises a second subset of cDNA sequences, where each respective cDNA sequence in the second subset of cDNA sequences maps to a portion of a reference genome not represented by the plurality of genes. In some embodiments, the second subset of cDNA sequences includes cDNA sequences that map to off-target regions of the reference genome and/or other genes not included in a targeted gene panel.

In some embodiments, the plurality of cDNA sequences consists of the first subset of cDNA sequences and the second subset of cDNA sequences. Then, in some such embodiments, each cDNA sequence in the plurality of cDNA sequences maps to either a gene of interest or to an off-target region of a reference genome.

In some embodiments, the corresponding plurality of transcripts that characterizes each respective gene in the plurality of genes is any number of transcripts. For example, referring to Block 210, in some embodiments, the plurality of transcripts corresponding to the respective gene comprises three or more transcripts for the respective gene. In some embodiments, the plurality of transcripts corresponding to the respective gene comprises five or more transcripts for the respective gene. In some embodiments, the plurality of transcripts comprises 2, 3, 4, 5, 6, 7, 8, 9, 10 or more transcripts for the respective gene. For instance, in some embodiments, the plurality of transcripts comprises at least 2, at least 3, at least 4, at least 5, at least 6, at least 7, at least 8, at least 9, at least 10, at least 15, at least 20, at least 25, or at least 30 transcripts for the respective gene. In some embodiments, the plurality of transcripts comprises no more than 50, no more than 40, no more than 30, no more than 20, no more than 10, or no more than 5 transcripts for the respective gene. In some embodiments, the plurality of transcripts comprises from 2 to 5, from 3 to 10, from 5 to 15, from 2 to 20, or from 5 to 30 transcripts for the respective gene. In some embodiments, the plurality of transcripts falls within another range starting no lower than 2 transcripts and ending no higher than 50 transcripts.

Referring to Block 212, in some embodiments, the corresponding plurality of transcripts of a respective gene in the plurality of genes comprises a plurality of isoforms of the respective gene. In some embodiments, each transcript in the corresponding plurality of transcripts of a respective gene in the plurality of genes is an isoform of the respective gene. In some embodiments, each transcript in the corresponding plurality of transcripts of each respective gene in the plurality of genes is an isoform of the respective gene.

Isoforms of a gene or a genetic target refer to mRNA molecules (and/or the corresponding cDNA molecules) that originate from the same genomic locus but comprise different nucleic acid sequences, including but not limited to transcription start sites (TSSs), protein coding DNA sequences (CDSs), and/or untranslated regions (UTRs). These differences are caused by alternative splicing, variable promoter usage, gene fusions or deletions, single nucleotide polymorphisms (SNPs), and/or other mutations or post-transcriptional modifications of specific genes. Isoforms of a gene can have different functional capacities due to the differences in mRNA sequence of the coding sequences and/or the cis-regulatory elements in the promoter sequences. Such alternative sequences can be recognized by alternative transcription factors and produce differential gene expression or behavior.

Referring to Block 214, in some embodiments, the plurality of isoforms of the respective gene comprises a first transcriptional isoform and a second transcriptional isoform of the respective gene. In some embodiments, the plurality of isoforms of the respective gene comprises 2, 3, 4, 5, 6, 7, 8, 9, 10 or more isoforms for the respective gene.

Generally, identification of different isoforms of a gene is used to more accurately enrich for cDNA sequences of the respective gene. For example, in some cases where the diverging nucleic acid sequences of two or more isoforms of a target gene include different transcription start sites and/or untranslated regions, hybridization/capture probes complementary to the 3' or 5' annotated ends of the gene can fail to capture all of the possible isoforms. This can occur if a nucleic acid bait is designed to hybridize to a region of a first isoform that extends beyond either of the terminal ends of a second isoform. While minimal probe sets are desirable for cost-effective and streamlined targeted sequencing analysis, in some cases where two or more isoforms have such drastically different lengths that they do not overlap, the method includes designing a plurality of nucleic acid baits such that each isoform can be hybridized and enriched. In some such cases, each non-overlapping isoform hybridizes to a different, unique nucleic acid bait. Thus, in some embodiments, annotations of the genomic regions spanned by each respective isoform in a plurality of isoforms for a respective target gene (e.g., the coding and/or non-coding sequences) are used in order to design and generate a plurality of baits in which every transcript for the target gene is represented (e.g., hybridizable).

Referring to Block 216, in some embodiments, each transcript in the plurality of transcripts is protein coding. Alternatively, in some embodiments, one or more transcripts in the plurality of transcripts comprises a non-coding sequence (e.g., a 3' or 5' untranslated region). For example, one or more transcripts in the plurality of transcripts can comprise a 3' UTR sequence downstream of a stop codon, or a 5' UTR upstream of a start codon. In some embodiments, one or more transcripts in the plurality of transcripts is protein coding but comprises an incomplete coding sequence. For example, in some such embodiments, a transcript in the plurality of transcripts corresponding to the respective gene is coding sequence (CDS) 3' incomplete, CDS 5' incomplete, or both CDS 3' and 5' incomplete. As used herein, CDS 3' incomplete refers to a protein-coding transcript that does not include the stop codon due to incomplete evidence. As used herein, CDS 5' incomplete refers to a protein-coding transcript that does not include a start codon due to incomplete evidence.

The designations of each transcript in the plurality of transcripts as, e.g., protein coding, non-coding, CDS 3' incomplete, and/or CDS 5' incomplete is determined, in some implementations, using gene annotations obtained from a reference database. For example, referring to Block 218, in some embodiments, the plurality of transcripts corresponding to the respective gene is each transcript of the respective gene annotated in GENCODE Release 33 (GRCh38.p 13). In some such embodiments, each designation of each transcript in the plurality of transcripts is informed by annotations for known isoforms of the respective gene, where annotations are based on functional and/or evolutionary conservation of a respective isoform in the plurality of isoforms. For instance, annotations for a respective gene are available as a reference database within the GENCODE Consortium, which compiles data from computational studies, manual annotations, and experimental validation to identify gene features in the human genome, including protein coding and non-coding DNA and RNA sequences. In other instances, annotations for a respective gene are available through the Ensembl project, which provides genome annotations for chordate genomes, as well as software and toolsets to perform data mining and analysis. See, Harrow et al., 2012, "GENCODE: The reference human genome annotation for The ENCODE Project," Genome Res. 22(9): 1760-1774: doi:10.1101/gr.135350.111; and Flicek et al., 2014, "Ensembl 2014," Nucleic Acids Res. 42(Database issue):D749-D755: doi: 10.1093/nar/gkt1196, the entire contents of which are incorporated herein by reference.

In some embodiments, each transcript in the plurality of transcripts corresponding to the respective gene has GENCODE transcript support level 1. In some embodiments, each transcript in the plurality of transcripts corresponding to the respective gene has GENCODE transcript support level 1, GENCODE transcript support level 2, or GENCODE transcript support level 3. Support levels for GENCODE transcripts include level 1 (e.g., all splice junctions of the transcript are supported by at least one non-suspect mRNA), level 2 (e.g., the best supporting mRNA is flagged as suspect or the support is from multiple ESTs), and/or level 3 (e.g., the only support is from a single EST), among others. Annotations in GENCODE can further include automatically annotated loci, manually annotated loci, and/or experimentally verified loci. Additional annotations for each transcript in the plurality of transcripts corresponding to the respective gene are possible, as will be apparent to one skilled in the art.

In some implementations, the plurality of transcripts corresponding to the respective gene comprises each transcript of the respective gene as annotated in any reference database appropriate for the subject. For example, human gene annotations can be further obtained from ENSEMBL, RefSeq, and/or the Gene Ontology Consortium. In some embodiments, the plurality of transcripts corresponding to the respective gene comprises each transcript of the respective gene annotated in the respective reference database. In some embodiments, the plurality of transcripts corresponding to the respective gene consists of each transcript of the respective gene annotated in the respective reference database. In some alternative embodiments, one or more transcripts annotated in the respective reference database is removed (e.g., filtered) from the plurality of transcripts corresponding to the respective gene.

In some embodiments, each transcript in the plurality of transcripts corresponding to each respective gene in the plurality of genes is appended with a barcode and/or a unique molecular identifier (UMI). In some embodiments, the plurality of barcodes and/or UMIs corresponding to the plurality of transcripts across the plurality of genes represents the complexity of the biological sample (e.g., the UMI complexity).

Nucleic Acid Baits

Referring to Block 220, the method further comprises exposing the plurality of cDNA sequences to a plurality of nucleic acid baits (e.g. at least 100, at least 500, at least 1000, at least 2000, at least 3000, at least 4000, or at least 5000 nucleic acid baits), each of length that is between $K_1$ and $K_2$ residues, thus forming a plurality of nucleic acid bait-sequence read complexes. Each respective nucleic acid bait in the plurality of nucleic acid baits that hybridizes to a cDNA sequence mapping to a respective gene in the plurality of genes (i) selectively hybridizes to a first subset of transcripts, in a corresponding plurality of subsets of transcripts in the plurality of transcripts corresponding to the respective gene, or (ii) selectively hybridizes to another subset of transcripts, other than the first subset of transcripts, in the corresponding plurality of subsets of transcripts in the plurality of transcripts corresponding to the respective gene. Each respective transcript in the corresponding plurality of transcripts of each respective gene in the plurality of genes is hybridizable to a nucleic acid bait in the plurality of nucleic acid baits.

Thus, for instance, in some embodiments, the plurality of nucleic acid baits span (e.g., hybridize to) all mature mRNA sequences, including UTRs and all annotated isoforms for a respective gene in the plurality of genes (e.g. a target gene in the plurality of target genes). Furthermore, in some embodiments, the plurality of nucleic acid baits span (e.g., hybridize to) all mature mRNA sequences, including UTRs and all annotated isoforms for each respective gene in the plurality of genes (e.g. each target gene in the plurality of target genes).

For example, a nucleic acid bait can hybridize to (e.g., can comprise nucleic acid sequences complementary to) one or more nucleic acid sequences corresponding to a target gene. In some cases, the one or more nucleic acid sequences that hybridize to the nucleic acid bait represent a corresponding one or more transcripts, or isoforms, of the target gene. In some embodiments, a subset of transcripts (e.g., a subset of isoforms) refers to the group of transcripts (e.g., isoforms), for the respective target gene, that hybridize to a respective nucleic acid bait.

In some embodiments, a nucleic acid bait that hybridizes to a cDNA sequence for a target gene selectively hybridizes to each transcript in the plurality of transcripts for the respective gene. In some embodiments, a single nucleic acid bait hybridizes to all isoforms for a target gene, such that the first subset of isoforms consists of the plurality of isoforms for the target gene. In some such instances, no other subset of isoforms is defined (e.g., the plurality of isoforms can be grouped into only a single or first subset of isoforms).

In some instances, the plurality of transcripts for a target gene is subdivided into a plurality of subsets of transcripts. In some such embodiments, the plurality of subsets of transcripts includes a first and a second subset of transcripts. In some embodiments, each subset of transcripts in the plurality of subsets of transcripts refers to the group of transcripts to which a respective nucleic acid bait hybridizes. In some such embodiments, the first subset of transcripts is the group of transcripts to which at least a first nucleic acid bait hybridizes, and the second subset of transcripts is the group of transcripts to which at least a second nucleic acid bait hybridizes. For example, a first group of transcripts (e.g., isoforms) for the target gene that hybridize to a first nucleic acid bait is a first subset of transcripts (e.g., a first subset of isoforms). Furthermore, a second group of transcripts (e.g., isoforms) for the target gene that hybridize to a second nucleic acid bait is a second subset of transcripts (e.g., a second subset of isoforms). In some embodiments, the second subset of transcripts comprises transcripts not included in the first subset of transcripts. In some embodiments, the second subset of transcripts consists of transcripts not included in the first subset of transcripts (e.g., a first subset and a second subset of isoforms can comprise mutually exclusive groups of isoforms).

The selection of each subset of transcripts in the plurality of subsets of transcripts is determined, in some implementations, using a method disclosed in the following sections (see, Section II. Methods for Hybridization/Capture Probe Design), and is further illustrated by Example 1 and FIGS. 5A and 5B. Determination of a minimal bait set, for instance, is performed in some implementations by identifying maximal groupings of transcripts that can be selectively hybridized to by a corresponding one or more nucleic acid baits.

Figure 5A:
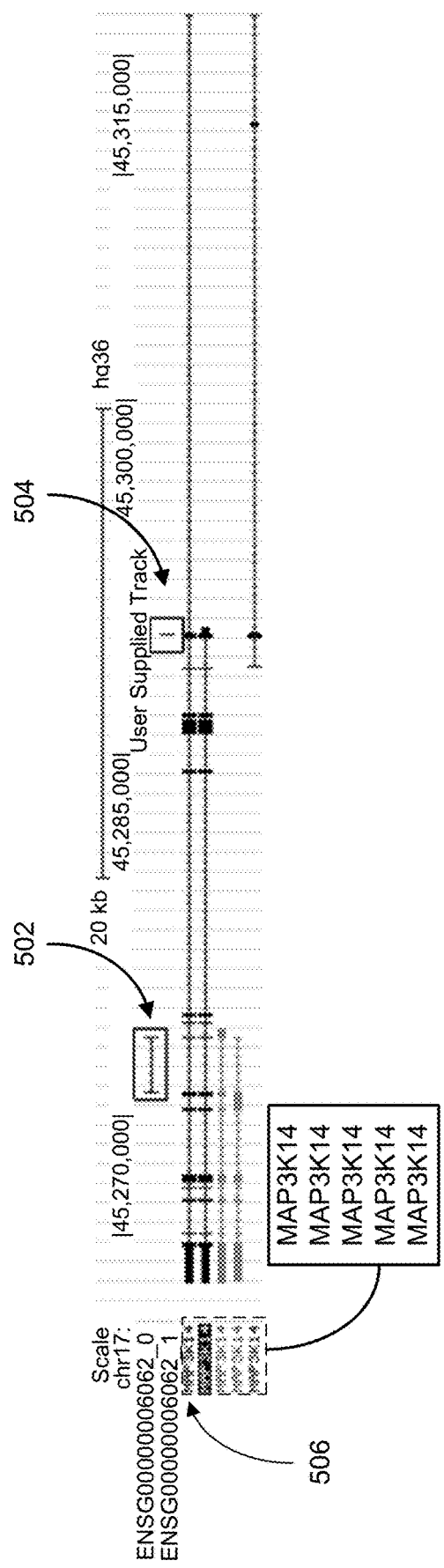
FIGS. 5A and 5B each illustrate a first nucleic acid bait corresponding to a first sub-sequence and a second nucleic acid bait corresponding to a second sub-sequence, in accordance with some embodiments of the present disclosure.
Figure 5B:
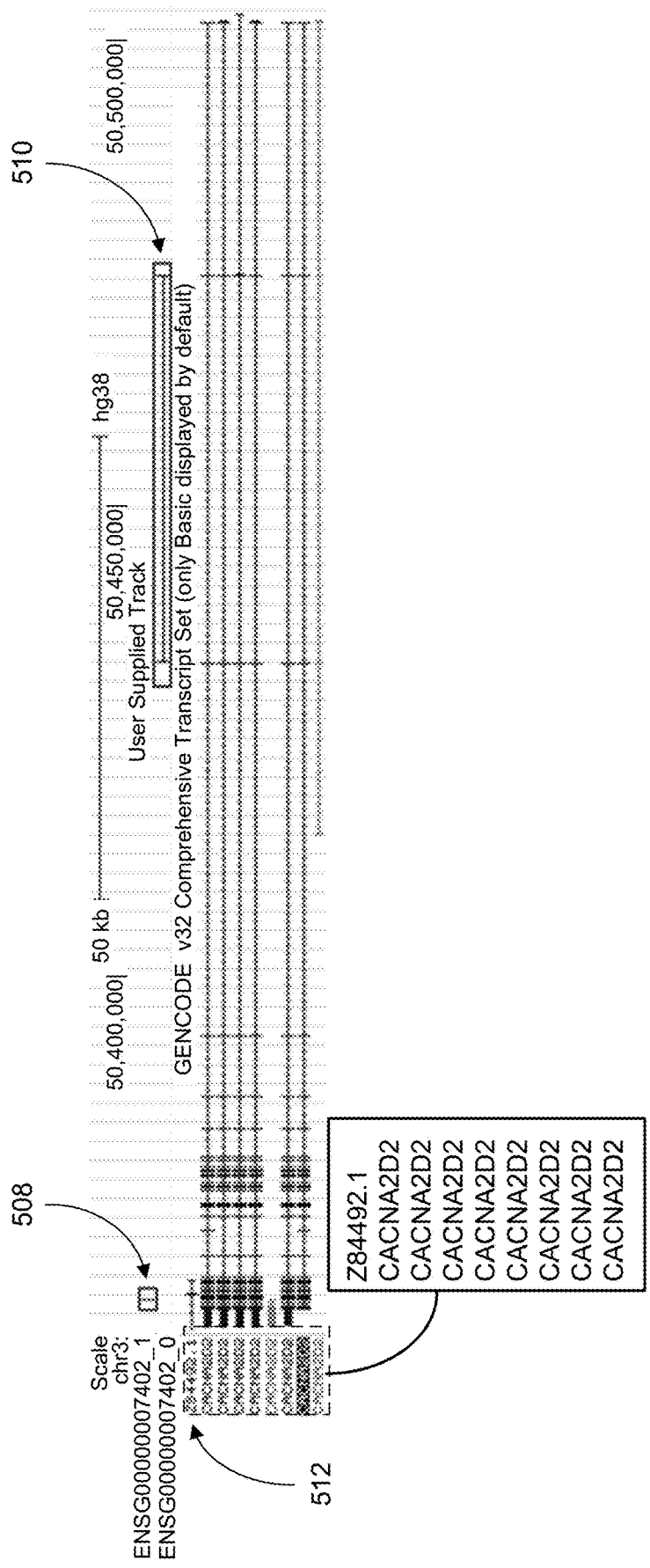

For example, as described below, a first subset of isoforms is selected by counting matches for each possible subsequence, of a given length, of a candidate bait sequence (e.g., sub-sequences of a target gene coding sequence or mRNA sequence). Hybridization matching between each possible bait sub-sequence and each position across each isoform is performed iteratively for every isoform for the respective gene. The number of isoforms that match (e.g., comprise a complementary sequence to) each bait subsequence is tallied, the bait sub-sequence with the highest number of matches is selected as the first nucleic acid bait, and the subset of isoforms that match the first nucleic acid bait is defined as the first subset of isoforms. In a first example, illustrated in FIG. 5A, a first nucleic acid bait 502 matches with four out of five possible isoforms 506, or the highest number of matches for the plurality of isoforms. In a second example, illustrated in FIG. 5B, a first nucleic acid bait 508 matches with eight out of nine possible isoforms 512, the highest number of matches for the plurality of isoforms. In FIGS. 5A and 5B, the group of four isoforms and the group of eight isoforms, respectively, define the first subset of isoforms.

When the corresponding first subset of isoforms fails to account for all the isoforms for the target gene, the process is repeated for all remaining isoforms that failed to match with the first nucleic acid bait. Thus, the bait sub-sequence with the highest number of matches to the remaining isoforms (e.g., the isoforms not included in the first subset of isoforms) is selected as the second nucleic acid bait, and the second subset of isoforms that match the second nucleic acid bait is defined as the second subset of isoforms. Referring again to FIG. 5A, a second nucleic acid bait 504 matches with the one remaining isoform out of five possible isoforms 506, the highest number of matches for the plurality of isoforms not including the isoforms in the first subset of isoforms. Referring again to FIG. 5B, a second nucleic acid bait 510 matches with the one remaining isoform out of nine possible isoforms 512, the highest number of matches for the plurality of isoforms not including the isoforms in the first subset of isoforms. In FIGS. 5A and 5B, the one remaining isoform defines the second subset of isoforms.

The process is repeated as many times as desired, and/or until a plurality of nucleic acid baits are identified such that all transcripts in the plurality of transcripts for the respective gene is hybridizable to at least one nucleic acid bait in the plurality of nucleic acid baits.

In some embodiments, the plurality of subsets of transcripts includes at least two, at least three, at least four, at least five, at least six, at least seven, at least eight, at least nine, or at least ten subsets of transcripts. In some embodiments, the plurality of subsets of transcripts includes at least 10, at least 15, at least 20, at least 25, at least 30, at least 35, or at least 50 subsets of transcripts. In some embodiments, the plurality of subsets of transcripts includes no more than 100, no more than 50, no more than 30, no more than 20, or no more than 10 subsets of transcripts. In some embodiments, the plurality of subsets of transcripts includes from 2 to 10, from 2 to 5, from 3 to 20, from 5 to 30, or from 2 to 40 subsets of transcripts. In some embodiments, the plurality of subsets of transcripts falls within another range starting no lower than 2 subsets and ending no higher than 100 subsets.

In some embodiments, each subset of transcripts corresponds (e.g., is hybridizable) to a single nucleic acid bait. In some alternative embodiments, each subset of transcripts corresponds (e.g., is hybridizable) to a plurality of nucleic acid baits. In some embodiments, a respective subset of transcripts corresponds to at least 1, at least 2, at least 3, at least 4, at least 5, at least 6, at least 7, at least 8, at least 9, at least 10, at least 15, at least 20, at least 25, at least 30, at least 35, at least 40, at least 45, or at least 50 nucleic acid baits. In some embodiments, a respective subset of transcripts corresponds to no more than 100, no more than 50, no more than 30, no more than 20, no more than 10, or no more than 5 nucleic acid baits. In some embodiments, a respective subset of transcripts corresponds to from 2 to 10, from 3 to 8, from 5 to 15, from 2 to 20, or from 5 to 30 nucleic acid baits. In some embodiments, a respective subset of transcripts corresponds to another range of nucleic acid baits starting no lower than 2 nucleic acid baits and ending no higher than 100 nucleic acid baits. Similarly (e.g., where a respective gene in the plurality of genes is characterized by one or more subsets of transcripts), in some embodiments, a respective gene in the plurality of genes corresponds to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 100, at least 200, at least 300, at least 400, at least 500, at least 600, at least 700, at least 800, at least 900, or at least 1000 nucleic acid baits. In some embodiments, a respective gene in the plurality of genes corresponds to no more than 2, no more than 3, no more than 4, no more than 5, no more than 6, no more than 7, no more than 8, no more than 9, no more than 20, no more than 30, no more than 100, no more than 2000, no more than 1000, no more than 500, no more than 100, no more than 50, no more than 30, or no more than 10 nucleic acid baits. In some embodiments, a respective gene in the plurality of genes corresponds to from 2 to 10, from 3 to 8, from 5 to 50, from 20 to 100, from 50 to 500, or from 100 to 1000 nucleic acid baits. In some embodiments, a respective gene in the plurality of genes corresponds to another range of nucleic acid baits starting no lower than 2 nucleic acid baits and ending no higher than 2000 nucleic acid baits.

Referring to Block 222, in some embodiments, the first subset of transcripts consists of two or more transcripts. In some embodiments, the first subset of transcripts consists of three or more transcripts. In some embodiments, the first subset of transcripts consists of four or more transcripts. In some embodiments, the first subset of transcripts consists of one or more, two or more, three or more, four or more, five or more, six or more, seven or more, eight or more, nine or more, or ten or more transcripts.

Referring to Block 224, in some embodiments, the another subset of transcripts, other than the first subset of transcripts, consists of two or more transcripts. In some embodiments, the another subset of transcripts consists of one or more, two or more, three or more, four or more, five or more, six or more, seven or more, eight or more, nine or more, or ten or more transcripts. In some embodiments, a respective subset of transcripts comprises at least 1, at least 2, at least 3, at least 4, at least 5, at least 6, at least 7, at least 8, at least 9, at least 10, at least 15, at least 20, at least 25, or at least 30 transcripts. In some embodiments, a respective subset of transcripts comprises no more than 50, no more than 40, no more than 30, no more than 20, no more than 10, or no more than 5 transcripts. In some embodiments, a respective subset of transcripts comprises from 2 to 5, from 3 to 10, from 5 to 15, from 2 to 20, or from 5 to 30 transcripts. In some embodiments, a respective subset of transcripts falls within another range starting no lower than 2 transcripts and ending no higher than 50 transcripts.

In some embodiments, the plurality of nucleic acid baits comprises at least $2 \times 10^3$, at least $3 \times 10^3$, at least $4 \times 10^3$, at least $5 \times 10^3$, at least $1 \times 10^4$, at least $2 \times 10^4$, at least $3 \times 10^4$, at least $4 \times 10^4$, at least $5 \times 10^4$, at least $6 \times 10^4$, at least $7 \times 10^4$, or at least $1 \times 10^5$ nucleic acid baits. In some embodiments, the plurality of nucleic acid baits comprises at least 10, at least 50, at least 100, at least 200, at least 300, at least 400, at least 500, at least 1000, at least 2000, at least 3000, at least 4000, at least 5000, at least 10,000, at least 20,000, at least 30,000, at least 40,000, at least 50,000, or at least 100,000 nucleic acid baits. In some embodiments, the plurality of nucleic acid baits comprises no more than 200,000, no more than 100,000, no more than 50,000, no more than 20,000, no more than 10,000, no more than 5000, no more than 4000, no more than 3000, no more than 2000, no more than 1000, no more than 500, or no more than 100 nucleic acid baits. In some embodiments, the plurality of nucleic acid baits is from 100 to 10,000, from 1000 to 6000, from 2000 to 5000, from 3000 to 4000, from 5000 to 20,000, from 20,000 to 50,000, or from 10,000 to 60,000 nucleic acid baits. In some embodiments, the plurality of nucleic acid baits falls within another range starting no lower than 10 nucleic acid baits and ending no higher than 200,000 nucleic acid baits.

As described above, each respective transcript in the corresponding plurality of transcripts of each respective gene in the plurality of genes is hybridizable to a nucleic acid bait in the plurality of nucleic acid baits. In other words, in some such embodiments, the plurality of nucleic acid baits spans all mature mRNA sequences, including UTRs and all annotated isoforms for each respective gene in the plurality of genes (e.g. each target gene in the plurality of target genes).

In some embodiments, the plurality of genes targeted by the plurality of nucleic acid baits (e.g., where the plurality of nucleic acid baits comprises, for each respective gene in the plurality of genes, at least 1 nucleic acid bait that hybridizes to at least one transcript of the respective gene) comprises any number of genes in the plurality of genes (as described, for instance, in the above section entitled, "Obtaining cDNA sequences"). For instance, in some embodiments, the plurality of genes targeted by the plurality of nucleic acid baits comprises at least 3, at least 5, at least 10, at least 20, at least 30, at least 40, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 15,000, at least 20,000, or at least 30,000 genes. In some embodiments, the plurality of genes targeted by the plurality of nucleic acid baits comprises no more than 100,000, no more than 50,000, no more than 10,000, no more than 5000, no more than 2000, no more than 1000, no more than 500, or no more than 100 genes. In some embodiments, the plurality of genes targeted by the plurality of nucleic acid baits is from 5 to 30,000, from 50 to 10,000, from 200 to 5000, or from 500 to 2000 genes. In some embodiments, the plurality of genes targeted by the plurality of nucleic acid baits falls within another range starting no lower than 3 genes and ending no higher than 100,000 genes.

Referring to Block 226, in some embodiments, the plurality of nucleic acid baits includes a minimum number of baits necessary to selectively hybridize to each respective transcript in the corresponding plurality of transcripts for a respective gene in the plurality of genes. For example, each respective transcript in the corresponding plurality of transcripts of each respective gene in the plurality of genes is hybridizable to at least one nucleic acid bait in the plurality of nucleic acid baits.

In some embodiments, the plurality of nucleic acid baits consists of a minimum number of baits necessary to selectively hybridize to each respective transcript in the corresponding plurality of transcripts for each respective gene in the plurality of genes. For example, each respective transcript in the corresponding plurality of transcripts of each respective gene in the plurality of genes is hybridizable to only one nucleic acid bait in the plurality of nucleic acid baits.

In some embodiments, the bait coverage (e.g., a number and/or ratio of nucleic acid baits, in the plurality of nucleic acid baits, that hybridizes to a respective gene and/or to each transcript in the plurality of transcripts that characterizes a respective gene) for each respective transcript in the plurality of transcripts, for each respective gene in the plurality of genes, is 1×. Thus, in some embodiments, each nucleic acid bait in the plurality of nucleic acid baits is hybridizable to a single transcript in the plurality of transcripts across the plurality of genes, and the number of nucleic acid baits in the plurality of nucleic acid baits is equal to the number of transcripts in the plurality of transcripts across the plurality of genes. In some embodiments, the bait coverage for each respective transcript in the plurality of transcripts for the respective gene is greater than 1×. Thus, in some embodiments, the plurality of nucleic acid baits comprises, for each respective transcript in the plurality of transcripts for a respective gene, greater than 1 nucleic acid bait that is hybridizable to the respective transcript. In some embodiments, the bait coverage for each respective transcript in the plurality of transcripts for the respective gene is at least 1×, at least 1.2×, at least 1.4×, at least 1.5×, at least 1.7×, at least 1.9×, at least 2×, at least 2.5×, at least 3×, at least 3.5×, at least 4×, at least 4.5×, at least 5×, at least 6×, at least 7×, at least 8×, at least 9×, at least 10X, at least 15×, at least 20×, at least 25×, at least 30×, at least 35×, at least 40×, at least 45×, or at least 50X. In some embodiments, the bait coverage for each respective transcript in the plurality of transcripts for the respective gene is no more than 80X, no more than 50X, no more than 40X, no more than 30X, no more than 20X, no more than 15×, no more than 10X, or no more than 5×. In some embodiments, the bait coverage for each respective transcript in the plurality of transcripts for the respective gene is from 1× to 10X, from 2× to 50X, from 10X to 30X, or another range starting no lower than 1× and ending no higher than 100X. In other words, in some embodiments, the plurality of nucleic acid baits comprises, for each respective transcript in the plurality of transcripts for a respective gene in the plurality of genes, a set of nucleic acid baits that is hybridizable to the respective transcript, where the set of nucleic acid baits includes at least 1, at least 2, at least 3, at least 4, at least 5, at least 6, at least 7, at least 8, at least 9, at least 10, at least 15, at least 20, at least 25, at least 30, at least 35, at least 40, at least 45, or at least 50 nucleic acid baits. In some embodiments, the set of nucleic acid baits that is hybridizable to the respective transcript includes no more than 80, no more than 50, no more than 40, no more than 30, no more than 20, no more than 15, no more than 10, or no more than 5 nucleic acid baits. In some embodiments, the set of nucleic acid baits that is hybridizable to the respective transcript includes from 1 to 10, from 2 to 50, or from 10 to 30 nucleic acid baits. In some embodiments, the set of nucleic acid baits that is hybridizable to the respective transcript falls within another range starting no lower than 1 nucleic acid baits and ending no higher than 80 nucleic acid baits.

In some embodiments, the bait coverage for each respective transcript in the plurality of transcripts, for each respective gene in the plurality of genes, is less than 1×. For instance, in some such embodiments, the plurality of nucleic acid baits includes, on average, less than 1 bait for each transcript in the plurality of transcripts for the respective gene (e.g., at least 1 nucleic acid bait in the plurality of nucleic acid baits hybridizes to two or more transcripts, in the plurality of transcripts, for the respective gene). In some embodiments, each nucleic acid bait in the plurality of nucleic acid baits is hybridizable to a plurality of transcripts, and the number of nucleic acid baits in the plurality of nucleic acid baits is less than the number of transcripts in the plurality of transcripts across the plurality of genes (see, for example, Example 1 below). In some embodiments, the bait coverage for each respective transcript in the plurality of transcripts for the first genetic target is less than 0.9×, less than 0.8×, less than 0.7×, less than 0.6×, less than 0.5×, less than 0.4×, less than 0.3×, less than 0.2×, less than 0.1×, less than 0.09×, less than 0.08×, less than 0.07×, less than 0.06×, less than 0.05×, less than 0.04×, less than 0.03×, less than 0.02×, or less than 0.01×. In some embodiments, the bait coverage for each respective transcript in the plurality of transcripts for the respective gene is no less than 0.005×, no less than 0.01×, no less than 0.05×, no less than 0.1×, no less than 0.2×, no less than 0.3×, no less than 0.4×, or no less than 0.5×. In some embodiments, the bait coverage for each respective transcript in the plurality of transcripts for the respective gene is from 0.01× to 0.1×, from 0.05× to 0.3×, from 0.05× to 0.5×, or another range starting no lower than 0.005× and ending no higher than 1×. In other words, in some embodiments, a respective nucleic acid bait in the plurality of nucleic acid baits hybridizes to a set of transcripts, in the plurality of transcripts, for a respective gene in the plurality of genes, where the set of transcripts includes at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or at least 100 transcripts. In some embodiments, a respective nucleic acid bait is hybridizable to a set of transcripts that includes no more than 200, no more than 100, no more than 50, no more than 30, no more than 20, no more than 15, no more than 10, or no more than 5 transcripts. In some embodiments, a respective nucleic acid bait is hybridizable to a set of transcripts that includes from 1 to 10, from 2 to 50, or from 10 to 100 transcripts. In some embodiments, a respective nucleic acid bait is hybridizable to a set of transcripts including another range of transcripts starting no lower than 1 transcript and ending no higher than 200 transcripts.

In some embodiments, for a respective gene in the plurality of genes, the bait coverage for each respective transcript in the plurality of transcripts for the respective gene is 1× or more than 1×. In some embodiments, for a respective gene in the plurality of genes, the bait coverage for each respective transcript in the plurality of transcripts for the respective gene is less than 1×. In some embodiments, for a respective gene in the plurality of genes, the bait coverage for the respective gene is 1× (e.g., the plurality of nucleic acid baits comprises 1 nucleic acid bait that is hybridizable to the plurality of transcripts for the respective gene only) or more than 1× (e.g., the plurality of nucleic acid baits comprises more than 1 nucleic acid bait that is hybridizable to the plurality of transcripts for the respective gene). In some embodiments, for a respective gene in the plurality of genes, the bait coverage for the respective gene is less than 1× (e.g., the plurality of nucleic acid baits comprises at least 1 nucleic acid bait that hybridizes to the plurality of transcripts for two or more genes in the plurality of genes).

In some embodiments, a first gene in the plurality of genes has a bait coverage that is the same or different from a second gene in the plurality of genes. For instance, in an example embodiment, the bait coverage for each respective transcript in the plurality of transcripts for a first gene in the plurality of genes is 1× (e.g., the plurality of nucleic acid baits comprises, for each respective transcript in the plurality of transcripts for the first gene, 1 nucleic acid bait that is hybridizable only to the respective transcript), and the bait coverage for each respective transcript in the plurality of transcripts for a second gene in the plurality of genes is less than 1× (e.g., the plurality of nucleic acid baits comprises at least 1 nucleic acid bait that hybridizes to two or more transcripts, in the plurality of transcripts, for the second gene). In another example embodiment, the bait coverage for each respective transcript in the plurality of transcripts for a first gene in the plurality of genes is 0.8× or less, and the bait coverage for each respective transcript in the plurality of transcripts for a second gene in the plurality of genes is 0.2× or less. Furthermore, in some implementations, for a respective gene in the plurality of genes, the plurality of nucleic acid baits includes a corresponding set of nucleic acid baits that is minimally, partially, or fully tiled across the plurality of cDNA sequences mapping to the respective gene, or a hybrid thereof. For instance, as described above, the plurality of transcripts corresponding to a respective gene can be subdivided into one or more subsets of transcripts, each subset of transcripts hybridizable to a corresponding one or more nucleic acid baits. Thus, in some embodiments, each respective gene in the plurality of genes has the same or different number of subsets of transcripts and, for each respective subset of transcripts, the same or different number of corresponding nucleic acid baits, as any other respective gene in the plurality of genes. Furthermore, in some embodiments, each respective gene in the plurality of genes has the same or different number of nucleic acid baits (e.g., minimal, full, or hybrid) that selectively hybridizes to a cDNA sequence mapping to the respective gene, as any other respective gene in the plurality of genes.

In some embodiments, for a respective gene in the plurality of genes, the plurality of nucleic acid baits includes a set of nucleic acid baits that is fully tiled across the respective gene. In other words, in some such embodiments, the set of nucleic acid baits for the respective gene exhaustively represents the cDNA sequences of the respective gene (e.g., as a series of k-mers, where each bait is a different k-mer as explained below). For instance, in some embodiments, the set of nucleic acid baits that is fully tiled across the respective gene is obtained by a method comprising obtaining a respective candidate hybridization sequence of the respective gene, where, when a length of the coding sequence of the respective gene satisfies a predetermined length threshold, the candidate hybridization sequence is the coding sequence of the respective gene, and when the length of the coding sequence of the respective gene does not satisfy a predetermined length threshold, the candidate hybridization sequence is an mRNA sequence of the respective gene. In some embodiments, the method further comprises, for each respective sub-sequence of length K residues of the respective candidate hybridization sequence, including a nucleic acid bait corresponding to the respective sub-sequence of length K residues in the plurality of nucleic acid baits. Thus, in some such embodiments, the method for obtaining a set of nucleic acid baits that is fully tiled across the respective gene comprises obtaining a plurality of sub-sequences of length K residues, where the plurality of sub-sequences of length K residues (e.g., k-mers) represents every possible k-mer across a coding sequence and/or an mRNA sequence of the respective gene. In some embodiments, the plurality of sub-sequences of length K residues (e.g., k-mers) represents, for each respective allele in a plurality of alleles of the respective gene, a nucleic acid sequence corresponding to the respective allele. For instance, in some embodiments, the plurality of sub-sequences of length K residues (e.g., k-mers) represents, for each respective allele in a plurality of alleles of the respective gene, every possible k-mer across the nucleic acid sequence corresponding to the respective allele. In some embodiments, the plurality of sub-sequences of length K residues (e.g., k-mers) represents, for each respective allele in a plurality of alleles represented by a plurality of transcripts for the respective gene, a nucleic acid sequence corresponding to the respective allele. For instance, in some embodiments, the plurality of sub-sequences of length K residues (e.g., k-mers) represents, for each respective allele in a plurality of alleles for the respective gene, every possible k-mer across each respective transcript in the plurality of transcripts that corresponds to the respective allele. In some embodiments, there are one or more, two or more, three or more, five or more, six or more, seven or more, eight or more, nine or more, or 10 or more alleles in the plurality of alleles for the respective gene.

In some embodiments, the respective gene has a corresponding fully-tiled set of nucleic acid baits, where each possible k-mer of length K, for each transcript in the plurality of transcripts that characterizes the respective gene, is represented by a respective nucleic acid bait in the plurality of nucleic acid baits. In some embodiments, the respective gene has a corresponding fully-tiled set of nucleic acid baits, where each possible k-mer of length K, for a respective nucleic acid sequence corresponding to the respective gene (e.g., a coding sequence, an mRNA sequence, and/or a genomic sequence), is represented by a respective nucleic acid bait in the plurality of nucleic acid baits. In some embodiments, the respective gene has a corresponding fully-tiled set of nucleic acid baits, where each possible k-mer of length K, for each cDNA sequence, in the plurality of cDNA sequences, mapping to the respective gene, is represented by a respective nucleic acid bait in the plurality of nucleic acid baits.

In some embodiments, for a respective gene in the plurality of genes, the plurality of nucleic acid baits includes a set of nucleic acid baits that is minimally tiled across the respective gene (e.g., the minimum number of baits necessary to selectively hybridize to each respective transcript in the corresponding plurality of transcripts for the respective gene). In some embodiments, the minimally-tiled set of nucleic acid baits is obtained through a method for hybridization/capture probe design, as described herein and in accordance with some embodiments of the present disclosure (see, for example, Section II. Methods for Hybridization/Capture Probe Design). For instance, as further described below, in some embodiments, at least one nucleic acid bait in the plurality of nucleic acid baits that hybridizes to a cDNA sequence mapping to a respective gene in the plurality of genes (i) selectively hybridizes to a first subset of transcripts, in a corresponding plurality of subsets of transcripts in the plurality of transcripts corresponding to the respective gene, where the first subset of transcripts comprises the maximal number of transcripts that hybridize to a nucleic acid bait of length between $K_1$ and $K_2$, or (ii) selectively hybridizes to a second subset of transcripts, where the second subset of transcripts comprises the maximal number of transcripts, other than the first subset of transcripts, in the corresponding plurality of subsets of transcripts in the plurality of transcripts corresponding to the respective gene, that hybridize to a nucleic acid bait of length between $K_1$ and $K_2$.

In some embodiments, for a respective gene in the plurality of genes, the plurality of nucleic acid baits includes a set of nucleic acid baits that is partially tiled (e.g., fewer nucleic acid baits than a fully-tiled bait set but more nucleic acid baits than a minimally-tiled bait set) across the respective gene. In some embodiments, the partially-tiled set of nucleic acid baits is obtained through a method for hybridization/capture probe design, as described herein and in accordance with some embodiments of the present disclosure (see, for example, Section II. Methods for Hybridization/Capture Probe Design), where at least 1 additional nucleic acid bait is further included in the identified plurality of nucleic acid baits. For instance, in some embodiments, the partially-tiled set of nucleic acid baits is obtained by a method comprising identifying the minimum number of baits necessary to selectively hybridize to each respective transcript in the corresponding plurality of transcripts for the respective gene, and further adding, to the identified plurality of nucleic acid baits, at least 1 additional nucleic acid bait that selectively hybridizes to at least 1 transcript in the corresponding plurality of transcripts for the respective gene.

In some embodiments, for a respective gene in the plurality of genes, the plurality of nucleic acid baits includes a set of nucleic acid baits that is obtained using any other method for identifying and/or obtaining nucleic acid baits for a respective gene known in the art, or any substitutions, modifications, additions, deletions, and/or combinations thereof, as will be apparent to one skilled in the art.

As described above, in some embodiments, a first gene in the plurality of genes has a bait coverage (e.g., a number and/or ratio of nucleic acid baits, in the plurality of nucleic acid baits, that hybridizes to a respective gene and/or to each transcript in the plurality of transcripts that characterizes a respective gene) that is the same or different from a second gene in the plurality of genes. In some embodiments, each gene in a first subset of genes in the plurality of genes has a bait coverage (e.g., a set of nucleic acid baits, in the plurality of nucleic acid baits, that hybridizes to each transcript in the plurality of transcripts that characterizes the respective gene) that is the same or different from each gene in a second subset of genes in the plurality of genes.

For instance, in some embodiments, each gene in a first subset of genes, in the plurality of genes, is selectively hybridized to by a respective minimally-tiled nucleic acid bait set for the respective gene. In some embodiments, the respective minimally-tiled bait set for the respective gene is obtained using any of the methods disclosed herein, or any substitutions, modifications, additions, deletions, and/or combinations thereof, as will be apparent to one skilled in the art. In some embodiments, each gene in a second subset of genes, in the plurality of genes, is selectively hybridized to by a respective fully-tiled nucleic acid bait set for the respective gene. In some embodiments, the respective fully-tiled bait set for the respective gene is obtained using any of the methods described above.

Alternatively or additionally, in some embodiments, each gene in a subsequent subset of genes in the plurality of genes, other than the first subset of genes, is selectively hybridized to by a respective partially-tiled (e.g., less than fully-tiled but more than minimally-tiled) nucleic acid bait set for the respective gene. In some embodiments, the respective partially-tiled bait set for the respective gene is obtained using any of the methods described above. Alternatively or additionally, in some embodiments, each gene in a subsequent subset of genes in the plurality of genes, other than the first subset of genes, is selectively hybridized to by a respective nucleic acid bait set for the respective gene obtained using any other method of obtaining nucleic acid baits for a respective gene known in the art, as described above.

In some embodiments, the first subset of genes comprises at least 3, at least 5, at least 10, at least 20, at least 30, at least 40, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 15,000, at least 20,000, or at least 30,000 genes. In some embodiments, the first subset of genes comprises no more than 100,000, no more than 50,000, no more than 10,000, no more than 5000, no more than 2000, no more than 1000, no more than 500, or no more than 100 genes. In some embodiments, the first subset of genes is from 5 to 30,000, from 50 to 10,000, from 200 to 5000, or from 500 to 2000 genes. In some embodiments, the first subset of genes falls within another range starting no lower than 3 genes and ending no higher than 100,000 genes.

In some embodiments, the first subset of genes comprises a percentage X of the plurality of genes. In some embodiments, X is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95%. In some embodiments, X is no more than 99, no more than 98, no more than 95, no more than 90, no more than 80, no more than 70, no more than 60, no more than 50, no more than 40, no more than 30, or no more than 20%. In some embodiments, X is from 20 to 90, from 50 to 100, from 10 to 60, or from 15 to 99%. In some embodiments, X falls within another range starting no lower than 5% and ending no higher than 100%.

In some embodiments, the second subset of genes and/or any subsequent subset of genes in the plurality of genes, other than the first subset of genes, comprises a percentage that is 1−X of the genes in the plurality of genes. For instance, in some embodiments, each respective gene in a subset of X genes in the plurality of genes is selectively hybridized to by a respective minimally-tiled nucleic acid bait set for the respective gene. In some embodiments, each respective gene in the subset of X genes in the plurality of genes is selectively hybridized to by a respective fully-tiled nucleic acid bait set for the respective gene. In some embodiments, each respective gene in a subset of X genes in the plurality of genes is selectively hybridized to by a respective partially-tiled nucleic acid bait set for the respective gene. In some embodiments, the subset of X genes in the plurality of genes includes a combination of genes selectively hybridized to by respective minimally-tiled nucleic acid bait sets, genes selectively hybridized to by respective fully-tiled nucleic acid bait sets, and genes selectively hybridized to by respective partially-tiled nucleic acid bait sets. In some embodiments, each gene in a subset 1−X genes (where the quantities X and 1−X sum to 100 percent of the plurality of genes), in the plurality of genes, is selectively hybridized to by a respective minimally-tiled nucleic acid bait set for the respective gene. In some embodiments, each respective gene in the subset of 1−X genes in the plurality of genes is selectively hybridized to by a respective fully-tiled nucleic acid bait set for the respective gene. In some embodiments, each respective gene in a subset of 1−X genes in the plurality of genes is selectively hybridized to by a respective partially-tiled nucleic acid bait set for the respective gene. In some embodiments, the subset of 1−X genes in the plurality of genes includes a combination of genes selectively hybridized to by respective minimally-tiled nucleic acid bait sets, genes selectively hybridized to by respective fully-tiled nucleic acid bait sets, and genes selectively hybridized to by respective partially-tiled nucleic acid bait sets. In some embodiments, each respective gene in the subset of X genes in the plurality of genes is selectively hybridized to by a respective minimally-tiled nucleic acid bait set for the respective gene, and each respective gene in the subset of 1−X genes in the plurality of genes is selectively hybridized to by a respective fully-tiled nucleic acid bait set for the respective gene. In some embodiments, each respective gene in the subset of X genes in the plurality of genes is selectively hybridized to by a respective minimally-tiled nucleic acid bait set for the respective gene, and each respective gene in the subset of 1−X genes in the plurality of genes is selectively hybridized to by a respective partially-tiled nucleic acid bait set for the respective gene. In some embodiments, each respective gene in the subset of X genes in the plurality of genes is selectively hybridized to by a respective minimally-tiled nucleic acid bait set for the respective gene, and the subset of 1−X genes in the plurality of genes includes a combination of genes selectively hybridized to by respective fully-tiled nucleic acid bait sets and genes selectively hybridized to by respective partially-tiled nucleic acid bait sets.

Thus, for example, in some embodiments, the plurality of nucleic acid baits is a mixed or hybrid nucleic acid bait set that includes one or more of exhaustively represented, partially tiled, and/or minimally tiled nucleic acid baits for a corresponding one or more genes in the plurality of genes.

Referring to Block 228, in some embodiments, $K_1$ is 25 and $K_2$ is 1000. In some embodiments, $K_1$ is 50 and $K_2$ is 500. In some embodiments, $K_1$ is 90 and $K_2$ is 150. In some embodiments, $K_1$ is 95 and $K_2$ is 130. In some embodiments, $K_1$ is the same value of $K_2$. In some such embodiments, $K_1$ is 100 or 120. In some embodiments, $K_1$ and $K_2$ are different positive integers.

Thus, in some embodiments, a respective nucleic acid bait in the plurality of nucleic acid baits is at least 10, at least 20, at least 30, at least 40, at least 50, at least 60, at least 70, at least 80, at least 90, at least 100, at least 120, at least 150, at least 200, at least 300, at least 400, at least 500, at least 600, at least 700, at least 800, at least 900, or at least 1000 base pairs (bp) in length. In some embodiments, a respective nucleic acid bait in the plurality of nucleic acid baits is no more than 2000, no more than 1000, no more than 800, no more than 600, no more than 500, no more than 400, no more than 300, no more than 200, no more than 100, or no more than 50 bp in length. In some embodiments, a respective nucleic acid bait in the plurality of nucleic acid baits is from 10 to 800, from 20 to 500, from 50 to 300, from 100 to 200, from 80 to 160, or from 100 to 140 bp in length. In some embodiments, a respective nucleic acid bait in the plurality of nucleic acid baits has a length falling within another range starting no lower than 10 bp and ending no higher than 2000 bp.

In some embodiments, each respective nucleic acid bait in the plurality of nucleic acid baits shares less than a threshold percentage of sequence identity to any other nucleic acid bait in the plurality of nucleic acid baits. For instance, in some embodiments, each respective nucleic acid bait in the plurality of nucleic acid baits shares less than 100 percent, less than 98 percent, less than 96 percent, less than 94 percent, less than 92 percent, less than 90 percent, less than 88 percent, less than 86 percent, less than 84 percent, less than 82 percent, less than 80 percent, less than 70 percent, less than 60 percent, less than 50 percent, or less than 40 percent identity to any other nucleic acid bait in the plurality of nucleic acid baits. In some embodiments, the threshold percentage of sequence identity is ten percent, twenty percent, thirty percent, or between five and fifty percent.

In some embodiments, the threshold of shared sequence identity between a respective nucleic acid bait in the plurality of nucleic acid baits to any other nucleic acid bait in the plurality of nucleic acid baits determines the level of cross-hybridization of each respective nucleic acid bait to off-target sequence reads.

In some embodiments, each respective nucleic acid bait in the plurality of nucleic acid baits comprises a nucleic acid sequence that has a minimal identity to the reference genome of at least 90%. In some embodiments, each respective nucleic acid bait in the plurality of nucleic acid baits comprises a nucleic acid sequence that has a minimal identity to the reference genome of at least 90%, at least 91%, at least 92%, at least 93%, at least 94%, at least 95%, at least 96%, at least 97%, at least 98%, or at least 99%.

In some embodiments, each respective nucleic acid bait in the plurality of nucleic acid baits that hybridizes to a transcript in the plurality of transcripts of the respective gene has a melting temperature (Tm) with respect to the transcript that is between a first threshold temperature and a second threshold temperature. In some such embodiments, the first threshold temperature is between 65° C. and 85° C. and the second threshold temperature is between 90° C. and 110° C. In some such embodiments, the first threshold temperature is 75° C. and the second threshold temperature is 100° C. In some embodiments, each respective nucleic acid bait in the plurality of nucleic acid baits that hybridizes to a transcript in the plurality of transcripts of the respective gene that has a Tm below the first threshold temperature or above the second threshold temperature is removed (e.g., filtered) from the plurality of nucleic acid baits.

In some embodiments, each respective nucleic acid bait in the plurality of nucleic acid baits hybridizes to a region of the respective gene that is at least a minimum threshold distance away from any annotated start and/or stop sites of the respective gene.

In some embodiments, a respective nucleic acid bait in a plurality of nucleic acid baits for a respective sequence read in a plurality of sequence reads (e.g., transcripts, coding sequences, mRNA sequences, cDNA sequences, etc.) mapping to a respective gene is located at a position that is at least a minimum threshold distance from the 3' end (e.g., including any 3' annotations) of the respective sequence read. In some such embodiments, off-target hybridization of a respective nucleic acid bait to a respective cDNA sequence can occur where there are unannotated poly-A sites or poly-A sequences present in the genomic exon and/or mRNA sequence that cause oligo-dT mispriming. As a result, in some such embodiments, the optimal position for nucleic acid bait hybridization to a corresponding cDNA sequence is located at a position that is at least a minimum threshold distance from the 3' end (e.g., including any 3' annotations).

In some embodiments, a respective nucleic acid bait in a plurality of nucleic acid baits for a respective sequence read in a plurality of sequence reads (e.g., transcripts, coding sequences, mRNA sequences, cDNA sequences, etc.) mapping to a respective gene is located at a position that is at least a minimum threshold distance from the 5' end of the respective sequence read (e.g., including any 5' annotations).

Non-limiting examples of a minimum threshold distance (e.g., from any annotated start and/or stop sites, any 3' end, and/or any 5' end of a respective sequence read) are from 100 to 200 base pairs (bp), from 200 to 300 bp, from 300 to 400 bp, from 400 to 500 bp, from 500 to 600 bp, from 600 to 700 bp, from 700 to 800 bp, from 800 to 900 bp, from 900 to 1000 bp, or more than 1000 bp. In some embodiments, the minimum threshold distance is at least 20, at least 30, at least 40, at least 50, at least 100, at least 200, at least 300, at least 400, at least 500, at least 600, at least 700, at least 800, at least 900, or at least 1000 bp. In some embodiments, the minimum threshold distance is no more than 2000, no more than 1000, no more than 800, no more than 500, no more than 300, no more than 200, or no more than 100 bp. In some embodiments, the minimum threshold distance is from 20 to 2000 bp, from 100 to 1000 bp, or from 200 to 800 bp. In some embodiments, the minimum threshold distance falls within another range starting no lower than 20 bp and ending no higher than 2000 bp.

In some embodiments, the percentage of cDNA sequences that preferentially hybridize to nucleic acid baits at positions at least a minimum threshold distance away (e.g., from any annotated start and/or stop sites, any 3' end (e.g., including any 3' annotations), and/or any 5' end (e.g., including any 5' annotations) of a respective sequence read (e.g., transcripts, coding sequences, mRNA sequences, cDNA sequences, etc.) mapping to the respective gene) is between 0% and 10%, between 10% and 20%, or between 20% and 30%. In addition, in some embodiments, the method further comprises removing (e.g., filtering), from the plurality of nucleic acid baits, one or more nucleic acid baits comprising unannotated poly-A sites or poly-A sequences in the mRNA sequence.

Referring to Block 230, in some embodiments, each respective substring of fixed length P nucleotides in each respective nucleic acid bait in the plurality of nucleic acid baits is represented in the reference genome less than a threshold number of times L.

Referring to Block 232, in some such embodiments, P is at least 15 nucleotides. In some embodiments, P is at least 25 nucleotides. In some embodiments, P is at least 5, at least 10, at least 15, at least 20, at least 25, at least 30, at least 35, at least 40, at least 45, at least 50, or at least 100 nucleotides. In some embodiments, P is no more than 200, no more than 100, no more than 80, no more than 50, no more than 40, no more than 30, or no more than 20 nucleotides. In some embodiments, P is from 5 to 150, from 5 to 100, from 10 to 50, or from 20 to 40 nucleotides. In some embodiments, P falls within another range starting no lower than 5 nucleotides and ending no higher than 200 nucleotides.

Referring to Block 234, in some embodiments, L is between 2 and 50. In some embodiments, L is less than 20, less than 10, or less than 5. In some embodiments, L is no more than 800, no more than 500, no more than 200, no more than 100, no more than 80, no more than 50, no more than 40, no more than 30, no more than 20, no more than 10, or no more than 5. In some embodiments, L is from 2 to 100, from 5 to 80, from 10 to 50, from 20 to 500, or from 5 to 200. In some embodiments, L falls within another range starting no lower than 5 and ending no higher than 800.

In some embodiments, P is less than K. In some embodiments, P is equal to K.

In some embodiments, such a uniqueness requirement reduces the hybridization of each nucleic acid bait to off-target locations in the reference genome.

Referring to Block 236, in some embodiments, the method further comprises modifying a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L. The modifying comprises (i) removing the respective nucleic acid bait from the plurality of nucleic acid baits, (ii) truncating the respective nucleic acid bait such that the respective nucleic acid bait is represented in the reference genome at a position that is at least M base pairs away from any portion of the reference genome that comprises the substring of fixed length P, or (iii) shifting the respective sequence of the nucleic acid bait along the reference genome such that the respective sequence of the nucleic acid bait is represented in the reference genome at a position that is at least M base pairs away from any portion of the reference genome that comprises the substring of fixed length P.

Referring to Block 238, in some embodiments, P is between 10 and 75. In some embodiments, P is between 20 and 50 or between 37 and 43. In some embodiments, P is at least 5, at least 10, at least 15, at least 20, at least 25, at least 30, at least 35, at least 40, at least 45, at least 50, or at least 100 nucleotides. In some embodiments, P is no more than 200, no more than 100, no more than 80, no more than 50, no more than 40, no more than 30, or no more than 20 nucleotides. In some embodiments, P is from 5 to 150, from 5 to 100, from 10 to 50, or from 20 to 40 nucleotides. In some embodiments, P falls within another range starting no lower than 5 nucleotides and ending no higher than 200 nucleotides.

Referring to Block 240, in some embodiments, L is between 2 and 1000. In some embodiments, L is between 5 and 500, between 10 and 100, between 20 and 50, or between 23 and 27. In some embodiments, L is no more than 800, no more than 500, no more than 200, no more than 100, no more than 80, no more than 50, no more than 40, no more than 30, no more than 20, no more than 10, or no more than 5. In some embodiments, L is from 2 to 100, from 5 to 80, from 10 to 50, from 20 to 500, or from 5 to 200. In some embodiments, L falls within another range starting no lower than 5 and ending no higher than 800.

Referring to Block 242, in some embodiments, the method further comprises designing a nucleic acid bait in the plurality of nucleic acid baits for a respective gene in the plurality of genes using, when the length of the coding sequence of the respective gene satisfies a predetermined length threshold, the coding sequence of the respective gene, and when the length of the coding sequence of the respective gene does not satisfy a predetermined length threshold, an mRNA sequence of the respective gene. For example, each respective nucleic acid bait can be hybridized to a respective gene (e.g., a transcript of a respective gene) at a region of the gene that is fully encompassed by one or more coding sequences of the gene. Alternatively, each respective nucleic acid bait can be hybridized to a respective gene at a region of the gene that comprises all or a portion of one or more coding sequences of the gene but is not fully encompassed by one or more coding sequences of the gene. In some embodiments, the region of the respective gene is the mRNA sequence of the respective gene.

Referring to Block 244, in some embodiments, the method further comprises filtering the plurality of nucleic acid baits for mappability, absence of repetitive subsequences, and/or overall GC content.

Regions of low mappability refer to the similarity of the respective region to other sequences. For example, a respective nucleic acid bait in a plurality of nucleic acid baits in a low mappability region will hybridize to off-target sequences in addition to the respective target sequence (e.g., a transcript of a respective gene) in the plurality of target sequences for which the nucleic acid bait was designed. In some embodiments, a nucleic acid bait in a low mappability region will hybridize to a plurality of cDNA sequences (e.g., multi-pull-down). Thus, in some embodiments, filtering for mappability increases the specificity or accuracy of the hybridization/capture approach. For discussion on mappability, see Wentian et al., 2014, "Diminishing return for increased Mappability with longer sequencing reads: implications of the k-mer distributions in the human genome," BMC Bioinformatics 15(2), which is hereby incorporated by reference. In other examples, nucleic acid baits corresponding to target sequences comprising repetitive subsequences or low GC content result in additional sources of off-target hybridization, such that filtering the respective nucleic acid baits improves specificity.

In some embodiments, a respective nucleic acid bait in the plurality of nucleic acid baits is single-stranded. In some embodiments, each respective nucleic acid bait in the plurality of nucleic acid baits is single-stranded.

Hybridization/Capture

Generally, hybridization and capture of nucleic acid molecules (e.g., cDNA molecules and/or fragments) by nucleic acid baits is performed to enrich libraries, such as gene expression libraries, for relevant genes, thus decreasing sequencing requirements. In some cases, sequencing requirements after enrichment by hybridization and capture methods are decreased by up to 90%. In an example embodiment, target enrichment is achieved by a hybrid/capture workflow, in which gene-specific, biotinylated nucleic acid baits are hybridized to their complement in a library (including, e.g., a plurality of unfragmented cDNA molecules), bound to streptavidin beads, and washed to remove non-targeted library molecules. The bead-bound, targeted library sequences (e.g., unfragmented cDNA molecules) are amplified to produce sequencing-ready libraries. Additionally, enriched, amplified cDNA sequences can be processed post-enrichment, including fragmentations, end-repair, A-tailing, adapter ligation, and SI—PCR. Nucleic acid baits for use in hybridization and capture for enrichment of nucleic acid molecules include any of the embodiments of nucleic acid baits disclosed herein, as described in the foregoing section entitled, "Nucleic Acid Baits." Methods for hybridization and capture of nucleic acid molecules that are contemplated in the present disclosure include, but are not limited to, any methods known in the art. Example methods for hybridization and capture of nucleic acid molecules are described in further detail in Example 2 below, with reference to FIGS. 8A and 8B, and in 10X Genomics, 2021, "Targeted Gene Expression—Single Cell User Guide", Document Number CG000293, Rev E, which is hereby incorporated herein by reference in its entirety.

In some embodiments, the forming the plurality of nucleic acid bait—sequence read complexes comprises hybridizing each cDNA sequence in the first subset of cDNA sequences (e.g., in a library of cDNA sequences) to one or more nucleic acid baits in the plurality of nucleic acid baits.

In some embodiments, each cDNA sequence in the first subset of cDNA sequences includes all or a portion of a sequence of an analyte of interest (e.g., a gene and/or a gene product; see, for instance, Definitions: "Nucleic Acid Analytes," above) or a complement thereof.

In some embodiments, each nucleic acid bait in the plurality of nucleic acid baits is hybridized with a transcript in the plurality of transcripts corresponding to a respective gene at about 40° C., about 45° C., about 50° C., about 55° C., about 60° C., about 65° C., about 70° C., about 75° C., about 80° C. or higher. In some embodiments, each nucleic acid bait in the plurality of nucleic acid baits is hybridized with a transcript in the plurality of transcripts corresponding to a respective gene for at least 15 minutes, at least 30 minutes, at least 45 minutes, at least 1 hour, at least 90 minutes, at least 2 hours, at least 3 hours, at least 4 hours at least 5 hours, or longer.

In some embodiments, each cDNA sequence in the plurality of cDNA sequences that hybridizes to a nucleic acid bait (e.g., each nucleic acid bait—sequence read complex) is enriched. In some such embodiments, enrichment is performed by degrading unhybridized cDNA sequences (e.g., by a nuclease), thus enriching the hybridized nucleic acid bait-sequence read complexes. In some embodiments, each cDNA sequence in the plurality of cDNA sequences that does not hybridize to a nucleic acid bait is enriched. In some such embodiments, hybridized nucleic acid bait—sequence read complexes are degraded (e.g., by a nuclease), thus enriching the unhybridized nucleic acids; for example, this technique is useful, in some implementations, to decrease the amount of a high-abundance cDNA sequence that is not of interest.

Referring to Block 246, the method further comprises selectively capturing the plurality of nucleic acid bait—sequence read complexes.

For example, each cDNA sequence in the plurality of cDNA sequences that hybridizes to a nucleic acid bait (e.g., each nucleic acid bait—sequence read complex) is enriched by capturing each nucleic acid bait—sequence read complex (e.g., hybrid/capture).

Referring to Block 248, in some embodiments, the selectively capturing the plurality of nucleic acid bait—sequence read complexes captures the plurality of nucleic acid bait—sequence read complexes to a solid support. In some embodiments, the solid support is any of the embodiments of substrates and/or features described above (see, Definitions). In some embodiments, the solid support comprises a bead.

In some such embodiments, each nucleic acid bait in the plurality of nucleic acid baits comprises a non-nucleotide binding moiety, the solid support comprises a plurality of capture moieties, and a respective nucleic acid bait—sequence read complex is captured on the solid support through a reaction between a capture moiety in the plurality of capture moieties and the corresponding binding moiety of the respective nucleic acid bait—sequence read complex. In some embodiments, a capture moiety in the plurality of capture moieties comprises streptavidin and the corresponding non-nucleotide binding moiety comprises biotin, 2-(4-Hydroxyphenylazo)benzoic acid (HABA), or a compound listed in Table 1 (see, Definitions). For example, in some embodiments, a nucleic acid bait includes a molecular tag, and a nucleic acid bait—sequence read complex is enriched using an agent that binds specifically to the molecular tag.

In some embodiments, the non-nucleotide binding moiety is attached (directly or indirectly) to a substrate (e.g., a slide, a well, or a bead). In some embodiments, a non-nucleotide binding moiety comprises a protein, a nucleic acid, a carbohydrate, a small molecule, and/or any combination thereof. In some embodiments, a capture moiety that binds specifically to a non-nucleotide binding moiety comprises a protein, a nucleic acid, a carbohydrate, a small molecule, and/or any combination thereof. In some embodiments, a non-nucleotide binding moiety is streptavidin and a capture moiety that binds specifically to the non-nucleotide binding moiety is biotin. In some embodiments, a non-nucleotide binding moiety is biotin and a capture moiety that binds specifically to the non-nucleotide binding moiety is streptavidin (e.g., streptavidin attached to a bead).

In some embodiments, the non-nucleotide binding moiety is attached to the 5' or the 3' end of a respective nucleic acid bait. For instance, in some embodiments, each nucleic acid bait in the plurality of nucleic acid baits is an oligonucleotide with a 5' biotin modification.

In some embodiments, where the non-nucleotide binding moiety is biotin and the method includes the use of streptavidin beads to enrich a nucleic acid bait—sequence read complex (e.g., a pull-down method), the streptavidin beads are washed using any method known in the art. In some embodiments, the streptavidin beads are washed for 1 time, 2 times, 3 times, 4 times, 5 times, 6 times, 7 times or more. In some embodiments, the streptavidin beads are stringently washed for one time, 2 times, 3 times, 4 times, 5 times, 6 times, 7 times, or more. In some embodiments, the streptavidin beads are washed at about 15° C., about 20° C., about 25° C., about 30° C., about 35° C., about 40° C., about 45° C., about 48° C., about 50° C., or more. In some embodiments, after one or more wash steps, the nucleic acid bait—sequence read complex is recovered and is thus enriched.

In some embodiments, the enriched cDNA sequences are released (e.g., dissociated) from nucleic acid baits and purified to remove streptavidin and biotin (or any other non-nucleotide binding moiety and/or capture moiety that binds specifically to the non-nucleotide binding moiety). In some embodiments, a plurality of nucleic acid baits is used in any of the methods described herein to enrich one or more nucleic acids of interest from a plurality of nucleic acids. In some embodiments, each nucleic acid bait in the plurality of nucleic acid baits is designed to enrich one or more nucleic acids that include all or a part of a sequence of an analyte of interest (e.g., one or more genes that function or are aberrantly expressed in a particular cellular state or pathway; see, for instance, Definitions: "Nucleic Acid Analytes," above), or a complement thereof.

In some embodiments, one or more detectable moieties is associated (e.g., attached directly or indirectly) with each nucleic acid bait in the plurality of nucleic acid baits. In some embodiments, the one or more detectable moieties is used to detect (or enhance detection) of a nucleic acid bait (e.g., a nucleic acid bait—sequence read complex). In some alternative embodiments, the nucleic acid baits do not include a detectable moiety.

In some embodiments, the hybridization and capture of the plurality of transcripts with the plurality of nucleic acid baits comprises incubating the plurality of transcripts and the plurality of nucleic acid baits with one or more blockers (e.g., universal blockers and/or Cot DNA).

In some embodiments, the plurality of cDNA sequences (before or after enrichment using a plurality of nucleic acid baits), a subset thereof, or a library generated from the same is dried. In some embodiments, drying includes a dehydrating process such as heat, a vacuum, lyophilization, desiccation, filtration, and air-drying. In some embodiments, drying is performed for at least 1 hour, at least 2 hours, at least 3 hours or at least 4 hours. In some embodiments, the plurality of cDNA sequences (before or after enrichment using a bait oligonucleotide), a subset thereof, or a library generated from the same is not dried.

Analysis and Applications

Referring to Block 250, the method further comprises analyzing the plurality of nucleic acid bait—sequence read complexes captured by the selectively capturing described above.

Referring to Block 252, the analyzing the plurality of nucleic acid bait—sequence read complexes captured by the selectively capturing comprises sequencing of nucleic acid bait—sequence read complexes captured as described above.

In some embodiments, the sequencing comprises determining all or a portion of the sequence of one or more analytes (e.g., a gene and/or a gene product; see, for instance, Definitions: "Nucleic Acid Analytes," above) from the biological sample or a complement thereof in the nucleic acid.

In some embodiments, the sequencing is a short read-length sequencing reaction or a long read-length sequencing reaction. For instance, in some embodiments, the sequencing reaction is a short-read, high-accuracy sequencing reaction. In some embodiments, the short read-length sequencing reaction comprises a targeted short-read Illumina cDNA library. In some other embodiments, the sequencing reaction is a long read-length sequencing reaction and makes use of cDNA sequences with adaptors added. In some such embodiments, the long read-length sequencing reaction comprises direct DNA and/or RNA sequencing. In some embodiments, the sequencing reaction is a long read-length sequencing reaction that makes use of ultra-long sequence reads up to 2 Mb (megabases). In some embodiments the sequencing reaction is a long read-length sequencing reaction that makes use of full-length cDNA sequences.

In some embodiments, the sequencing is high throughput sequencing. In some embodiments, the sequencing is single cell 3' sequencing, single cell 5' sequencing, or single cell 5' paired-end sequencing. See, for example, Voet et al., 2013, "Single-cell paired-end genome sequencing reveals structural variation per cell cycle," Nucleic Acids Res 41: 6119-6138, Zong et al., 2012, "Genome-wide detection of single nucleotide and copy-number variations of a single human cell," Science 338, pp. 1622-1626; Navin et al., 2011, Tumour evolution inferred by single-cell sequencing," Nature 472, pp. 90-94, Snyder et al., 2012, "Clonal Evolution of Preleukemic Hematopoietic Stem Cells Precedes Human Acute Myeloid Leukemia," Science Translational Medicine 4, 149ra118, and Bourcy et al., 2014, "A Quantitative Comparison of Single-Cell Whole Genome Amplification Methods," PLOS ONE 9(8), e105585, each of which is hereby incorporated by reference.

In some embodiments, the captured sequence reads captured by the selectively capturing described above are amplified prior to the sequencing. In some embodiments, the sequencing comprises any of the aspects and/or embodiments described above (see, Definitions: Sequencing Analysis). Methods for sequencing enriched nucleic acid molecules that are contemplated in the present disclosure include, but are not limited to, any methods known in the art. Example methods for sequencing of enriched nucleic acid molecules are described in further detail in 10X Genomics, 2021, "Targeted Gene Expression—Single Cell User Guide", Document Number CG000293, Rev E, which is hereby incorporated herein by reference in its entirety.

In some embodiments, the analyzing the plurality of nucleic acid bait—sequence read complexes comprises processing the captured nucleic acid bait—sequence read complexes by preparing a gene expression library (e.g., a cDNA sequencing library).

For example, in some embodiments, enriched cDNA sequences are purified from the captured nucleic acid bait—sequence read complexes using any method known in the art. The enriched, purified cDNA sequences are then fragmented. In some embodiments, the fragmentation is performed by enzyme-based methods (e.g., by restriction enzymes, nicking enzymes and/or transposases), endonucleases, mechanical shearing (e.g., acoustic shearing, hydrodynamic shearing, and/or nebulization), and/or any combination or substitution thereof. In some embodiments, cDNA fragments are further processed via end-repair, poly-A tailing, or a combination thereof. In some embodiments, adaptors are ligated to each cDNA fragment. In some embodiments, the adaptors are ligated to the 3' end, the 5' end, or both ends of the fragment. In some embodiments, the adaptors are nucleic acid sequences that add a function, including but not limited to, spacer sequences, primer sequences/sites, barcode sequences, unique molecular identifier (UMI) sequences, linkers, and/or sequencing adaptors.

In some embodiments, the preparation of a gene expression library (e.g., a cDNA sequencing library) includes sample index (SI) PCR, which adds nucleic acid sequences (e.g., barcodes) to the 5' and/or 3' ends of the enriched, purified, and fragmented cDNA sequences. In some embodiments, the nucleic acid sequences added by SI—PCR are sample index sequences (e.g., i5 and i7). In some embodiments, the nucleic acid sequences added by SI—PCR comprise a P5 adapter and/or a P7 adapter.

In some embodiments, the preparation of a gene expression library (e.g., a cDNA sequencing library) includes amplification (e.g., PCR amplification) of the enriched, purified, and fragmented cDNA sequences. After amplification, the enriched, purified, and fragmented cDNA sequences are used to generate a gene expression library (e.g., a cDNA sequencing library) and sequenced using any method known in the art, including the exemplary sequencing methods described herein.

In some embodiments, a plurality of gene expression libraries (e.g., cDNA sequencing libraries) are prepared, where each library is obtained from a respective biological sample. In some such embodiments, each library in the plurality of libraries is individually sample-indexed, and the plurality of libraries is pooled to obtain a dual-indexed or multi-indexed library for downstream high-throughput sequencing.

In some embodiments, a respective gene expression library is a 3' gene expression single index library, a 3' gene expression dual index library, a 5' gene expression single index library, and/or a 5' gene expression dual index library.

Methods for preparing gene expression libraries that are contemplated in the present disclosure include, but are not limited to, any methods known in the art. Example methods for preparing gene expression libraries that are contemplated herein are described in further detail in 10X Genomics, 2021, "Targeted Gene Expression—Single Cell User Guide", Document Number CG000293, Rev E, which is hereby incorporated herein by reference in its entirety.

Referring to Block 254, in some embodiments, the analyzing the plurality of nucleic acid bait—sequence read complexes captured by the selectively capturing identifies one or more analytes (e.g., a gene and/or a gene product see, for instance, Definitions: "Nucleic Acid Analytes," above) in the biological sample. In some embodiments, the one or more analytes is a plurality of analytes. In some embodiments, the plurality of analytes is ten or more analytes. In some embodiments, the plurality of analytes is at least five, at least ten, at least twenty, at least thirty, at least forty, or at least fifty analytes. In some embodiments, the plurality of analytes comprises at least 3, at least 5, at least 10, at least 20, at least 30, at least 40, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 15,000, at least 20,000, or at least 30,000 analytes. In some embodiments, the plurality of analytes comprises no more than 100,000, no more than 50,000, no more than 10,000, no more than 5000, no more than 2000, no more than 1000, no more than 500, or no more than 100 analytes. In some embodiments, the plurality of analytes is from 5 to 30,000, from 50 to 10,000, from 200 to 5000, or from 500 to 2000 analytes. In some embodiments, the plurality of analytes falls within another range starting no lower than 3 analytes and ending no higher than 100,000 analytes.

Referring to Block 256, in some embodiments, an analyte in the one or more analytes comprises a mutation. Referring to Block 258, in some embodiments, an analyte in the one or more analytes comprises an alternative allele of a single nucleotide polymorphism (SNP). For example, in some embodiments, the analysis identifies one or more genetic variants including, but not limited to, single nucleotide polymorphisms (SNPs), splice variants, and/or gene fusions.

Referring to Block 260, in some embodiments, an analyte in the one or more analytes is associated with a disease or a condition of interest. For example, an analyte in the one or more analytes is associated, in some implementations, with a genetic disease or a cancer. Referring to Block 262, in some such embodiments, the method further comprises treating the subject for the disease or condition when it is determined from the one or more analytes that the subject has the disease or condition.

In some embodiments, the analyzing the plurality of nucleic acid bait—sequence read complexes captured by the selectively capturing comprises quantitation using quantitative PCT (qPCR).

In some embodiments, the analyzing the plurality of nucleic acid bait—sequence read complexes comprises applications of RNA ligation and/or targeted analyte analysis.

In some embodiments, the analyzing the plurality of nucleic acid bait—sequence read complexes comprises spatial sequencing. Example methods for spatial sequencing are disclosed in U.S. Provisional Application Ser. No. 62/938, 336, Titled "Pipeline for Spatial Analysis of Analytes," filed Dec. 9, 2019; and U.S. Provisional Patent Application No. 62/970,889, Titled "Capturing Targeted Genetic Targets Using A Hybridization/Capture Approach," filed Feb. 21, 2020, each of which is incorporated by reference in its entirety. Other Non-limiting aspects of spatial analysis methodologies are described in WO 2011/127099; WO 2014/210233; WO 2014/210225; WO 2016/162309; WO 2018/091676; WO 2012/140224; WO 2014/060483, U.S. Pat. Nos. 10,002,316, 9,727,810; U.S. Patent Application Publication No. 2017/0016053; Rodriques et al., Science 363(6434):1463-1467, 2019; WO 2018/045186, Lee et al., Nat. Protoc. 10(3):442-458, 2015; WO 2016/007839; WO 2018/045181; WO 2014/163886; Trejo et al., PLoS ONE 14(2):e0212031, 2019; U.S. Patent Application Publication No. 2018/0245142; Chen et al., Science 348(6233):aaa6090, 2015; Gao et al., BMC Biol. 15:50, 2017; WO 2017/144338; WO 2018/107054; WO 2017/222453; WO 2019/068880; WO 2011/094669; U.S. Pat. Nos. 7,709,198; 8,604,182; 8,951,726; 9,783,841; 10,041,949; WO 2016/057552; WO 2017/147483; WO 2018/022809; WO 2016/166128; WO 2017/027367; WO 2017/027368; WO 2018/136856; WO 2019/075091; U.S. Pat. No. 10,059,990; WO 2018/057999; WO 2015/161173; Gupta et al., Nature Biotechnol. 36:1197-1202, 2018; and U.S. Pat. No. 62,886,233, each of which is hereby incorporated by reference, or any combination thereof.

In some embodiments, the analyzing the plurality of nucleic acid bait—sequence read complexes comprises detection of one or more targeted analytes. In some such embodiments, the analyzing the plurality of nucleic acid bait—sequence read complexes comprises targeted spatial gene expression profiling by hybridization and capture of spatial cDNA.

Non-limiting example methods for spatial sequencing are provided in U.S. Provisional Patent Application No. 62/839, 346 entitled "Spatial Transcriptomics Of Biological Analytes In Tissue Samples," filed Apr. 26, 2019, and in U.S. Provisional Patent Application No. 62/979,889 entitled "Capturing Targeted Genetic Targets Using A Hybridization/ Capture Approach," filed Feb. 21, 2020, each of which is hereby incorporated herein by reference in its entirety.

II. Methods for Hybridization Capture Probe Design

Referring to Block 300, another aspect of the present disclosure provides a method 300 of identifying a plurality of nucleic acid baits (e.g., at least 500, 1000, 2000, 3000, 4000, or 5000 nucleic acid baits).

Obtaining Candidate Hybridization Sequences

Referring to Block 302, the method comprises, for each respective gene in a plurality of genes, obtaining a respective candidate hybridization sequence of the respective gene, where, when a length of the coding sequence of the respective gene satisfies a predetermined length threshold, the candidate hybridization sequence is the coding sequence of the respective gene, and when the length of the coding sequence of the respective gene does not satisfy a predetermined length threshold, the candidate hybridization sequence is an mRNA sequence of the respective gene.

Referring to Block 304, the method further comprises obtaining a corresponding plurality of transcripts for the respective gene.

In some embodiments, the plurality of genes is between five genes and twenty thousand genes. In some embodiments, the corresponding plurality of transcripts for the respective gene comprises three or more transcripts for the respective gene. In some embodiments, the corresponding plurality of transcripts for the respective gene comprises five or more transcripts for the respective gene. In some embodiments, the corresponding plurality of transcripts for the respective gene comprises a plurality of isoforms of the respective gene. In some embodiments, the plurality of isoforms of the respective gene comprises a first transcriptional isoform and a second transcriptional isoform of the respective gene. In some embodiments, the corresponding plurality of transcripts for the respective gene is each transcript of the respective gene annotated in GENCODE Release 33 (GRCh38.p 13).

In some embodiments, the plurality of genes and/or the plurality of transcripts for each respective gene in the plurality of genes comprises any of the aspects and/or embodiments described in the above sections (see, for example, Section I. Methods for Capturing Targeted Sequences using a Hybridization/Capture Approach).

Identifying Nucleic Acid Baits

Referring to Block 306, the method further comprises, for each respective sub-sequence of length K residues of the respective candidate hybridization sequence, determining a count of a number of transcripts in the corresponding plurality of transcripts the respective sub-sequence matches. Determining the count determines a corresponding first sub-sequence that matches a first maximal number of transcripts in the corresponding plurality of transcripts, where the transcripts in the corresponding plurality of transcripts that match the first sub-sequence define a corresponding first subset of transcripts, in a corresponding plurality of subsets of transcripts within the corresponding plurality of transcripts.

Referring to Block 314, the method further comprises, for each respective sub-sequence of length K residues of the respective candidate hybridization sequence, determining a count of a number of transcripts in the corresponding plurality of transcripts, other than those transcripts in the corresponding first subset of transcripts, the respective sub-sequence matches. Determining the count determines a corresponding second sub-sequence that matches a second maximal number of transcripts in the corresponding plurality of transcripts other than those transcripts in the corresponding first subset of transcripts, where the transcripts in the corresponding plurality of transcripts that match the second sub-sequence define a corresponding second subset of transcripts, in the corresponding plurality of subsets of transcripts within the corresponding plurality of transcripts.

Referring to Block 316, the method further comprises including a nucleic acid bait corresponding to the corresponding first sub-sequence in the plurality of nucleic acid baits; and including a nucleic acid bait corresponding to the corresponding second sub-sequence in the plurality of nucleic acid baits.

For example, each respective plurality of transcripts for each respective gene in the plurality of genes is grouped into two or more subsets of transcripts. In some embodiments, the first subset of transcripts comprises the maximal number of transcripts that can be hybridized to a single nucleic acid bait (e.g., that matches a corresponding first sub-sequence, of length K residues, of the respective candidate hybridization sequence of the respective gene). Thus, the first subset is defined as the largest number of transcripts that can be hybridized to a single sub-sequence of the candidate hybridization sequence. In some embodiments, the determination of the first subset of transcripts is performed by iterating each possible sub-sequence of length K residues (of the candidate hybridization sequence of the respective gene) across each transcript in the plurality of transcripts for the respective gene. The number of transcripts that match (e.g., comprise a complementary sequence to) each sub-sequence is tallied, and the first sub-sequence with the highest number of matches is selected as the first nucleic acid bait.

When the corresponding first subset of transcripts fails to account for all the transcripts in the corresponding plurality of transcripts for the respective gene, the process is repeated for all remaining transcripts that failed to match with the first sub-sequence. Thus, the determination of the second subset of transcripts is performed by iterating each possible sub-sequence of length K residues (of the candidate hybridization sequence of the respective gene) across each transcript in the plurality of transcripts, other than those transcripts in the first subset of transcripts, for the respective gene. The number of remaining transcripts that match (e.g., comprise a complementary sequence to) each sub-sequence is tallied, and the second sub-sequence with the highest number of matches is selected as the second nucleic acid bait.

The process is repeated as many times as desired, and/or until a plurality of nucleic acid baits are identified such that all transcripts in the plurality of transcripts for the respective gene is hybridizable to at least one nucleic acid bait in the plurality of nucleic acid baits.

For example, referring to Block 318, in some embodiments, when the corresponding first subset of transcripts and the corresponding second subset of transcripts fail to account for all the transcripts in the corresponding plurality of transcripts, the method further comprises, for each respective sub-sequence of length K residues of the respective candidate hybridization sequence, determining a count of a number of transcripts in the corresponding plurality of transcripts, other than those transcripts in the corresponding first or second subset of transcripts, the respective sub-sequence matches. The determining a count determines a corresponding third sub-sequence that matches a third maximal number of transcripts in the corresponding plurality of transcripts, other than those transcripts in the corresponding first and second subset of transcripts, where the transcripts in the corresponding plurality of transcripts that match the third sub-sequence define a corresponding third subset of transcripts, in the corresponding plurality of subsets of transcripts within the corresponding plurality of transcripts. The method further comprises including a nucleic acid bait corresponding to the corresponding third sub-sequence in the plurality of nucleic acid baits.

In some embodiments, the corresponding first subset of transcripts consists of two or more transcripts. In some embodiments, the corresponding first subset of transcripts consists of three or more transcripts. In some embodiments, the corresponding first subset of transcripts consists of four or more transcripts. In some embodiments, the first subset of transcripts consists of one or more, two or more, three or more, four or more, five or more, six or more, seven or more, eight or more, nine or more, or ten or more transcripts. In some embodiments, the corresponding second subset of transcripts consists of two or more transcripts. In some embodiments, the second subset of transcripts consists of one or more, two or more, three or more, four or more, five or more, six or more, seven or more, eight or more, nine or more, or ten or more transcripts. In some implementations, a respective subset of transcripts, e.g., in the plurality of subsets of transcripts, including the first and second subset of transcripts, for each respective gene in the plurality of genes comprises any of the aspects and/or embodiments described in the above sections (see, Section I. Methods for Capturing Targeted Sequences using a Hybridization/Capture Approach), and any substitutions, modifications, additions, deletions, and/or combinations thereof, as will be apparent to one skilled in the art.

In some embodiments, the third subset of transcripts consists of one or more, two or more, three or more, four or more, five or more, six or more, seven or more, eight or more, nine or more, or ten or more transcripts.

Referring to Block 308, in some embodiments, the determining a count of a number of transcripts in the corresponding plurality of transcripts the respective sub-sequence matches is performed using a native string-search algorithm using a computer system comprising a processor coupled to a non-transitory memory.

A string-search algorithm (e.g., a string-matching algorithm), performs a function in which one or more sub-strings are identified within a larger string. The function further identifies the position at which the sub-string is located within the larger string. A string includes but is not limited to a sequence of text (e.g., a sequence of nucleotide bases or an alphabet). String-matching is further described in Kurtz et al., 2004, "Versatile and open software for comparing large genomes," Genome Biol doi: 10.1186/gb-2004-5-2-r12, which is hereby incorporated herein by reference in its entirety.

Referring to Block 310, in some embodiments, the determining a count of a number of transcripts in the corresponding plurality of transcripts the respective sub-sequence matches is performed using a naïve string search, a finite-state-automaton-based search, a Rabin-Karp algorithm, a Knuth-Morris-Pratt algorithm, a Boyer-Moore string-search algorithm, a two-way string-matching algorithm, or a backward non-deterministic directed acyclic word graph matching algorithm using a computer system comprising a processor coupled to a non-transitory memory.

Referring to Block 312, in some embodiments, the determining a count of a number of transcripts in the corresponding plurality of transcripts the respective sub-sequence matches has a matching time of $Q*O(KM)$, wherein M is an average length of the corresponding plurality of transcripts, and Q is a number of transcripts in the corresponding plurality of transcripts, using a computer system comprising a processor coupled to a non-transitory memory.

As used herein, K refers to the length of the sub-sequence used in the string-searching algorithm. As used herein, O refers to asymptotic notation (e.g., Big-O notation). The matching time of the algorithm is bounded above and below by the function and is used, in some embodiments, to analyze the average case complexity of the algorithm. The matching time for a single sub-sequence in a single transcript is equal to $O(KM)$ (e.g., for a naïve string-search algorithm). Methods of analyzing the computational complexity of algorithms are known in the art, including cost models (e.g., uniform and/or logarithmic) and run-time analysis (e.g., orders of growth), and are implemented by any embodiments, substitutions, and/or combinations thereof as will be apparent to one skilled in the art.

Advantageously, the present disclosure provides systems and methods that improve the computational elucidation of optimized sub-sequences using a string-searching algorithm in the corresponding plurality of transcripts. The complexity of an algorithm includes time complexity (running time, or the measure of the speed of an algorithm for a given input size n), space complexity (space requirements, or the amount of computing power or memory needed to execute an algorithm for a given input size n), or both. Complexity (and subsequent computational burden) applies to both training of and output (e.g., prediction) by a given algorithm.

In some instances, computational complexity is impacted by implementation, incorporation of additional algorithms or cross-validation methods, and/or one or more parameters (e.g., weights and/or hyperparameters). In some instances, computational complexity is expressed as a function of input size n, where input data is the number of instances (e.g., the number of genes in the plurality of genes), dimensions p (e.g., the number of transcripts and/or nucleic acid baits), the number of trees $n_{trees}$ (e.g., for methods based on trees), the number of support vectors $n_{sv}$ (e.g., for methods based on support vectors), the number of neighbors k (e.g., for k nearest neighbor algorithms), the number of classes c, and/or the number of neurons $n_i$ at a layer i (e.g., for neural networks). With respect to input size n, then, an approximation of computational complexity (e.g., in Big O notation) denotes how running time and/or space requirements increase as input size increases. Functions can increase in complexity at slower or faster rates relative to an increase in input size. Various approximations of computational complexity include but are not limited to constant (e.g., $O(1)$), logarithmic (e.g., $O(\log n)$), linear (e.g., $O(n)$), loglinear (e.g., $O(n \log n)$), quadratic (e.g., $O(n^2)$), polynomial (e.g., $O(n^c)$), exponential (e.g., $O(c^n)$), and/or factorial (e.g., $O(n!)$). In some instances, simpler functions are accompanied by lower levels of computational complexity as input sizes increase, as in the case of constant functions, whereas more complex functions such as factorial functions can exhibit substantial increases in complexity in response to slight increases in input size.

As described above, for algorithms, computational complexity indicates the scalability and thus the overall effectiveness and usability of a model (e.g., an algorithm) for increasing input, feature, and/or class sizes, as well as for variations in the architecture and implementation of the algorithm. In the context of large-scale sequencing technologies, the computational complexity of functions performed on sequencing datasets (e.g., nucleic acid sequencing data) may strain the capabilities of many existing systems. In addition, as the number or size of input features (e.g., number and length of cDNA sequences, transcripts, subsets of transcripts, nucleic acid baits, sub-sequences, and/or any statistics thereof (e.g., mean, min, max, median, standard deviation)) and/or the number of instances (e.g., biological samples and/or genes) increases with expanding downstream applications and possibilities, the computational complexity of any given algorithm, such as a string-search algorithm, can quickly overwhelm the time and space capacities provided by the specifications of a respective system.

Thus, by using an algorithm with a minimum number of features (e.g., at least $2 \times 10^3$ nucleic acid baits) and/or a minimum feature size (e.g., a sub-sequence of length K residues) for the identification of nucleic acid baits for a respective gene in a plurality of genes, the computational complexity is proportionally increased such that it cannot be mentally performed, and the method further encompasses a computational problem.

Additional details on computational complexity in machine learning models are provided in "Computational complexity of machine learning algorithms," published Apr. 16, 2018, available online at: thekerneltrip.com/machine/learning/computational-complexity-learning-algorithms; Hastie, 2001, *The Elements of Statistical Learning*, Springer, New York; and Arora and Barak, 2009, *Computational Complexity: A Modern Approach*, Cambridge University Press, New York; each of which is hereby incorporated herein by reference in its entirety.

In some alternative embodiments, determining the count determines a corresponding first sub-sequence that matches a first minimal number of transcripts in the corresponding plurality of transcripts, where the transcripts in the corresponding plurality of transcripts that match the first sub-sequence define a corresponding first subset of transcripts within the corresponding plurality of transcripts. For example, in some instances it is desirable to select nucleic acid baits that enrich for rare transcripts and/or rare genes. Thus, sub-sequences that match a minimal number of transcripts are likely to have high specificity for unique transcripts and/or genes.

In some embodiments, K is between 25 and 1000, between 50 and 500, between 90 and 150, or between 95 and 130. In some embodiments, K is 100 or 120.

In some embodiments, the plurality of nucleic acid baits, and the methods of obtaining and using the same, comprises any of the aspects and/or embodiments described in the above sections (see, Section I. Methods for Capturing Targeted Sequences using a Hybridization/Capture Approach), and any substitutions, modifications, additions, deletions, and/or combinations thereof, as will be apparent to one skilled in the art.

For example, in some embodiments, the plurality of nucleic acid baits includes a minimum number of nucleic acid baits necessary to selectively hybridize to each respective transcript in the corresponding plurality of transcripts for a respective gene in the plurality of genes. In some embodiments, the plurality of nucleic acid baits consists of a minimum number of nucleic acid baits necessary to selectively hybridize to each respective transcript in the corresponding plurality of transcripts for each respective gene in the plurality of genes.

In some embodiments, each respective nucleic acid bait in the plurality of nucleic acid baits shares less than a threshold percentage of sequence identity to any other nucleic acid bait in the plurality of nucleic acid baits. In some embodiments, the threshold percentage of sequence identity is ten percent, twenty percent, thirty percent, or between five and fifty percent. In some embodiments, each respective nucleic acid bait in the plurality of nucleic acid baits comprises a nucleic acid sequence that has a minimal identity to the reference genome of at least 90%.

In some embodiments, the plurality of nucleic acid baits comprises at least $2 \times 10^3$, at least $3 \times 10^3$, at least $4 \times 10^3$, at least $5 \times 10^3$, at least $1 \times 10^4$, at least $2 \times 10^4$, at least $3 \times 10^4$, at least $4 \times 10^4$, at least $5 \times 10^4$, at least $6 \times 10^4$, at least $7 \times 10^4$, or at least $1 \times 10^5$ nucleic acid baits.

In some embodiments, the method further comprises subjecting each sub-sequence of length K residues of the candidate hybridization sequence to one or more selection criteria. In some such embodiments, the method comprises removing (e.g., filtering) each sub-sequence that fails to satisfy the one or more selection criteria from the plurality of sub-sequences. In some embodiments, the one or more selection criteria comprise any of the selection criteria and/or parameters of nucleic acid baits described in the above sections (see, Section I. Methods for Capturing Targeted Sequences using a Hybridization/Capture Approach). In some embodiments, non-limiting examples of the one or more selection criteria include minimum threshold sequence identity, maximum threshold number of representations in a reference genome, minimum threshold distance from any highly represented portions of a reference genome, minimum threshold distance from any annotated start and/or stop sites, minimum threshold distance from the 3' end (e.g., including any 3' annotations), minimum threshold distance from the 5' end (e.g., including any 5' annotations), presence of unannotated poly-A sites and/or sequences, threshold Tm ranges, and/or coverage requirements.

For example, in some embodiments, the method further comprises filtering the plurality of nucleic acid baits for mappability, absence of repetitive subsequences, and/or overall GC content.

In some embodiments, each respective substring of fixed length P nucleotides in each respective nucleic acid bait in the plurality of nucleic acid baits is represented in the reference genome less than a threshold number of times L. In some embodiments, P is at least 15 nucleotides, at least 25 nucleotides, or more. In some embodiments, L is between 2 and 50.

In some embodiments, the method further comprises modifying a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L. The modifying comprises (i) removing the respective nucleic acid bait from the plurality of nucleic acid baits, (ii) truncating the respective nucleic acid bait such that the respective nucleic acid bait is represented in the reference genome at a position that is at least M base pairs away from any portion of the reference genome that comprises the substring of fixed length P, or (iii) shifting the respective sequence of the nucleic acid bait along the reference genome such that the respective sequence of the nucleic acid bait is represented in the reference genome at a position that is at least M base pairs away from any portion of the reference genome that comprises the substring of fixed length P. In some embodiments, P is between 10 and 75, between 20 and 50, or between 37 and 43. In some embodiments, L is between 2 and 1000, between 5 and 500, between 10 and 100, between 20 and 50, or between 23 and 27.

In some embodiments, values for K, P, L, M and/or any other parameters for nucleic acid bait design are provided by a user or practitioner. In some embodiments, values for K, P, L, M, and/or any other parameters for nucleic acid bait design, and any methods of obtaining or using the same, include any of the aspects and/or embodiments described in the above sections (see, Section I. Methods for Capturing Targeted Sequences using a Hybridization/Capture Approach), and any substitutions, modifications, additions, deletions, and/or combinations thereof, as will be apparent to one skilled in the art.

In some embodiments, each nucleic acid bait in the plurality of nucleic acid baits is a minimum threshold distance along a reference genome from any other nucleic acid bait. In some embodiments, each respective nucleic acid bait in the plurality of nucleic acid baits that hybridizes to an transcript in the plurality of transcripts of the respective gene (i) selectively hybridizes to a portion of a first transcript in the plurality of transcripts, or (ii) selectively hybridizes to a portion of an transcript in the plurality of transcripts, other than the first transcript, and is represented by a corresponding portion of a directed graph that is at least a threshold number of edges away (e.g., 1 edge, 2 edges, 3 edges, 4 edges) from any portion of the directed graph that represents a nucleic acid bait that selectively hybridizes to a portion of the first transcript of the respective gene. In some embodiments, the directed graph is a DeBruijn graph.

In some embodiments, one or more nucleic acid baits in the plurality of nucleic acid baits is less than a minimum threshold distance along a reference genome from any other nucleic acid bait. In some embodiments, one or more first nucleic acid baits in the plurality of nucleic acid baits overlaps along a reference genome with one or more second nucleic acid baits in the plurality of nucleic acid baits.

In some embodiments, for each respective gene in the plurality of genes, each respective nucleic acid bait in the plurality of nucleic acid baits hybridizes to a region of the respective gene that is at least a minimum threshold distance away from any annotated start site of the respective gene. In some embodiments, for each respective gene in the plurality of genes, each respective nucleic acid bait in the plurality of nucleic acid baits hybridizes to a region of the respective gene that is at least a minimum threshold distance away from any annotated stop site of the respective gene. In some embodiments, for each respective gene in the plurality of genes, each respective nucleic acid bait in the plurality of nucleic acid baits hybridizes to a region of the respective gene that is at least a minimum threshold distance away from a 3' end of any cDNA sequence mapping to the respective gene. In some embodiments, for each respective gene in the plurality of genes, each respective nucleic acid bait in the plurality of nucleic acid baits hybridizes to a region of the respective gene that is at least a minimum threshold distance away from a 5' end of any cDNA sequence mapping to the respective gene.

Non-limiting examples of a minimum threshold distance (e.g., from any annotated start and/or stop sites, any 3' end, and/or any 5' end of a respective sequence read) are from 100 to 200 base pairs (bp), from 200 to 300 bp, from 300 to 400 bp, from 400 to 500 bp, from 500 to 600 bp, from 600 to 700 bp, from 700 to 800 bp, from 800 to 900 bp, from 900 to 1000 bp, or more than 1000 bp. In some embodiments, the minimum threshold distance is at least 20, at least 30, at least 40, at least 50, at least 100, at least 200, at least 300, at least 400, at least 500, at least 600, at least 700, at least 800, at least 900, or at least 1000 bp. In some embodiments, the minimum threshold distance is no more than 2000, no more than 1000, no more than 800, no more than 500, no more than 300, no more than 200, or no more than 100 bp. In some embodiments, the minimum threshold distance is from 20 to 2000 bp, from 100 to 1000 bp, or from 200 to 800 bp. In some embodiments, the minimum threshold distance falls within another range starting no lower than 20 bp and ending no higher than 2000 bp.

Non-limiting examples of a minimum threshold distance (e.g., from any annotated start and/or stop sites, any 3' end, and/or any 5' end of a respective sequence read) are from 100 to 200 base pairs (bp), from 200 to 300 bp, from 300 to 400 bp, from 400 to 500 bp, from 500 to 600 bp, from 600 to 700 bp, from 700 to 800 bp, from 800 to 900 bp, from 900 to 1000 bp, or more than 1000 bp. In some embodiments, the minimum threshold distance is at least 20, at least 30, at least 40, at least 50, at least 100, at least 200, at least 300, at least 400, at least 500, at least 600, at least 700, at least 800, at least 900, or at least 1000 bp. In some embodiments, the minimum threshold distance is no more than 2000, no more than 1000, no more than 800, no more than 500, no more than 300, no more than 200, or no more than 100 bp. In some embodiments, the minimum threshold distance is from 20 to 2000 bp, from 100 to 1000 bp, or from 200 to 800 bp. In some embodiments, the minimum threshold distance falls within another range starting no lower than 20 bp and ending no higher than 2000 bp.

Using Nucleic Acid Baits for Hybridization Capture

Referring to Blocks 320-326, the method further comprises obtaining a plurality of cDNA sequences from a pool of poly-adenylated mRNA obtained from a biological sample of a subject, where the plurality of cDNA sequences comprise a first subset of cDNA sequences and a second subset of cDNA sequences, each respective cDNA sequence in the first subset of cDNA sequences maps to a respective gene in a plurality of genes, and each respective cDNA sequence in the second subset of cDNA sequences maps to a portion of a reference genome not represented by the plurality of genes (320). The plurality of cDNA sequences is exposed to the plurality of nucleic acid baits, thus forming a plurality of nucleic acid bait—sequence read complexes (322). The plurality of nucleic acid bait—sequence read complexes are selectively captured (324). The plurality of nucleic acid bait—sequence read complexes captured by the selectively capturing are analyzed (326).

In some embodiments, the subjects, biological samples, cDNA sequences, and methods of obtaining, processing, and capturing the same, comprise any of the aspects and/or embodiments described in the above sections (see, Section I. Methods for Capturing Targeted Sequences using a Hybridization/Capture Approach). For example, in some embodiments, the pool of poly-adenylated mRNA is obtained from the biological sample by single cell 3' sequencing, single cell 5' sequencing, or single cell 5' paired-end sequencing. In some embodiments, the plurality of cDNA sequences is at least $1\times10^6$ cDNA sequences. In some embodiments, the plurality of cDNA sequences is at least $1\times10^7$ cDNA sequences. In some embodiments, the plurality of cDNA sequences consists of the first subset of cDNA sequences and the second subset of cDNA sequences.

In some embodiments, the selectively capturing the plurality of nucleic acid bait-sequence read complexes captures the plurality of nucleic acid bait—sequence read complexes to a solid support. In some embodiments, the solid support comprises a bead. In some embodiments, each nucleic acid bait in the plurality of nucleic acid baits comprises a non-nucleotide binding moiety, the solid support comprises a plurality of capture moieties, and a respective nucleic acid bait—sequence read complex is captured on the solid support through a reaction between a capture moiety in the plurality of capture moieties and the corresponding binding moiety of the respective nucleic acid bait—sequence read complex. In some embodiments, a capture moiety in the plurality of capture moieties comprises streptavidin and the corresponding non-nucleotide binding moiety comprises biotin, 2-(4-Hydroxyphenylazo)benzoic acid (HABA), or a compound listed in Table 1.

Referring to Block 328, in some embodiments, the analyzing the plurality of nucleic acid bait—sequence read complexes captured by the selectively capturing comprises sequencing of nucleic acid bait—sequence read complexes captured. In some embodiments, the analyzing the plurality of nucleic acid bait—sequence read complexes captured by the selectively capturing identifies one or more analytes in the biological sample. In some embodiments, the one or more analytes is a plurality of analytes. In some embodiments, the plurality of analytes is ten or more analytes. In some embodiments, an analyte in the one or more analytes comprises a mutation. In some embodiments, an analyte in the one or more analytes comprises an alternative allele of a single nucleotide polymorphism (SNP). In some embodiments, an analyte in the one or more analytes is associated with a disease or a condition. In some such embodiments, the method further comprises treating the subject for the disease or condition when it is determined from the one or more analytes that the subject has the disease or condition.

In some embodiments, the analysis and applications using the plurality of nucleic acid bait—sequence read complexes captured by the selectively capturing comprise any of the aspects and/or embodiments described in the above sections (see, Section I. Methods for Capturing Targeted Sequences using a Hybridization/Capture Approach).

III. Other Aspects of the Disclosure

Another aspect of the present disclosure provides a kit comprising a plurality of nucleic acid baits (e.g., at least 50, at least 100, at least 500, at least $1\times10^3$, or at least $2\times10^3$ nucleic acid baits) each of length that is between $K_1$ and $K_2$ residues. Each respective nucleic acid bait in the plurality of nucleic acid baits that hybridizes to a cDNA sequence, in a plurality of cDNA sequences, mapping to a respective gene in a plurality of genes (i) selectively hybridizes to a first subset of transcripts, in a corresponding plurality of subsets of transcripts in a plurality of transcripts corresponding to the respective gene, or (ii) selectively hybridizes to another subset of transcripts, other than the first subset of transcripts, in the corresponding plurality of subsets of transcripts in the plurality of transcripts corresponding to the respective gene.

The plurality of cDNA sequences is obtained from a pool of poly-adenylated mRNA obtained from a biological sample of a subject, where the plurality of cDNA sequences comprises a first subset of cDNA sequences and a second subset of cDNA sequences, each respective cDNA sequence in the first subset of cDNA sequences maps to a respective gene in a plurality of genes, and each respective cDNA sequence in the second subset of cDNA sequences maps to a portion of a reference genome not represented by the plurality of genes. Each respective transcript in the corresponding plurality of transcripts of each respective gene in the plurality of genes is hybridizable to a nucleic acid bait in the plurality of nucleic acid baits.

In some embodiments, the kit comprises at least 10, at least 50, at least 100, at least 200, at least 300, at least 400, at least 500, at least 1000, at least 2000, at least 3000, at least 4000, at least 5000, at least 10,000, at least 20,000, at least 30,000, at least 40,000, at least 50,000, or at least 100,000 nucleic acid baits. In some embodiments, the kit comprises no more than 200,000, no more than 100,000, no more than 50,000, no more than 20,000, no more than 10,000, no more than 5000, no more than 4000, no more than 3000, no more than 2000, no more than 1000, no more than 500, or no more than 100 nucleic acid baits. In some embodiments, the kit comprises from 10 to 500, from 100 to 10,000, from 1000 to 6000, from 2000 to 5000, from 3000 to 4000, from 5000 to 20,000, from 20,000 to 50,000, or from 10,000 to 60,000 nucleic acid baits. In some embodiments, the kit includes a plurality of nucleic acid baits that falls within another range starting no lower than 10 nucleic acid baits and ending no higher than 200,000 nucleic acid baits.

In some embodiments, any of the methods and/or embodiments for nucleic acid baits, design and use of nucleic acid baits, genes, cDNA sequences, transcripts, isoforms, biological samples, methods for hybridization and capture, and/or analysis and applications described in the above sections (see, Section I. Methods for Capturing Targeted Sequences using a Hybridization/Capture Approach and Section II. Methods for Hybridization/Capture Probe Design) are contemplated for use with respect to the presently described kit, and any substitutions, modifications, and/or combinations thereof, as will be apparent to one skilled in the art.

For example, in some embodiments, each nucleic acid bait in the plurality of nucleic acid baits comprises a corresponding non-nucleotide binding moiety. In some embodiments, the corresponding non-nucleotide binding moiety comprises biotin, 2-(4-Hydroxyphenylazo)benzoic acid (HABA), or a compound listed in Table 1.

In some embodiments, each respective nucleic acid bait in the plurality of nucleic acid baits shares less than a threshold percentage of sequence identity to any other nucleic acid bait in the plurality of nucleic acid baits. In some embodiments, the threshold percentage of sequence identity is ten percent, twenty percent, thirty percent, or between five and fifty percent.

In some embodiments, the plurality of nucleic acid baits is filtered for mappability, absence of repetitive subsequences, and/or overall GC content.

In some embodiments, the plurality of genes is between five genes and twenty thousand genes. In some embodiments, the plurality of transcripts corresponding to the respective gene comprises three or more transcripts for the respective gene. In some embodiments, the plurality of transcripts corresponding to the respective gene comprises five or more transcripts for the respective gene. In some embodiments, the first subset of transcripts consists of two or more transcripts. In some embodiments, the first subset of transcripts consists of three or more transcripts. In some embodiments, the first subset of transcripts consists of four or more transcripts. In some embodiments, the another subset of transcripts, other than the first subset of transcripts, consists of two or more transcripts.

In some embodiments, the plurality of nucleic acid baits includes a minimum number of baits necessary to selectively hybridize to each respective transcript in the corresponding plurality of transcripts for a respective gene in the plurality of genes.

In some embodiments, the plurality of nucleic acid baits consists of a minimum number of baits necessary to selectively hybridize to each respective transcript in the corresponding plurality of transcripts for each respective gene in the plurality of genes.

In some embodiments, $K_1$ is 25 and $K_2$ is 1000. In some embodiments, $K_1$ is 50 and $K_2$ is 500. In some embodiments, $K_1$ is 90 and $K_2$ is 150. In some embodiments, $K_1$ is 95 and $K_2$ is 130. In some embodiments, $K_1$ is the same value of $K_2$. In some embodiments, $K_1$ is 100 or 120. In some embodiments, $K_1$ and $K_2$ are different positive integers.

In some embodiments, each respective substring of fixed length P nucleotides in each respective nucleic acid bait in the plurality of nucleic acid baits is represented in the reference genome less than a threshold number of times L. In some embodiments, P is at least 15 nucleotides. In some embodiments, P is at least 25 nucleotides. In some embodiments, L is between 2 and 50.

In some embodiments, each respective nucleic acid bait in the plurality of nucleic acid baits comprises a nucleic acid sequence that has a minimal identity to the reference genome of at least 90%.

In some embodiments, the method further comprises designing a nucleic acid bait in the plurality of nucleic acid baits for a respective gene in the plurality of genes using, when the length of the coding sequence of the respective gene satisfies a predetermined length threshold, the coding sequence of the respective gene, and when the length of the coding sequence of the respective gene does not satisfy a predetermined length threshold, an mRNA sequence of the respective gene.

In some embodiments, the method further comprises modifying a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L, where the modifying comprises (i) removing the respective nucleic acid bait from the plurality of nucleic acid baits, (ii) truncating the respective nucleic acid bait such that the respective nucleic acid bait is represented in the reference genome at a position that is at least M base pairs away from any portion of the reference genome that comprises the substring of fixed length P, or (iii) shifting the respective sequence of the nucleic acid bait along the reference genome such that the respective sequence of the nucleic acid bait is represented in the reference genome at a position that is at least M base pairs away from any portion of the reference genome that comprises the substring of fixed length P. In some embodiments, P is between 10 and 75, between 20 and 50, or between 37 and 43. In some embodiments, L is between 2 and 1000, between 5 and 500, between 10 and 100, between 20 and 50, or between 23 and 27.

In some embodiments, for each respective gene in the plurality of genes, each respective nucleic acid bait in the plurality of nucleic acid baits hybridizes to a region of the respective gene that is at least a minimum threshold distance away from any annotated start site and/or any annotated stop site of the respective gene. In some embodiments, for each respective gene in the plurality of genes, each respective nucleic acid bait in the plurality of nucleic acid baits hybridizes to a region of the respective gene that is at least a minimum threshold distance away from a 3' end and/or any 5' end of any cDNA sequence mapping to the respective gene. In some embodiments, the minimum threshold distance is from 20 to 2000 base pairs, from 100 to 1000 base pairs, or from 200 to 800 base pairs.

In some embodiments, for a respective gene in the plurality of genes, the plurality of nucleic acid baits includes a set of nucleic acid baits that is fully tiled across the respective gene. In other words, in some such embodiments, the set of nucleic acid baits for the respective gene exhaustively represents the cDNA sequences of the respective gene (e.g., as a series of k-mers, where each bait is a different k-mer as explained above). For instance, in some embodiments, the set of nucleic acid baits that is fully tiled across the respective gene is obtained by a method comprising obtaining a respective candidate hybridization sequence of the respective gene, where, when a length of the coding sequence of the respective gene satisfies a predetermined length threshold, the candidate hybridization sequence is the coding sequence of the respective gene, and when the length of the coding sequence of the respective gene does not satisfy a predetermined length threshold, the candidate hybridization sequence is an mRNA sequence of the respective gene. In some embodiments, the method further comprises, for each respective sub-sequence of length K residues of the respective candidate hybridization sequence, including a nucleic acid bait corresponding to the respective sub-sequence of length K residues in the plurality of nucleic acid baits. Thus, in some such embodiments, the method for obtaining a set of nucleic acid baits that is fully tiled across the respective gene comprises obtaining a plurality of sub-sequences of length K residues, where the plurality of sub-sequences of length K residues (e.g., k-mers) represents every possible k-mer across a coding sequence and/or an mRNA sequence of the respective gene. In some embodiments, the plurality of sub-sequences of length K residues (e.g., k-mers) represents, for each respective allele in a plurality of alleles of the respective gene, a nucleic acid sequence corresponding to the respective allele. For instance, in some embodiments, the plurality of sub-sequences of length K residues (e.g., k-mers) represents, for each respective allele in a plurality of alleles of the respective gene, every possible k-mer across the nucleic acid sequence corresponding to the respective allele. In some embodiments, the plurality of sub-sequences of length K residues (e.g., k-mers) represents, for each respective allele in a plurality of alleles represented by a plurality of transcripts for the respective gene, a nucleic acid sequence corresponding to the respective allele. For instance, in some embodiments, the plurality of sub-sequences of length K residues (e.g., k-mers) represents, for each respective allele in a plurality of alleles for the respective gene, every possible k-mer across each respective transcript in the plurality of transcripts that corresponds to the respective allele. In some embodiments, there are one or more, two or more, three or more, five or more, six or more, seven or more, eight or more, nine or more, or 10 or more alleles in the plurality of alleles for the respective gene.

In some embodiments, the respective gene has a corresponding fully-tiled set of nucleic acid baits, where each possible k-mer of length K, for each transcript in the plurality of transcripts that characterizes the respective gene, is represented by a respective nucleic acid bait in the plurality of nucleic acid baits. In some embodiments, the respective gene has a corresponding fully-tiled set of nucleic acid baits, where each possible k-mer of length K, for a respective nucleic acid sequence corresponding to the respective gene (e.g., a coding sequence, an mRNA sequence, and/or a genomic sequence), is represented by a respective nucleic acid bait in the plurality of nucleic acid baits. In some embodiments, the respective gene has a corresponding fully-tiled set of nucleic acid baits, where each possible k-mer of length K, for each cDNA sequence, in the plurality of cDNA sequences, mapping to the respective gene, is represented by a respective nucleic acid bait in the plurality of nucleic acid baits.

In some embodiments, for a respective gene in the plurality of genes, the plurality of nucleic acid baits includes a set of nucleic acid baits that is minimally tiled across the respective gene (e.g., the minimum number of baits necessary to selectively hybridize to each respective transcript in the corresponding plurality of transcripts for the respective gene). In some embodiments, the minimally-tiled set of nucleic acid baits is obtained through a method for hybridization/capture probe design, as described herein and in accordance with some embodiments of the present disclosure (see, for example, Section II. Methods for Hybridization/Capture Probe Design).

In some embodiments, for a respective gene in the plurality of genes, the plurality of nucleic acid baits includes a set of nucleic acid baits that is partially tiled (e.g., fewer nucleic acid baits than a fully-tiled bait set but more nucleic acid baits than a minimally-tiled bait set) across the respective gene. In some embodiments, the partially-tiled set of nucleic acid baits is obtained through a method for hybridization/capture probe design, as described herein and in accordance with some embodiments of the present disclosure (see, for example, Section II. Methods for Hybridization/Capture Probe Design), where at least 1 additional nucleic acid bait is further included in the identified plurality of nucleic acid baits. For instance, in some embodiments, the partially-tiled set of nucleic acid baits is obtained by a method comprising identifying the minimum number of baits necessary to selectively hybridize to each respective transcript in the corresponding plurality of transcripts for the respective gene, and further adding, to the identified plurality of nucleic acid baits, at least 1 additional nucleic acid bait that selectively hybridizes to at least 1 transcript in the corresponding plurality of transcripts for the respective gene.

In some embodiments, for a respective gene in the plurality of genes, the plurality of nucleic acid baits includes a set of nucleic acid baits that is obtained using any other method for identifying and/or obtaining nucleic acid baits for a respective gene known in the art, or any substitutions, modifications, additions, deletions, and/or combinations thereof, as will be apparent to one skilled in the art.

As described above, in some embodiments, a first gene in the plurality of genes has a bait coverage (e.g., a number and/or ratio of nucleic acid baits, in the plurality of nucleic acid baits, that hybridizes to a respective gene and/or to each transcript in the plurality of transcripts that characterizes a respective gene) that is the same or different from a second gene in the plurality of genes. In some embodiments, each gene in a first subset of genes in the plurality of genes has a bait coverage (e.g., a set of nucleic acid baits, in the plurality of nucleic acid baits, that hybridizes to each transcript in the plurality of transcripts that characterizes the respective gene) that is the same or different from each gene in a second subset of genes in the plurality of genes.

For instance, in some embodiments, each gene in a first subset of genes, in the plurality of genes, is selectively hybridized to by a respective minimally-tiled nucleic acid bait set for the respective gene. In some embodiments, the respective minimally-tiled bait set for the respective gene is obtained using any of the methods disclosed herein, or any substitutions, modifications, additions, deletions, and/or combinations thereof, as will be apparent to one skilled in the art. In some embodiments, each gene in a second subset of genes, in the plurality of genes, is selectively hybridized to by a respective fully-tiled nucleic acid bait set for the respective gene. In some embodiments, the respective fully-tiled bait set for the respective gene is obtained using any of the methods described above.

Alternatively or additionally, in some embodiments, each gene in a subsequent subset of genes in the plurality of genes, other than the first subset of genes, is selectively hybridized to by a respective partially-tiled (e.g., less than fully-tiled but more than minimally-tiled) nucleic acid bait set for the respective gene. In some embodiments, the respective partially-tiled bait set for the respective gene is obtained using any of the methods described above. Alternatively or additionally, in some embodiments, each gene in a subsequent subset of genes in the plurality of genes, other than the first subset of genes, is selectively hybridized to by a respective nucleic acid bait set for the respective gene obtained using any other method of obtaining nucleic acid baits for a respective gene known in the art, as described above.

In some embodiments, the first subset of genes comprises at least 3, at least 5, at least 10, at least 20, at least 30, at least 40, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 15,000, at least 20,000, or at least 30,000 genes. In some embodiments, the first subset of genes comprises no more than 100,000, no more than 50,000, no more than 10,000, no more than 5000, no more than 2000, no more than 1000, no more than 500, or no more than 100 genes. In some embodiments, the first subset of genes is from 5 to 30,000, from 50 to 10,000, from 200 to 5000, or from 500 to 2000 genes. In some embodiments, the first subset of genes falls within another range starting no lower than 3 genes and ending no higher than 100,000 genes.

In some embodiments, the first subset of genes comprises a percentage X of the plurality of genes. In some embodiments, X is at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, or at least 95%. In some embodiments, X is no more than 99, no more than 98, no more than 95, no more than 90, no more than 80, no more than 70, no more than 60, no more than 50, no more than 40, no more than 30, or no more than 20%. In some embodiments, X is from 20 to 90, from 50 to 100, from 10 to 60, or from 15 to 99%. In some embodiments, X falls within another range starting no lower than 5% and ending no higher than 100%.

In some embodiments, the second subset of genes and/or any subsequent subset of genes in the plurality of genes, other than the first subset of genes, comprises a percentage that is 1−X of the genes in the plurality of genes. For instance, in some embodiments, each respective gene in a subset of X genes in the plurality of genes is selectively hybridized to by a respective minimally-tiled nucleic acid bait set for the respective gene. In some embodiments, each respective gene in the subset of X genes in the plurality of genes is selectively hybridized to by a respective fully-tiled nucleic acid bait set for the respective gene. In some embodiments, each respective gene in a subset of X genes in the plurality of genes is selectively hybridized to by a respective partially-tiled nucleic acid bait set for the respective gene. In some embodiments, the subset of X genes in the plurality of genes includes a combination of genes selectively hybridized to by respective minimally-tiled nucleic acid bait sets, genes selectively hybridized to by respective fully-tiled nucleic acid bait sets, and genes selectively hybridized to by respective partially-tiled nucleic acid bait sets. In some embodiments, each gene in a subset 1−X genes (where the quantities X and 1−X sum to 100 percent of the plurality of genes), in the plurality of genes, is selectively hybridized to by a respective minimally-tiled nucleic acid bait set for the respective gene. In some embodiments, each respective gene in the subset of 1−X genes in the plurality of genes is selectively hybridized to by a respective fully-tiled nucleic acid bait set for the respective gene. In some embodiments, each respective gene in a subset of 1−X genes in the plurality of genes is selectively hybridized to by a respective partially-tiled nucleic acid bait set for the respective gene. In some embodiments, the subset of 1−X genes in the plurality of genes includes a combination of genes selectively hybridized to by respective minimally-tiled nucleic acid bait sets, genes selectively hybridized to by respective fully-tiled nucleic acid bait sets, and genes selectively hybridized to by respective partially-tiled nucleic acid bait sets. In some embodiments, each respective gene in the subset of X genes in the plurality of genes is selectively hybridized to by a respective minimally-tiled nucleic acid bait set for the respective gene, and each respective gene in the subset of 1−X genes in the plurality of genes is selectively hybridized to by a respective fully-tiled nucleic acid bait set for the respective gene. In some embodiments, each respective gene in the subset of X genes in the plurality of genes is selectively hybridized to by a respective minimally-tiled nucleic acid bait set for the respective gene, and each respective gene in the subset of 1−X genes in the plurality of genes is selectively hybridized to by a respective partially-tiled nucleic acid bait set for the respective gene. In some embodiments, each respective gene in the subset of X genes in the plurality of genes is selectively hybridized to by a respective minimally-tiled nucleic acid bait set for the respective gene, and the subset of 1−X genes in the plurality of genes includes a combination of genes selectively hybridized to by respective fully-tiled nucleic acid bait sets and genes selectively hybridized to by respective partially-tiled nucleic acid bait sets.

Thus, in some embodiments, the kit comprises a plurality of nucleic acid baits that is a mixed or hybrid nucleic acid bait set, where the mixed or hybrid bait set includes one or more of exhaustively represented, partially tiled, and/or minimally tiled nucleic acid baits for a corresponding one or more genes in the plurality of genes.

Another aspect of the present disclosure provides a plurality of conjugated nucleic acid baits, the plurality of conjugated nucleic acid baits comprising at least $2 \times 10^3$ nucleic acid baits each of length that is between $K_1$ and $K_2$ residues and conjugated to a non-nucleotide binding moiety. Each respective conjugated nucleic acid bait in the plurality of conjugated nucleic acid baits that hybridizes to a cDNA sequence, in a plurality of cDNA sequences, mapping to a respective gene in a plurality of genes (i) selectively hybridizes to a first subset of transcripts, in a corresponding plurality of subsets of transcripts in a plurality of transcripts corresponding to the respective gene, or (ii) selectively hybridizes to another subset of transcripts, other than the first subset of transcripts, in the corresponding plurality of subsets of transcripts in the plurality of transcripts corresponding to the respective gene. The plurality of cDNA sequences is obtained from a pool of poly-adenylated mRNA obtained from a biological sample of a subject, where the plurality of cDNA sequences comprises a first subset of cDNA sequences and a second subset of cDNA sequences, each respective cDNA sequence in the first subset of cDNA sequences maps to a respective gene in a plurality of genes, and each respective cDNA sequence in the second subset of cDNA sequences maps to a portion of a reference genome not represented by the plurality of genes. Each respective transcript in the corresponding plurality of transcripts of each respective gene in the plurality of genes is hybridizable to a conjugated nucleic acid bait in the plurality of conjugated nucleic acid baits.

In some embodiments, any of the methods and/or embodiments for nucleic acid baits, design and use of nucleic acid baits, genes, cDNA sequences, transcripts, isoforms, biological samples, methods for hybridization and capture, and/or analysis and applications described in the above sections (see, Section I. Methods for Capturing Targeted Sequences using a Hybridization/Capture Approach and Section II. Methods for Hybridization/Capture Probe Design) are contemplated for use with respect to the presently described plurality of conjugated nucleic acid baits, and any substitutions, modifications, and/or combinations thereof, as will be apparent to one skilled in the art.

In some embodiments, the corresponding non-nucleotide binding moiety comprises biotin, 2-(4-Hydroxyphenylazo) benzoic acid (HABA), or a compound listed in Table 1.

Another aspect of the present disclosure provides a computer system comprising one or more processors, memory, and one or more programs, where the one or more programs are stored in the memory and configured to be executed by the one or more processors, the one or more programs for identifying a plurality of nucleic acid baits (e.g., at least $2 \times 10^3$ nucleic acid baits). The one or more programs include instructions for performing any of the methods and/or embodiments disclosed herein, and/or any combinations or substitutions thereof as will be apparent to one skilled in the art.

Another aspect of the present disclosure provides a computer readable storage medium storing one or more programs, the one or more programs comprising instructions, which when executed by an electronic device with one or more processors and a memory cause the electronic device to identify a plurality of nucleic acid baits (e.g., at least $2 \times 10^3$ nucleic acid baits) by performing any of the methods and/or embodiments disclosed herein, and/or any combinations or substitutions thereof as will be apparent to one skilled in the art.

EXAMPLES

Example 1. Nucleic Acid Bait Design

FIGS. 5A and 5B each illustrate a first nucleic acid bait corresponding to a first sub-sequence and a second nucleic acid bait corresponding to a second sub-sequence, where the first and the second nucleic acid bait were selected in accordance with some embodiments of the present disclosure. In FIG. 5A, each transcript in a plurality of five transcripts 506 corresponding to a respective target gene is represented on a separate track. Two nucleic acid baits are shown: a first nucleic acid bait corresponding to a first sub-sequence 502 that occurs in four out of the five transcripts for the target gene (e.g., the first maximal number of transcripts, defined as the first subset of transcripts), and a second nucleic acid bait corresponding to a second sub-sequence 504 that occurs in a remaining (fifth) transcript for the target gene (e.g., the second maximal number of transcripts other than those transcripts in the corresponding first subset of transcripts).

In FIG. 5B, each transcript in a plurality of nine transcripts 512 corresponding to a respective target gene is represented on a separate track. The plurality of transcripts is obtained based on annotations in a reference database within the GENCODE Consortium (GENCODE Release 32). See, Harrow et al., 2012, "GENCODE: The reference human genome annotation for The ENCODE Project," Genome Res. 22(9): 1760-1774: doi:10.1101/gr.135350.111; and Flicek et al., 2014, "Ensembl 2014," Nucleic Acids Res. 42(Database issue):D749-D755: doi: 10.1093/nar/gkt1196, the entire contents of which are incorporated herein by reference. Two nucleic acid baits are shown: a first nucleic acid bait corresponding to a first sub-sequence 508 that occurs in eight out of the nine transcripts for the target gene (e.g., the first maximal number of transcripts, defined as the first subset of transcripts), and a second nucleic acid bait corresponding to a second sub-sequence 510 that occurs in a remaining (ninth) transcript for the target gene (e.g., the second maximal number of transcripts other than those transcripts in the corresponding first subset of transcripts).

FIGS. 5A and 5B further illustrate an advantage of the presently disclosed method over conventional methods, by designing a minimal probe set that captures all possible transcripts in a plurality of transcripts for a respective target gene (e.g., 2 nucleic acid baits for 5 or more isoforms).

Example 2. Example Workflows for Hybridization Pull-down using Nucleic Acid Baits FIGS. 8A and 8B illustrate two example workflows for obtaining gene expression libraries with nucleic acid baits using a hybridization/capture approach, in accordance with some embodiments of the present disclosure.

FIG. 8A illustrates an example workflow including a hybridization and capture approach using a "final library" of gene expression data (left panel). A plurality of transcripts mapping to a cDNA sequence for a respective gene (e.g., amplified cDNA (802)) was subjected to pre-capture processing, including fragmentation, end-repair, A-tailing, adapter ligation, and SI—PCR (804). Fragmented and pre-processed transcript fragments were then hybridized to a plurality of nucleic acid baits including non-nucleotide binding moieties (e.g., biotinylated probes) mixed with blockers for adapter blocking (806) and capture was performed using pull-down of the non-nucleotide binding moieties (e.g., biotin pull-down), followed by removal of the nucleic acid baits and blockers (808). The enriched plurality of transcript fragments was then amplified to obtain the final, enriched gene expression library (810).

In contrast, another example workflow illustrates a hybridization and capture approach using an unfragmented "cDNA" library (right panel). A plurality of transcripts mapping to a cDNA sequence for a respective gene (e.g., amplified cDNA (802)) was hybridized to a plurality of nucleic acid baits including non-nucleotide binding moieties (e.g., biotinylated probes) mixed with blockers for adapter blocking (812) and capture was performed using pull-down of the non-nucleotide binding moieties (e.g., biotin pull-down), followed by removal of the nucleic acid baits and blockers (814). The enriched plurality of transcripts was then amplified (816) and subjected to post-capture processing, including fragmentation, end-repair, A-tailing, adapter ligation, and SI—PCR (818).

As illustrated in FIG. 8A, the "final library" pull-down approach includes fragmentation of the plurality of transcripts (e.g., cDNA molecules) prior to hybridization and capture by the plurality of nucleic acid baits (e.g., probes). For instance, in some embodiments, the plurality of fragmented transcripts comprises cDNA molecules of 800 bp or less. In contrast, the "cDNA" pull-down approach includes hybridization and capture of unfragmented transcripts (e.g., cDNA molecules) prior to fragmentation. In some such embodiments, the plurality of unfragmented transcripts comprise cDNA molecules of 1000 bp or more.

Without being limited to any one theory of operation, FIG. 8B illustrates an example implementation of the hybridization and capture step of a "final library" pull-down workflow (806) and a "cDNA" pull-down workflow (812). In some embodiments, the longer sequence lengths of the unfragmented transcripts in the cDNA pull-down approach indicate that two or more transcripts in the plurality of transcripts for a respective gene have overlapping sequences. Thus, a method for identifying nucleic acid baits, in accordance with some embodiments of the present disclosure, will in some implementations result in the identification of at least one nucleic acid bait (824) that hybridizes to at least a first transcript (822) and a second transcript (823). In some alternative embodiments, the shorter sequence lengths of the fragmented transcripts in the final library pull-down approach indicate that two or more transcripts in the plurality of transcripts for the respective gene are likely to have unique (e.g., nonoverlapping) sequences. Thus, for instance, a respective nucleic acid bait (828) that hybridizes to a first transcript (827) may not, in some embodiments, hybridize to a second transcript (826) for the same respective gene.

Example 3. Performance Metrics of a Minimal Probe Set

FIGS. 7A, 7B, 7C, 7D, and 7E collectively illustrate example performance metrics for hybrid pull-down of cDNA using a minimal probe set compared to a control probe set, in accordance with an embodiment of the present disclosure.

Figure 7A:
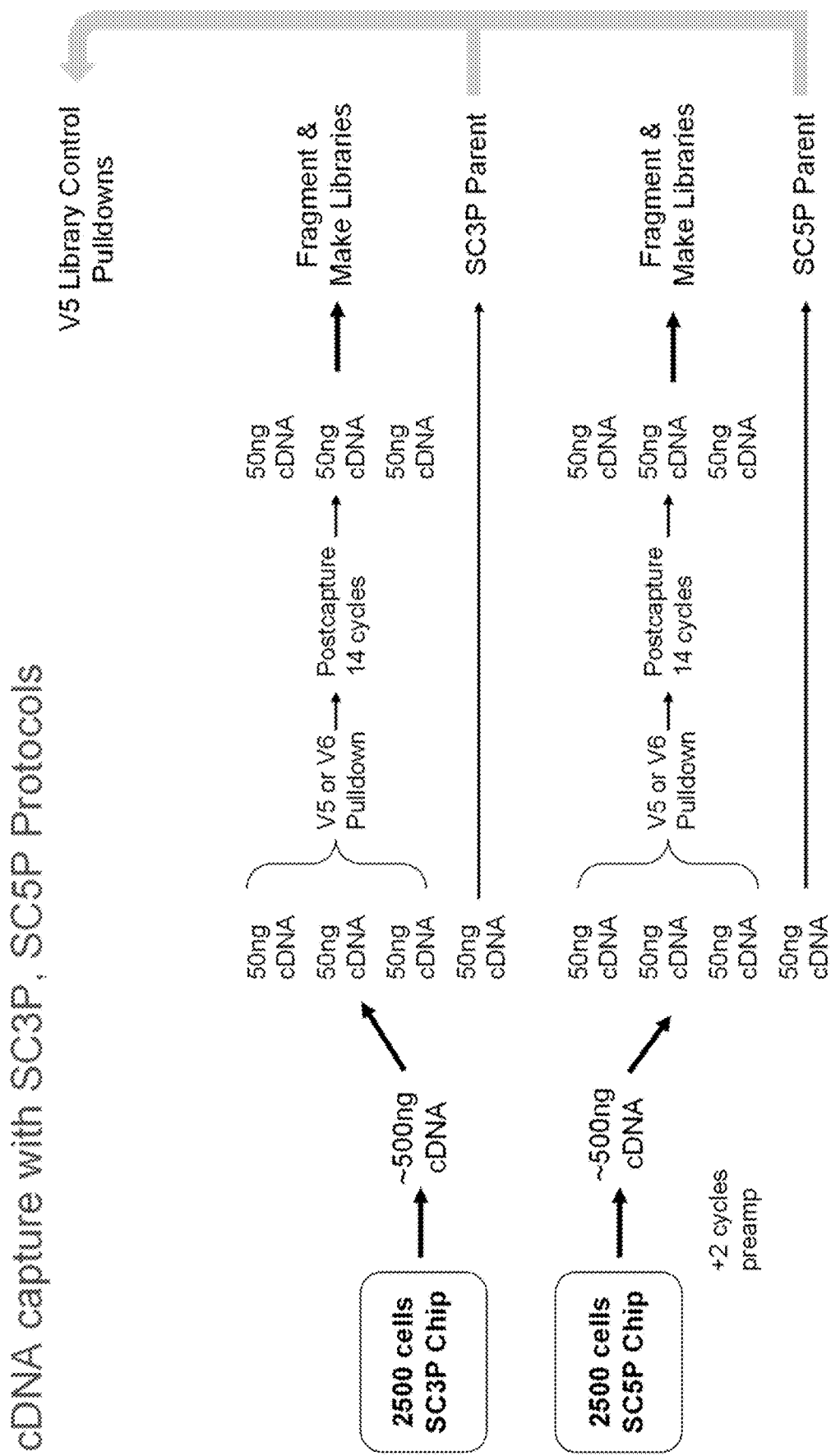
FIGS. 7A, 7B, 7C, 7D, and 7E collectively illustrate example performance metrics for hybrid pull-down of cDNA using a minimal probe set compared to a control probe set, in accordance with an embodiment of the present disclosure.

FIG. 7A provides a schematic for a hybridization and capture approach of a plurality of transcripts mapping to a cDNA sequence for each respective gene in a plurality of genes, for the generation of single-cell 3' (SC3P) and single-cell 5' (SC5P) gene expression libraries. Two aliquots of a biological sample were obtained, each sample containing 2500 cells. From each sample, approximately 500 ng of cDNA was obtained, after reverse transcription and two cycles of amplification. Each sample was further split into three experimental replicates of 50 ng cDNA each, and a control replicate of 50 ng cDNA.

Experimental replicates were used to obtain gene expression libraries using a "cDNA" pull-down approach (as detailed above with reference to FIG. 8A, right panel). Two versions of the cDNA pull-down approach were employed. In a first implementation, the hybridization and capture were performed using the "V5 nucleic acid bait set," which included a plurality of nucleic acid baits tiled across the sequence of the plurality of transcripts corresponding to the respective gene, such that, for each respective gene in the plurality of genes, the plurality of nucleic acid baits included approximately 40-50 nucleic acid baits corresponding to the respective gene. The V5 nucleic acid bait set thus included approximately 40,000-50,000 nucleic acid baits collectively corresponding to a plurality of approximately 1000 genes comprising 3 gene panels of interest (cancer, immune, and pathway gene panels). In a second implementation, the hybridization and capture were performed using the "V6 nucleic acid bait set," which included a plurality of nucleic acid baits minimally tiled across the sequence of the plurality of transcripts corresponding to the respective gene, such that, for each respective gene in the plurality of genes, the plurality of nucleic acid baits included approximately 4 nucleic acid baits corresponding to the respective gene. The V6 nucleic acid bait set thus included approximately 2000-4000 nucleic acid baits, collectively corresponding to the plurality of approximately 1000 genes comprising the 3 gene panels of interest (cancer, immune, and pathway gene panels).

Control replicates were used to obtain gene expression libraries using a "final library" pull-down approach (as detailed above with reference to FIG. 8A, left panel). Hybridization and capture for control replicates were performed using the V5 nucleic acid bait set on pre-fragmented transcripts. Methods for obtaining gene expression libraries are further described in, for example, 10X Genomics, "What is the difference between Single Cell 3' and 5' Gene Expression libraries?" available on the internet at kb.10xgenomics.com/hc/en-us/articles/360000939852-What-is-the-difference-between-Single-Cell-3-and-5-Gene-Expression-libraries-; and 10X Genomics, 2021, "Targeted Gene Expression—Single Cell User Guide", Document Number CG000293, Rev E, each of which is hereby incorporated herein by reference in its entirety.

Figure 7B:
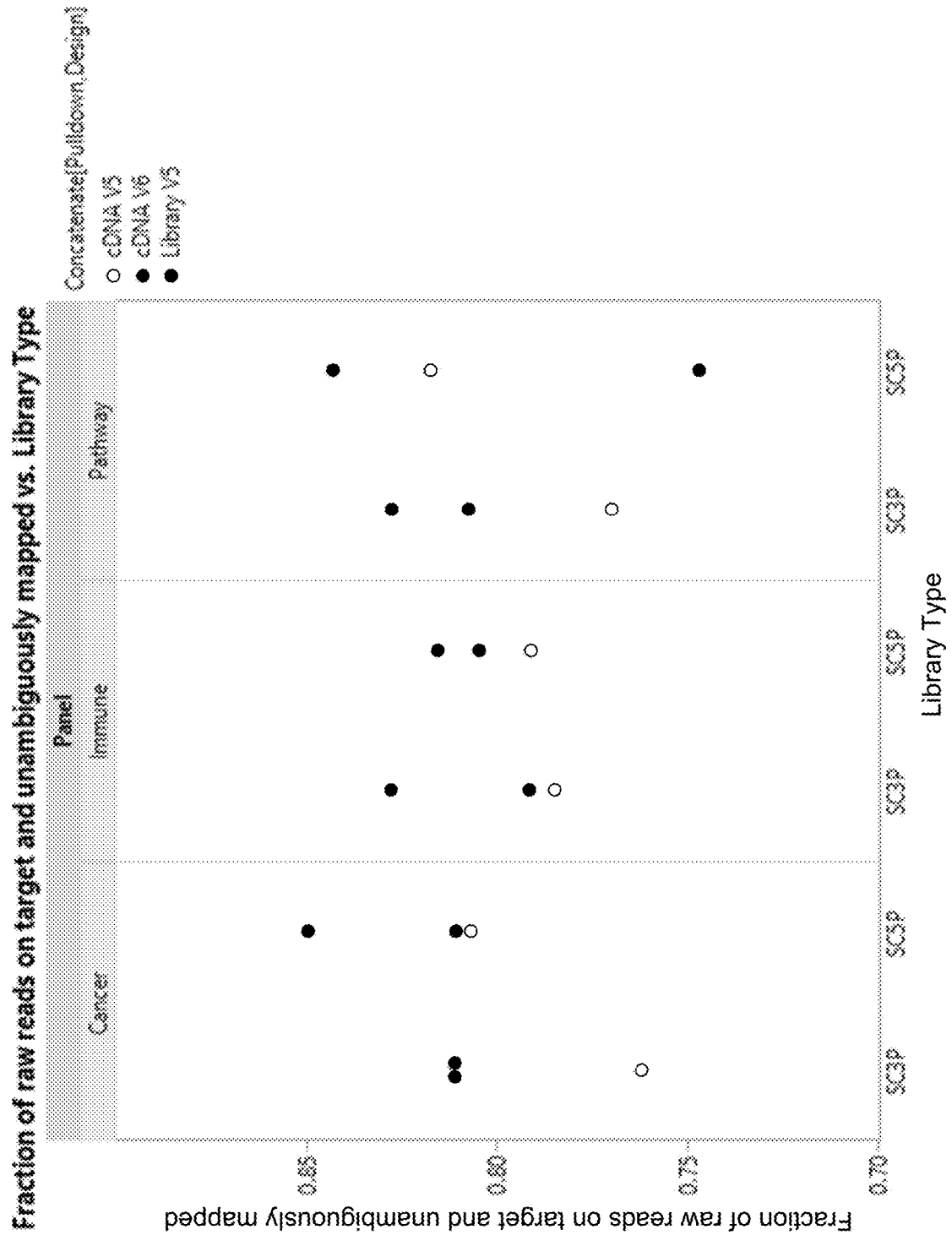
Figure 7C:
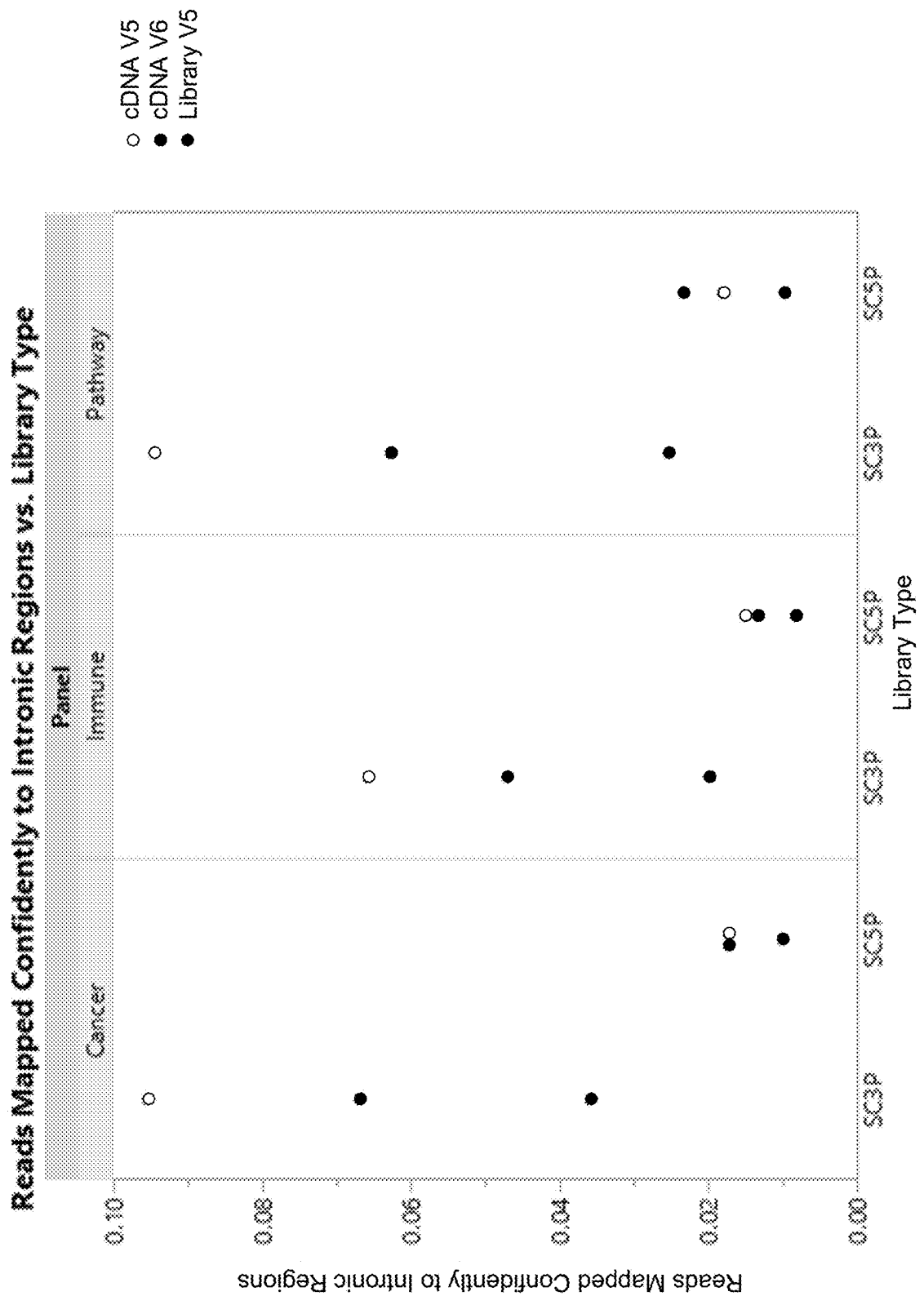

FIGS. 7B, 7C, 7D, and 7E illustrate performance metrics for the V5 cDNA pull-down approach, V6 cDNA pull-down approach, and V5 final library pull-down approach, stratified by gene expression library type (e.g., 3' or 5') and gene panel of interest. FIG. 7B illustrates the fraction of raw reads that map to target genes (e.g., in the plurality of genes collectively represented in plurality of nucleic acid baits) and unambiguously mapped raw reads compared to all reads, where the reads are obtained from sequencing of each of the prepared gene expression libraries. In general, up to a 5% increase of the fraction of on-target reads was observed in the V5 final library pull-down assay ("Library V5") compared to the V5 cDNA pull-down assay ("cDNA V5"), although this observation was reversed in the 5' gene expression library when analyzing only genes in the "Pathway" gene panel. Higher fractions of on-target reads were consistently observed in the V6 cDNA pull-down assay ("cDNA V6") compared to cDNA V5 across all gene panels and all library types, indicating that the minimally tiled plurality of nucleic acid baits (e.g., the reduced bait set) performed better at targeting genes of interest compared to off-target sequences than the larger bait set. FIG. 7C illustrates the fraction of reads mapped confidently to intronic regions compared to all reads obtained from sequencing of each of the prepared gene expression libraries. While similar performance was observed for all assay types across all 5' libraries (>2%), the cDNA V5 and cDNA V6 assays exhibited slightly higher fractions of reads mapped to intronic regions compared to the Library V5 assay (~8-10%, ~6%, and <4%, respectively).

Figure 7D:
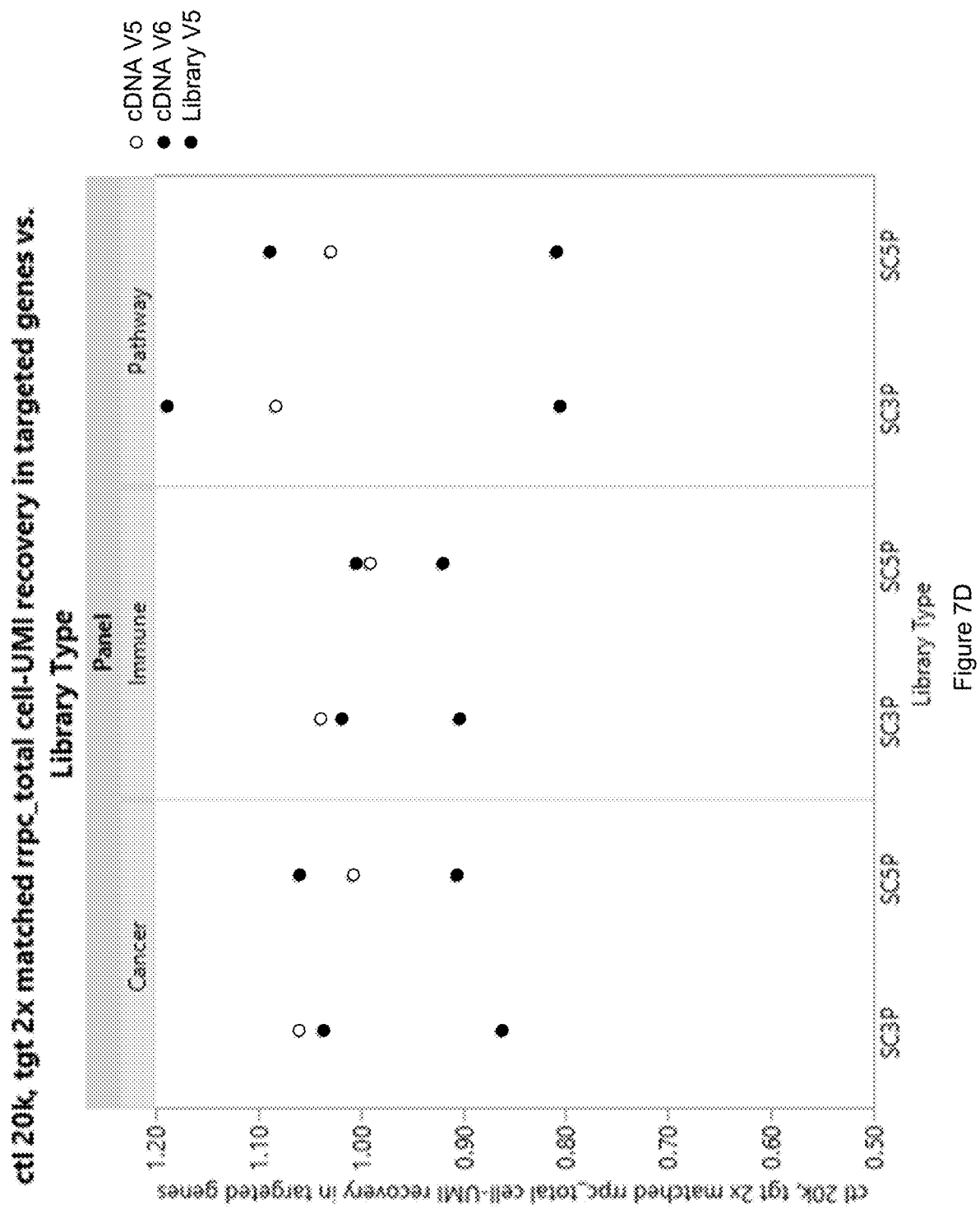
Figure 7E:
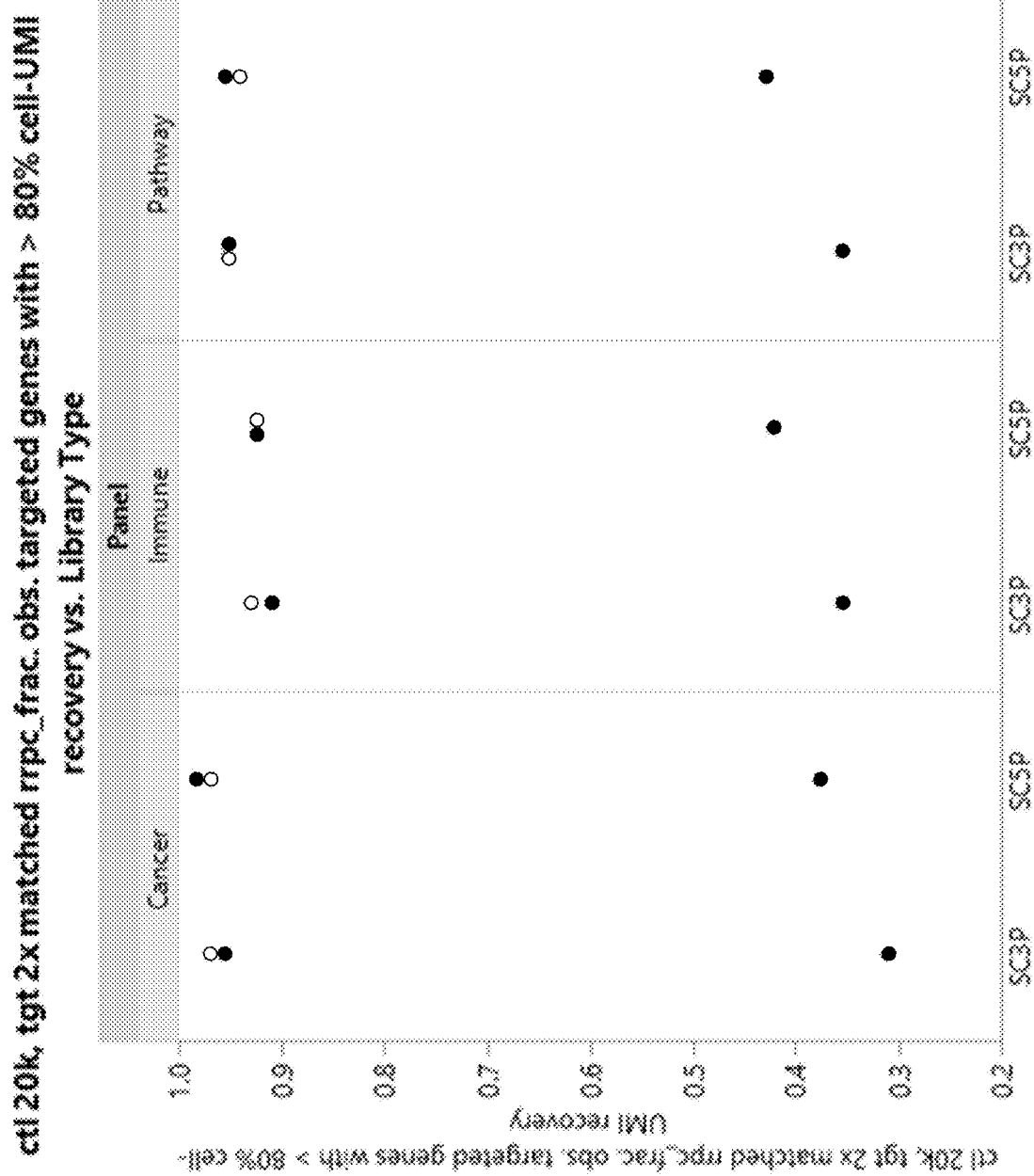

FIG. 7D illustrates the total cell UMI recovery for each assay type, stratified by gene panel and library type. Cell UMI recovery indicates the ability of a respective plurality of nucleic acid baits (e.g., the V5 or V6 bait sets) to hybridize to and capture each respective transcript in the plurality of transcripts mapping to a cDNA sequence for each respective gene in the plurality of genes (e.g., the ~1000 genes collectively represented in the bait sets). For instance, in some embodiments, each respective transcript in the plurality of transcripts corresponding to each respective gene in the plurality of genes is appended with a respective barcode and/or UMI. The sum diversity of UMIs represented in the plurality of transcripts across the plurality of genes is the UMI complexity. Thus, the ability for a respective plurality of nucleic acid baits (e.g., a bait set) to recover (e.g., capture) the full UMI complexity indicates the ability of the plurality of nucleic acid baits to selectively hybridize to and capture each respective transcript in the plurality of transcripts corresponding to each respective gene in the plurality of genes. In other words, higher UMI recovery indicates a greater success rate in hybridizing to all of the transcripts (e.g., isoforms) corresponding to each respective gene in the plurality of genes. In FIG. 7D, comparable performance was observed between the cDNA V5 and Library V5 assays, across all gene panels and library types (~100%). A slight decrease in total cell UMI recovery was observed for the cDNA V6 assay compared to both the cDNA V5 and Library V5 assays, across all gene panels and library types (~80-90%). FIG. 7E illustrates the fraction of observed targeted genes (e.g., in the ~1000 genes collectively represented in the bait sets) with greater than 80% cell UMI recovery. As in FIG. 7D, comparable performance was observed between the cDNA V5 and Library V5 assays, across all gene panels and library types (~100%). However, a significantly lower fraction of target genes with greater than 80% cell UMI recovery was observed in the cDNA V6 assay compared to both the cDNA V5 and Library V5 assays, across all gene panels and library types (~30-40%). Nevertheless, about 60-70% of target genes with greater than 50% cell UMI recovery was observed in the cDNA V6 assay, suggesting a moderate ability in the V6 bait set for hybridization and capture of the plurality of transcripts corresponding to each respective gene in the plurality of genes.

CONCLUSION

All references cited herein are incorporated herein by reference in their entirety and for all purposes to the same extent as if each individual publication or patent or patent application was specifically and individually indicated to be incorporated by reference in its entirety for all purposes.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures, and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method comprising:
A) obtaining a plurality of cDNA sequences from a pool of poly-adenylated mRNA obtained from a biological sample of a subject, wherein
each respective cDNA sequence in the plurality of cDNA sequences is unfragmented,
the plurality of cDNA sequences comprises a first subset of cDNA sequences and a second subset of cDNA sequences,
each respective cDNA sequence in the first subset of cDNA sequences maps to a respective target gene in a plurality of target genes,
each respective cDNA sequence in the second subset of cDNA sequences maps to an off-target portion of a reference genome not represented by the plurality of target genes, and
each respective target gene in the plurality of target genes is characterized by a respective plurality of transcripts comprising overlapping isoforms in a plurality of isoforms for the respective target gene, wherein each respective transcript in the respective plurality of transcripts is a respective isoform for the respective target gene;
B) exposing the plurality of cDNA sequences to a plurality of nucleic acid baits each of length that is between $K_1$ and $K_2$ residues, thereby forming a plurality of nucleic acid bait-sequence read complexes, wherein:
$K_1$ and $K_2$ are positive integers,
the plurality of nucleic acid baits comprises at least $2 \times 10^3$ nucleic acid baits,
each respective nucleic acid bait in the plurality of nucleic acid baits that hybridizes to a cDNA sequence mapping to a respective target gene in the plurality of target genes:
(i) selectively hybridizes to a first subset of transcripts, in a plurality of subsets of transcripts in the respective plurality of transcripts for the respective target gene, or
(ii) selectively hybridizes to another subset of transcripts, other than the first subset of transcripts, in the plurality of subsets of transcripts in the respective plurality of transcripts for the respective target gene, and
for each respective target gene in the plurality of target genes, the plurality of nucleic acid baits hybridizes to all of the overlapping isoforms in the plurality of isoforms for the respective target gene;
C) selectively capturing the plurality of nucleic acid bait—sequence read complexes; and
D) analyzing the plurality of nucleic acid bait—sequence read complexes captured by the selectively capturing C).

2. The method of claim 1, wherein the analyzing the plurality of nucleic acid bait-sequence read complexes captured by the selectively capturing C) identifies one or more analytes in the biological sample.

3. The method of claim 1, wherein the selectively capturing the plurality of nucleic acid bait—sequence read complexes C) captures the plurality of nucleic acid bait—sequence read complexes to a solid support.

4. The method of claim 3, wherein the solid support comprises a bead.

5. The method of claim 4, wherein,
each nucleic acid bait in the plurality of nucleic acid baits comprises a non-nucleotide binding moiety,
the solid support comprises a plurality of capture moieties, and
a respective nucleic acid bait—sequence read complex in the plurality of nucleic acid bait—sequence read complexes is captured on the solid support through a reaction between a capture moiety in the plurality of capture moieties and the non-nucleotide binding moiety of the respective nucleic acid bait—sequence read complex.

6. The method of claim 5, wherein a capture moiety in the plurality of capture moieties comprises streptavidin and the non-nucleotide binding moiety of the respective nucleic acid bait—sequence read complex comprises an affinity moiety selected from the group consisting of biotin and 2-(4-Hydroxyphenylazo)benzoic acid (HABA).

7. The method of claim 1, wherein each respective nucleic acid bait in the plurality of nucleic acid baits shares less than a threshold percentage of sequence identity to any other nucleic acid bait in the plurality of nucleic acid baits.

8. The method of claim 7, wherein the threshold percentage of sequence identity is ten percent, twenty percent, thirty percent, or between five and fifty percent.

9. The method of claim 1, the method further comprising filtering the plurality of nucleic acid baits for a filtering criterion selected from the group consisting of: mappability, absence of repetitive subsequences, overall GC content, coverage, a minimum threshold sequence identity to the reference genome, a maximum threshold number of times a nucleic acid bait is represented in the reference genome, a minimum threshold distance from a substring of the reference genome that is represented in the reference genome at least a threshold number of times, a minimum threshold distance from any annotated start site of a respective target gene, a minimum threshold distance from any annotated stop site of a respective target gene, a minimum threshold distance from a 3' end of a respective cDNA sequence, a minimum threshold distance from a 5' end of a respective cDNA sequence, a presence of unannotated poly-A sites, and a threshold Tm range.

10. The method of claim 1, wherein the respective plurality of transcripts for a respective target gene comprises five or more transcripts for the respective target gene.

11. The method of claim 1, wherein the first subset of transcripts consists of two or more transcripts.

12. The method of claim 1, wherein the plurality of nucleic acid baits includes a minimum number of baits necessary to selectively hybridize to each respective transcript in the respective plurality of transcripts for a respective target gene in the plurality of target genes, wherein each respective transcript in the respective plurality of transcripts for the respective target gene is hybridizable to only one nucleic acid bait in the plurality of nucleic acid baits.

13. The method of claim 1, wherein the plurality of nucleic acid baits consists of a minimum number of baits necessary to selectively hybridize to each respective transcript in the respective plurality of transcripts for each respective target gene in the plurality of target genes.

14. The method of claim 2, wherein an analyte in the one or more analytes comprises a mutation.

15. The method of claim 2, wherein an analyte in the one or more analytes comprises an alternative allele of a single nucleotide polymorphism (SNP).

16. The method of claim 1, wherein the plurality of cDNA sequences is at least $1 \times 10^6$ cDNA sequences.

17. The method of claim 1, wherein the respective plurality of transcripts for a respective target gene is each transcript of the respective target gene annotated in GENCODE Release 33 (GRCh38.p 13).

18. The method of claim 1, wherein $K_1$ is 25 and $K_2$ is 1000.

19. The method of claim 1, wherein each respective substring of fixed length P nucleotides in each respective nucleic acid bait in the plurality of nucleic acid baits is represented in the reference genome less than a threshold number of times L.

20. The method of claim 19, wherein P is at least 15 nucleotides.

21. The method of claim 1, wherein each respective nucleic acid bait in the plurality of nucleic acid baits comprises a nucleic acid sequence that has a minimal identity to the reference genome of at least 90%.

22. The method of claim 1, the method further comprising obtaining the plurality of nucleic acid baits, comprising: designing a nucleic acid bait in the plurality of nucleic acid baits for a respective target gene in the plurality of target genes using:
when the length of the coding sequence of the respective target gene satisfies a predetermined length threshold, the coding sequence of the respective target gene, and
when the length of the coding sequence of the respective target gene does not satisfy a predetermined length threshold, an mRNA sequence of the respective target gene.

23. The method of claim 1, the method further comprising modifying a sequence of a nucleic acid bait in the plurality of nucleic acid baits that is represented in the reference genome at a position that is less than a threshold number of base pairs M away from any portion of the reference genome that comprises a substring of fixed length P that is represented in the reference genome at least a threshold number of times L, wherein the modifying comprises:
(i) removing the respective nucleic acid bait from the plurality of nucleic acid baits,
(ii) truncating the respective nucleic acid bait such that the respective nucleic acid bait is represented in the reference genome at a position that is at least Mbase pairs away from any portion of the reference genome that comprises the substring of fixed length P, or
(iii) shifting the respective sequence of the nucleic acid bait along the reference genome such that the respective sequence of the nucleic acid bait is represented in the reference genome at a position that is at least Mbase pairs away from any portion of the reference genome that comprises the substring of fixed length P.

24. The method of claim 23, wherein P is between 10 and 75.

25. The method of claim 23, wherein L is between 2 and 1000.

26. The method of claim 1, wherein the analyzing the plurality of nucleic acid bait-sequence read complexes captured by the selectively capturing C) comprises sequencing of nucleic acid bait—sequence read complexes captured in C).

27. The method of claim 1, wherein each transcript in the respective plurality of transcripts for a respective target gene is protein coding.

28. The method of claim 1, wherein each transcript in the respective plurality of transcripts for a respective target gene has GENCODE transcript support level 1, GENCODE transcript support level 2, or GENCODE transcript support level 3.

29. The method of claim 1, wherein each respective nucleic acid bait in the plurality of nucleic acid baits that hybridizes to a cDNA sequence mapping to a respective target gene in the plurality of target genes hybridizes to a region of the respective target gene that is at least a minimum threshold distance away from a position selected from the group consisting of:

an annotated start site of the respective target gene,
an annotated stop site of the respective target gene,
a 3' end of any cDNA sequence mapping to the respective target gene, and
a 5' end of any cDNA sequence mapping to the respective target gene.

30. The method of claim 29, wherein the minimum threshold distance is from 20 to 2000 base pairs.

31. The method of claim 1, wherein the plurality of target genes comprises at least 10, at least 50, or at least 100 target genes.

32. The method of claim 1, wherein each nucleic acid bait in the plurality of nucleic acid baits hybridizes to a cDNA sequence that maps to a respective target gene in the plurality of target genes.

33. The method of claim 1, wherein the selectively capturing the plurality of nucleic acid bait—sequence read complexes comprises enriching for cDNA sequences in the first subset of cDNA sequences by removing all or a portion of the second subset of cDNA sequences.

34. The method of claim 33, wherein the analyzing the plurality of nucleic acid bait—sequence read complexes captured by the selectively capturing C) comprises sequencing of nucleic acid bait—sequence read complexes captured in C), and wherein the removing all or a portion of the second subset of cDNA sequences reduces sequencing requirements.

\* \* \* \* \*